United States Patent
Aloqaily et al.

(10) Patent No.: US 12,125,117 B2
(45) Date of Patent: Oct. 22, 2024

(54) COOPERATIVE HEALTH INTELLIGENT EMERGENCY RESPONSE SYSTEM FOR COOPERATIVE INTELLIGENT TRANSPORT SYSTEMS

(71) Applicant: Mohamed bin Zayed University of Artificial Intelligence, Abu Dhabi (AE)

(72) Inventors: Moayad Aloqaily, Abu Dhabi (AE); Haya Elayan, Abu Dhabi (AE); Mohsen Guizani, Abu Dhabi (AE); Fakhri Karray, Abu Dhabi (AE)

(73) Assignee: Mohamed bin Zayed University of Artificial Intelligence, Abu Dhabi (AE)

( * ) Notice: Subject to any disclaimer, the term of this patent is extended or adjusted under 35 U.S.C. 154(b) by 101 days.

(21) Appl. No.: 17/959,483

(22) Filed: Oct. 4, 2022

(65) Prior Publication Data
US 2024/0127384 A1   Apr. 18, 2024

(51) Int. Cl.
*G06Q 50/26* (2024.01)
*A61B 5/00* (2006.01)
(Continued)

(52) U.S. Cl.
CPC ............ *G06Q 50/265* (2013.01); *A61B 5/26* (2021.01); *A61B 5/282* (2021.01); *A61B 5/6893* (2013.01);
(Continued)

(58) Field of Classification Search
CPC ...... G06Q 50/265; G16H 40/67; G16H 50/30; A61B 5/282; A61B 5/26; A61B 5/6893; G06N 3/044; G06N 3/08
See application file for complete search history.

(56) References Cited

U.S. PATENT DOCUMENTS

| | | | | |
|---|---|---|---|---|
| 6,796,581 B2 * | 9/2004 | Karray | .................... | B60R 21/26 422/165 |
| 6,889,215 B2 * | 5/2005 | Basir | ................. | B60R 21/01556 706/14 |

(Continued)

OTHER PUBLICATIONS

Miglani, 2021, Elsevier, pp. 37-63.*
(Continued)

*Primary Examiner* — Michael I Ezewoko
(74) *Attorney, Agent, or Firm* — Oblon, McClelland, Maier & Neustadt, L.L.P.

(57) ABSTRACT

A system, method and computer readable medium for emergency health response, including sensors for measuring health conditions of a user, a local machine learning device to predict abnormalities in health status of the user based on the measurements, a communications device for transmitting an emergency alert message to emergency response providers that are within range of the communications device, and for receiving response messages from emergency response providers that are available to provide emergency treatment. A health condition controller selecting a provider. When the provider is a hospital, the subject vehicle will set its destination to the hospital and will transmit health status information of the user to the provider. When the provider is an emergency response vehicle, the subject vehicle will communicate coordinates as a meeting destination for meeting the provider response vehicle and will transmit health status information of the user to the provider response vehicle.

16 Claims, 35 Drawing Sheets

(51) Int. Cl.
| | | |
|---|---|---|
| *A61B 5/26* | (2021.01) | |
| *A61B 5/282* | (2021.01) | |
| *G06N 3/044* | (2023.01) | |
| *G06N 3/08* | (2023.01) | |
| *G16H 40/67* | (2018.01) | |
| *G16H 50/30* | (2018.01) | |

(52) U.S. Cl.
CPC .............. *G06N 3/044* (2023.01); *G06N 3/08* (2013.01); *G16H 40/67* (2018.01); *G16H 50/30* (2018.01)

(56) References Cited

U.S. PATENT DOCUMENTS

| | | | | |
|---|---|---|---|---|
| 6,916,041 | B2* | 7/2005 | Karray | B60R 21/264 280/736 |
| 6,989,496 | B2* | 1/2006 | Desrochers | B60R 21/01554 177/144 |
| 7,899,225 | B2* | 3/2011 | Collins | A61B 5/4064 600/407 |
| 7,974,714 | B2* | 7/2011 | Hoffberg | H04N 21/4318 360/75 |
| 8,755,837 | B2* | 6/2014 | Rhoads | G06V 10/56 382/312 |
| 8,873,813 | B2* | 10/2014 | Tadayon | G06V 40/172 382/118 |
| 8,954,365 | B2* | 2/2015 | Criminisi | G06F 18/231 706/45 |
| 9,075,879 | B2* | 7/2015 | Shehata | G06F 16/951 |
| 9,202,253 | B2* | 12/2015 | Macoviak | G16H 40/20 |
| 9,224,180 | B2* | 12/2015 | Macoviak | G06Q 40/08 |
| 9,390,161 | B2* | 7/2016 | Shehata | G06F 40/289 |
| 9,646,134 | B2* | 5/2017 | Sanborn | G16B 30/00 |
| 11,234,054 | B2* | 1/2022 | Bilal | H04N 21/6405 |
| 11,494,700 | B2* | 11/2022 | Pastore | G06N 20/00 |
| 11,540,879 | B2* | 1/2023 | Bort | A61B 18/1492 |
| 11,583,346 | B2* | 2/2023 | Bort | A61B 5/7264 |
| 11,681,951 | B2* | 6/2023 | Pastore | G06F 40/30 706/12 |
| 11,694,122 | B2* | 7/2023 | Szeto | G16H 10/60 706/10 |
| 11,756,244 | B1* | 9/2023 | Bhunia | G06F 3/04886 715/268 |
| 11,800,166 | B2* | 10/2023 | Baccour | H04N 21/26241 |
| 2001/0044720 | A1* | 11/2001 | Lee | G06F 16/3334 704/251 |
| 2001/0047344 | A1* | 11/2001 | Basir | B60R 21/01556 706/8 |
| 2002/0193780 | A1* | 12/2002 | Karray | A61B 18/201 606/14 |
| 2003/0173120 | A1* | 9/2003 | Desrochers | B60R 21/01554 177/144 |
| 2003/0184067 | A1* | 10/2003 | Karray | B60R 21/26 280/741 |
| 2004/0051288 | A1* | 3/2004 | Karray | B60R 21/264 280/741 |
| 2005/0197783 | A1* | 9/2005 | Kuchinsky | G16B 5/20 707/999.001 |
| 2006/0063156 | A1* | 3/2006 | Willman | A61P 35/02 435/325 |
| 2009/0037351 | A1* | 2/2009 | Kristal | G09B 7/06 706/12 |
| 2009/0203588 | A1* | 8/2009 | Willman | C12Q 1/6886 435/7.1 |
| 2010/0168533 | A1* | 7/2010 | Johnsen | G16Z 99/00 600/301 |
| 2011/0228976 | A1* | 9/2011 | Fitzgibbon | G06V 10/754 382/103 |
| 2012/0233181 | A1* | 9/2012 | Shehata | G06F 16/951 707/E17.108 |
| 2012/0246100 | A1* | 9/2012 | Shehata | G06F 16/345 707/706 |
| 2012/0303558 | A1* | 11/2012 | Jaiswal | G06N 20/00 706/12 |
| 2013/0085773 | A1* | 4/2013 | Yao | G16H 50/70 705/2 |
| 2013/0090254 | A1* | 4/2013 | Lamb | G16B 25/10 702/20 |
| 2014/0038836 | A1* | 2/2014 | Higgins | G16B 30/10 435/325 |
| 2014/0046696 | A1* | 2/2014 | Higgins | G16H 50/20 705/3 |
| 2014/0074760 | A1* | 3/2014 | Boldyrev | G06N 20/00 706/12 |
| 2014/0088989 | A1* | 3/2014 | Krishnapuram | G16H 50/50 705/2 |
| 2014/0142970 | A1* | 5/2014 | Baronov | A61B 5/7275 705/2 |
| 2014/0222349 | A1* | 8/2014 | Higgins | G16B 20/00 702/19 |
| 2014/0222737 | A1* | 8/2014 | Chen | G06N 20/20 706/12 |
| 2015/0170055 | A1* | 6/2015 | Beymer | G06N 20/00 706/12 |
| 2015/0199010 | A1* | 7/2015 | Coleman | H04L 67/01 345/156 |
| 2016/0055307 | A1* | 2/2016 | Macoviak | G16H 20/10 705/2 |
| 2016/0055410 | A1* | 2/2016 | Spagnola | G06N 3/02 706/16 |
| 2016/0055427 | A1* | 2/2016 | Adjaoute | G06Q 30/0201 706/12 |
| 2016/0071017 | A1* | 3/2016 | Adjaoute | G06Q 20/4016 706/52 |
| 2016/0078367 | A1* | 3/2016 | Adjaoute | G06F 16/215 706/12 |
| 2018/0018590 | A1* | 1/2018 | Szeto | G16H 50/20 |
| 2018/0181842 | A1* | 6/2018 | Liao | G06F 18/24147 |
| 2019/0359056 | A1 | 11/2019 | Wilson et al. | |
| 2020/0126438 | A1* | 4/2020 | Shehata | G06N 3/02 |
| 2021/0029413 | A1* | 1/2021 | Bilal | H04N 21/6405 |
| 2021/0112116 | A1* | 4/2021 | Baccour | H04N 21/262 |
| 2021/0373563 | A1 | 12/2021 | Christensen et al. | |
| 2021/0374608 | A1* | 12/2021 | El-Khamy | G06N 20/20 |
| 2022/0012637 | A1* | 1/2022 | Rezazadegan Tavakoli | G06N 3/088 |
| 2022/0292346 | A1* | 9/2022 | Mimassi | G06F 40/30 |
| 2022/0300618 | A1* | 9/2022 | Ding | G06F 21/60 |
| 2023/0019669 | A1* | 1/2023 | Alabbasi | G06N 3/04 |
| 2023/0062506 | A1* | 3/2023 | Gouissem | H04W 12/02 |
| 2023/0117768 | A1* | 4/2023 | Shaloudegi | G06N 20/00 706/12 |
| 2023/0222395 | A1* | 7/2023 | Sesha | G06N 3/045 706/12 |
| 2023/0284139 | A1* | 9/2023 | Ma | H04W 28/0205 370/329 |
| 2023/0289591 | A1* | 9/2023 | Cyras | G06N 5/045 |
| 2023/0316603 | A1* | 10/2023 | Bhunia | G06V 30/226 715/268 |
| 2023/0401824 | A1* | 12/2023 | Khan | G06V 20/70 |
| 2023/0414189 | A1* | 12/2023 | Saeed | A61B 6/5294 |
| 2024/0127384 | A1* | 4/2024 | Aloqaily | G16H 50/20 |
| 2024/0135496 | A1* | 4/2024 | Dudhane | G06T 3/4076 |
| 2024/0153308 | A1* | 5/2024 | Fiaz | G06V 20/59 |
| 2024/0161334 | A1* | 5/2024 | Thawakar | G06T 7/73 |
| 2024/0161360 | A1* | 5/2024 | Kumar | G06V 10/44 |

OTHER PUBLICATIONS

Muhammad, 2021, Elsevier, pp. 355-375.*
Rahman, 2020, IEEE, ppa 1-17.*
Wang, Apr. 2022, Elsevier, pp. 1-16.*
Avleen Kaur Malhi, et al., "XML Based Wireless Patient Monitoring System Using Vehicular Ad-Hoc Networks", IEEE International Conference on Computer and Information Technology; Ubiquitous Computing and Communications; Dependable, Autonomic and Secure Computing; Pervasive Intelligence and Computing, Oct. 26-28, 2015, pp. 1087-1094 (Abstract only).

(56) References Cited

OTHER PUBLICATIONS

Mustain Billah, et al., "A Systematic Literature Review on Blockchain Enabled Federated Learning Framework for Internet of Vehicles", IEEE Access, arXiv:2203.05192v1, vol. 4, 2016, pp. 1-21.

* cited by examiner

COOPERATIVE HEALTH INTELLIGENT EMERGENCY RESPONSE SYSTEM FOR COOPERATIVE INTELLIGENT TRANSPORT SYSTEMS

STATEMENT REGARDING PRIOR DISCLOSURE BY THE INVENTORS

Aspects of this technology are described in an article H. Elayan, M. Aloqaily, H. B. Salameh, and M. Guizani, "Intelligent cooperative health emergency response system in autonomous vehicles," in *Proc. IEEE 46th Conf. Local Comput. Netw.* (*LCN*), October 2021, pp. 293-298, and is incorporated herein by reference in its entirety.

Aspects of this technology are described in an article H. Elayan, M. Aloqaily, and M. Guizani, "Digital twin for intelligent context-aware IoT healthcare systems," *IEEE Internet Things J.*, vol. 8, no. 23, pp. 16749-16757, December 2021, and is incorporated herein by reference in its entirety.

Aspects of this technology are described in an article M. Aloqaily, H. Elayan and M. Guizani, "C-HealthIER: A Cooperative Health Intelligent Emergency Response System for C-ITS," in IEEE Transactions on Intelligent Transportation Systems, Feb. 9, 2022, and is incorporated herein by reference in its entirety.

BACKGROUND

Technical Field

The present disclosure is directed to a cooperative health intelligent emergency response system and method that minimizes the time to receive first emergency treatment by an emergency treatment provider, using a federated intelligent health monitoring system. The emergency response system includes an in-vehicle process and an out-vehicle process.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Cooperative intelligent transportation systems are undergoing development as levels of autonomy of vehicles continue to increase and as communication between vehicles is being added to more and more vehicles as part of an Internet of Things infrastructure. Vehicle safety features and driver assist technologies are being developed and incorporated into vehicles, starting out as features that are included with high-end vehicles, and steadily being migrated into mid-range vehicles. Communication between vehicles is limited mainly be security concerns, such as issues involved with access to control functions and data that is typically accessible only by devices that directly connect with vehicle internal systems, and by way of special codes and hardware to manually access internal vehicle codes. Some vehicle communication is available by way of subscription services, and some communication is available via cellular communication using a smartphone of other cellular communication device.

As safety features, driver assist technologies, and communication between vehicles, and between vehicles and other devices continues to evolve, the ability to handle emergency conditions can make use of these changes. There are many potential applications for cooperative intelligent transportation systems including cooperative health emergency response systems that can utilize autonomous vehicles (Avs), particularly for a case where a passenger exhibits an abnormal health status. See H. Elayan, M. Aloqaily, H. B. Salameh, and M. Guizani, "Intelligent cooperative health emergency response system in autonomous vehicles," in *Proc. IEEE 46th Conf. Local Comput. Netw.* (*LCN*), October 2021, pp. 293-298, incorporated herein by reference in its entirety. However, these applications are still in their early stages as a research area, with few research publications available that are related to human health monitoring systems in AVs. *Cooperative Health Emergency Response*: "Smart wireless healthcare monitoring for drivers community" describes health monitoring systems for drivers while inside their cars using Bluetooth technology. See K. C. Kavitha and R. Perumalraja, "Smart wireless healthcare monitoring for drivers community," in *Proc. Int. Conf. Commun. Signal Process.*, April 2014, pp. 1105-1108, incorporated herein by reference in its entirety. A research proposal is that when health abnormalities are detected, the health status is sent to healthcare providers through a cellular network. This proposal also describes a corresponding mobile application that reads data from sensors and sends anomaly information to transport offices and health service providers.

However, in most research proposals abnormalities are determined based on whether health status values are significantly different from normal value details. Abnormalities are communicated to both healthcare service providers and a transport office via cellular networks. It is up to healthcare professionals to take necessary action using ambulance service and a Transport Corporation to ensure a driver's health status or to arrange an alternative driver. Consequently, this proposed service for health monitoring heavily relies on decisions by healthcare professionals and coordination with a transport office.

One proposed passenger health monitoring system in self-driving vehicles uses more advanced technology such as 5G-enabled devices. However, the 5G-enabled devices are utilized for their communications capabilities and do not include artificial intelligence (AI) capabilities. See M. I. Mamun, A. Rahman, M. A. Khaleque, M. F. Mridha, and M. A. Hamid, "Healthcare monitoring system inside self-driving smart car in 5G cellular network," in *Proc. IEEE 17th Int. Conf. Ind. Informat.* (*INDIN*), July 2019, pp. 1515-1520, incorporated herein by reference in its entirety.

Improvements in the on-board health of passengers in driverless cars have been proposed. The improvements are generally described as involving use of a real-time heart rate monitoring system. Heart rate data is extracted by detecting changes in the passenger's skin color through a camera integrated into the vehicle's system. See R. M. Fouad, A. Onsy, and O. A. Omer, "Improvement of driverless Cars' passengers on board health and safety, using low-cost real-time heart rate monitoring system," in *Proc. 24th Int. Conf. Autom. Comput.* (*ICAC*), September 2018, pp. 1-6, incorporated herein by reference in its entirety. Other than the improvements, this work focuses on how driverless cars themselves should act in response to serious medical emergency situations.

Another type of health monitoring device being developed is a stress sensor. One stress sensor has been incorporated into gloves. Stress indicators are transmitted from the gloves to a mobile device via Bluetooth, and corresponding stress levels are categorized into two categories using a support-vector-machine algorithm. See B. G. Lee and W. Y. Chung, "Wearable glove-type driver stress detection using a motion sensor," *IEEE Trans. Intell. Transp. Syst.*, vol. 18, no. 7, pp. 1835-1844, July 2016, incorporated herein by reference in its entirety. However, such glove-based sensor is only for monitoring stress levels.

A description of a more complete passenger health monitoring system has been for an intelligent health monitoring system for connected cars using an air-cushioned car seat to detect ECG and EEG abnormalities and stroke onset. See S. J. Park, S. Hong, D. Kim, I. Hussain, and Y. Seo, "Intelligent in-car health monitoring system for elderly drivers in connected car," in *Proc. Congr. Int. Ergonom. Assoc.*, 2018, pp. 40-44, incorporated herein by reference in its entirety. However, the health monitoring system is set up to monitor health status data using in-vehicle sensors and does not involve cooperative vehicle behavior in order to rescue the driver.

Some research in cooperative vehicle behavior has been directed to the development of methods of cooperative vehicle positioning. For example, the authors of "Implicit cooperative positioning in vehicular networks," "Cooperative vehicular positioning with VANET in urban environments," and "CNVPS: Cooperative neighboring vehicle positioning system based on Vehicle-to-Vehicle communication" discussed the cooperative positioning for autonomous vehicles. This research presented different algorithms and techniques for cooperative positioning using V2V or V2V and V2I communications to improve the global positioning system (GPS)- or the Global Navigation Satellite Systems (GNSS)-based techniques. See G. Soatti, M. Nicoli, N. Garcia, B. Denis, R. Raulefs, and H. Wymeersch, "Implicit cooperative positioning in vehicular networks," *IEEE Trans. Intell. Transp. Syst.*, vol. 19, no. 12, pp. 3964-3980, December 2018; M. A. Hossain, I. Elshafiey, and A. Al-Sanie, "Cooperative vehicular positioning with VANET in urban environments," in *Proc. IEEE Asia-Pacific Conf. Appl. Electromagn. (APACE)*, 2016, pp. 393-396; and S. Nam, D. Lee, J. Lee, and S. Park, "CNVPS: Cooperative neighboring vehicle positioning system based on Vehicle-to-Vehicle communication," *IEEE Access*, vol. 7, pp. 16847-16857, 2019, each incorporated herein by reference in their entirety. The results of this research showed an improvement in the accuracy of positioning of vehicles compared to conventional GPS-based methods. Similarly, a proposal in "Cooperative position prediction: Beyond vehicle-to-vehicle relative positioning," discussed a cooperative position prediction technique for V2V real-time relative positioning in order to satisfy accuracy and timeliness parameters for vehicles. See K. Ansari, "Cooperative position prediction: Beyond vehicle-to-vehicle relative positioning," *IEEE Trans. Intell. Transp. Syst.*, vol. 21, no. 3, pp. 1121-1130, March 2019, incorporated herein by reference in its entirety. However, this research in positioning does not involve emergency situations that are determined based on health status conditions of a passenger.

Research is being performed in the area of cooperative vehicle technologies, including cooperative lane changing, cooperative cruise control, cooperative speed limit control, cooperative parking, and cooperative traffic control.

In the area of cooperative lane changing: the authors of "Cooperative lane changing strategies to improve traffic operation and safety nearby freeway off-ramps in a connected and automated vehicles environment," "Balancing computation speed and quality: A decentralized motion planning method for cooperative lane changes of connected and automated vehicles," and "A cooperative lane change model for connected and automated vehicles" presented solutions for the Cooperative Lane Changing application for both connected and automated vehicles. See Y. Zheng, B. Ran, X. Qu, J. Zhang, and Y. Lin, "Cooperative lane changing strategies to improve traffic operation and safety nearby freeway off-ramps in a connected and automated vehicles environment," *IEEE Trans. Intell. Transp. Syst.*, vol. 21, no. 11, pp. 4605-4614, November 2020; B. Li, Y. Zhang, Y. Feng, Y. Zhang, Y. Ge, and Z. Shao, "Balancing computation speed and quality: A decentralized motion planning method for cooperative lane changes of connected and automated vehicles," *IEEE Trans. Intell. Veh.*, vol. 3, no. 3, pp. 340-350, September 2018; and T. Li et al., "A cooperative lane change model for connected and automated vehicles," *IEEE Access*, vol. 8, pp. 54940-54951, 2020, each incorporated herein by reference in their entirety. While the study in Zheng et al. proposed a strategy for improving the driving process in the cooperative lane changing, that of Li et al. (2018) focused on the multiple vehicle motion planning problem, and Li et al. (2020) focused on collaborative trajectory planning by taking safety and efficiency into account. Through the results of the experiments carried out, Zheng et al. showed that the cooperative method could improve traffic operations, safety, and fluctuation. The authors in Li et al. (2018) showed that the proposed method could avoid direct handling of difficult challenging avoidance conditions, and thus be able to perform the calculation fast. Authors in Li et al. (2020) showed that vehicle cooperation helps achieve safe and effective lane changes.

In the area of cooperative cruise control, the authors in Sakhdari et al., Li et al. (2017), Yang et al., and Gao et al. proposed algorithms and approaches to enhance cooperative cruise control with different objectives. See B. Sakhdari and N. L. Azad, "A distributed reference governor approach to ecological cooperative adaptive cruise control," *IEEE Trans. Intell. Transp. Syst.*, vol. 19, no. 5, pp. 1496-1507, May 2017; Y. Li, C. Xu, L. Xing, and W. Wang, "Integrated cooperative adaptive cruise and variable speed limit controls for reducing rear-end collision risks near freeway bottlenecks based on micro-simulations," *IEEE Trans. Intell. Transp. Syst.*, vol. 18, no. 11, pp. 3157-3167, November 2017; H. Yang, H. Rakha, and M. V. Ala, "Eco-cooperative adaptive cruise control at signalized intersections considering queue effects," *IEEE Trans. Intell. Transp. Syst.*, vol. 18, no. 6, pp. 1575-1585, June 2016; and W. Gao, J. Gao, K. Ozbay, and Z. P. Jiang, "Reinforcement-learning-based cooperative adaptive cruise control of buses in the Lincoln tunnel corridor with time-varying topology," *IEEE Trans. Intell. Transp. Syst.*, vol. 20, no. 10, pp. 3796-3805, October 2019, each incorporated herein by reference in its entirety. The authors in "A distributed reference governor approach to ecological cooperative adaptive cruise control" proposed predictive platoon controllers with the aim of improving the total energy economy of the entire platoon. The proposed approach achieved its aim while maintaining string stability and platooning constraints at the same time. The authors in "Integrated cooperative adaptive cruise and variable speed limit controls for reducing rear-end collision risks near freeway bottlenecks based on micro-simulations" presented a strategy to reduce the risk of rear-end collisions. The evaluation of the simulation of the proposed strategy demonstrated that it had effectively achieved its goal, with a 98% decline of time exposed time-to-collision and time integrated time-to-collision and a 33% decrease in the average travel time. The authors in "Eco-cooperative adaptive cruise control at signalized intersections considering queue effects" proposed an algorithm to enhance the vehicle fuel efficiency by calculating the vehicle trajectory through a signalized intersection. The proposed algorithm achieved its objective by producing vehicle fuel savings of up to 40%. The authors in "Reinforcement-learning-based cooperative adaptive cruise control of buses in the Lincoln tunnel corridor with time-varying topology" developed an algorithm that aims to minimize a cost function for connected and autonomous buses by employing the reinforcement learning technique. The results showed that the algorithm ensures the stability of the connected bus systems resulting in smooth traffic flow and shorter travel time.

In the area of cooperative speed limit control, Wang et al. and Greguric et al. demonstrated work related to Cooperative Speed Limit Control using V2I and V2X communications. See C. Wang, J. Zhang, L. Xu, L. Li, and B. Ran, "A new solution for freeway congestion: Cooperative speed limit control using distributed reinforcement learning," *IEEE Access*, vol. 7, pp. 41947-41957, 2019; and M. Greguric, S. Mandzuka, and M. Sostaric, "The application of cooperative variable speed limit control for reduction of crash potential," in *Proc. Int. Symp. ELMAR*, September 2019, pp. 1-4, each incorporated herein by reference in their entirety. Both research aimed to improve safety and produce better traffic flow performance. The authors in "A new solution for freeway congestion: Cooperative speed limit control using distributed reinforcement learning" compared their proposed system with no control conditions, and the proposed system could significantly reduce the total travel time and the outflow bottleneck.

In the area of cooperative parking, the authors in "Cooperative parking search: Reducing travel time by information exchange among searching vehicles" and "Investigating vehicle-to-vehicle communication for cooperative car parking: The copark approach" investigated the benefits of the cooperative parking approach to traffic congestion and the waste of time to find ideal parking through the exchange of information between vehicles. See M. Rybarsch et al., "Cooperative parking search: Reducing travel time by information exchange among searching vehicles," in *Proc. IEEE 20th Int. Conf. Intell. Transp. Syst. (ITSC)*, October 2017, pp. 1-6; and A. Aliedani, S. W. Loke, A. Desai, and P. Desai, "Investigating vehicle-to-vehicle communication for cooperative car parking: The copark approach," in *Proc. IEEE Int. Smart Cities Conf. (ISC2)*, September 2016, pp. 1-8, each incorporated herein by reference in their entirety. Both investigations reduced the searching time by 30% and 57%, respectively, compared to the non-cooperative approach.

In the area of cooperative traffic control: Chen and Chang proposed a cooperative traffic control framework that aims to optimize the global throughput and travel time of vehicles. See L. W. Chen and C. C. Chang, "Cooperative traffic control with green wave coordination for multiple intersections based on the Internet of Vehicles," *IEEE Trans. Syst., Man, Cybern. Syst.*, vol. 47, no. 7, pp. 1321-1335, July 2016, incorporated herein by reference in its entirety. The conducted simulation showed that the proposed framework achieved its goal by reaching high global throughput, and reducing the total travel time, as well as reducing the $CO_2$ emissions.

In Table I, a comparison of related work is summarized.

TABLE I

RELATED WORK SUMMARY

| Paper | Contribution | Connections | Application | Used Tools |
|---|---|---|---|---|
| [8] | Proposed health monitoring systems for drivers inside cars using Bluetooth. | V2I | Cooperative Health Emergency Response | Arduino microcontroller, Bluetooth WiFi, Wearables |
| [10] | Proposed real-time heart rate monitoring system to improve passenger health in driverless cars. | — | Cooperative Health Emergency Response | Pyton, OpenCV, Raspberry Pi 3 |
| [12] | Proposed an intelligent health monitoring system for connected cars to detect abnormalities and stroke initiation. | — | Cooperative Health Emergency Response | Biosensor, MapR-DB(HBase) |
| [13] | Proposed an implicit cooperative positioning algorithm by sharing information via V2V connection using onboard sensors. | V2V | Cooperative Positioning | SUMO |
| [15] | Proposed a cooperative positioning system (CNVPS) that quickly locates nearly vehicles based on information captured by sensors and shared over V2V communications. | V2V | Cooperative Positioning | Veins, SUMO, OMNet++ |
| [17] | Proposed a cooperative lane-change strategy to improve traffic operations in a divergent area near a V2V, V2Ihighway and off-ramp for CAVs. | V2V, V2I | Cooperative Lane Changing | MATLAB |
| [18] | Proposed a cooperative lane-change method that focuses on the multi-vehicle motion planning problem of CAVs. | V2V, V2I | Cooperative Lane Changing | AMPL |
| [20] | Proposed predictive platoon controllers for platoons' constraint handling to improve the overall energy economy. | V2V | Cooperative Cruise Control | Autonomie, MATLAB |

TABLE I-continued

RELATED WORK SUMMARY

| Paper | Contribution | Connections | Application | Used Tools |
|---|---|---|---|---|
| [21] | Proposed an integrated cooperative cruise control system and a vehicle speed strategy to reduce the risk of a rear collision near highway bottlenecks. | V2V, V2I | Cooperative Cruise Control | MATLAB |
| [24] | Proposed a variable speed limit control system under the V2I environment to increase highway traffic and safety. | V2I | Cooperative Speed Limit Control | MOTUS |
| [26] | Studied if cooperative searching while parking reduces search time and total travel time. | V2V | Cooperative Parking | SUMO |
| [27] | Studied a decentralized approach to an intelligent parking system that explores V2V connections benefits. | V2V | Cooperative Parking | JADE 1, SUMO, TraSMAPI |

It is one object of the present disclosure to describe a system and method that incorporates a framework that reduces the total time to receive first emergency treatment by an emergency treatment provider. The framework can use a federated intelligent health monitoring system to protect user privacy and provide information security. The framework can combine a cellular network and local area networks to provide wide accessibility. The system and method can include an in-vehicle process and an out-vehicle process.

SUMMARY

An aspect is a system for emergency health response, that can include a plurality of health monitoring devices including at least one sensor for measuring ECG, heart rate, skin color, motion, respiratory rate, and/or oxygen level of a user that is inside or proximate to a subject vehicle; a local machine learning device to predict abnormalities in a health status of the user that are indications of an impending emergency health condition based on measurements by the plurality of health monitoring devices; a communications device connected to the local machine learning device configured to transmit an emergency alert message to one or more of an emergency response vehicle and an stationary emergency health care facility that are within a communication range of the communications device, and for receiving response messages from an emergency response vehicle and a stationary emergency health care facility that are available to provide emergency treatment for an emergency health condition indicated in the emergency alert message; a health condition controller to select an emergency response vehicle and a stationary emergency health care facility, as a provider, from among the emergency response vehicles or the stationary emergency health care facilities that sent the response messages; wherein when the provider is a stationary emergency health care facility, the subject vehicle sets a destination to a provider health care facility and transmits, via the communications device, health status information of the user to the provider health care facility, and wherein when the provider is an emergency response vehicle, the subject vehicle communicates coordinates as a meeting destination for meeting a provider response vehicle, and transmit, via the communications device, the health status information of the user to the provider response vehicle.

A further aspect is a non-transitory computer readable storage medium storing computer program instructions, which when executed by processing circuitry, performs a method that can include measuring, via sensors, at least one of ECG, heart rate, skin color, motion, respiratory rate, oxygen level of a user that is inside or proximate to a subject vehicle; predicting, via a local machine learning device, an abnormality in health status of the user that are indications of impending an emergency health condition that is likely to occur based on the measurements by the sensors; transmitting, via a communications device, an emergency alert message to emergency response vehicles and stationary emergency health care facilities that are within range of the communications device, and receiving response messages from emergency response vehicles and stationary emergency health care facilities that are available to provide emergency treatment for an emergency health condition indicated in the emergency alert message; selecting, by a health condition controller, an emergency response vehicle or a stationary emergency health care facility, as a provider, from among the emergency response vehicles or the stationary emergency health care facilities that sent the response messages; wherein when the provider is a stationary emergency health care facility, the subject vehicle will set its destination to the provider health care facility and will transmit, via the communication device, health status information of the user to the provider health care facility, and wherein when the provider is an emergency response vehicle, the subject vehicle will communicate coordinates as a meeting destination for meeting the provider response vehicle, and will transmit, via the communication device, health status information of the user to the provider response vehicle.

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein:

FIG. 20A is a graph of long short-term memory model ROC, FIG. 20B is a graph of convolutional neural network ROC, FIG. 20C is a graph of multi-layer perceptron model ROC, FIG. 20D is a graph of support vector model ROC, FIG. 20E is a graph of logistic regression model ROC;

DETAILED DESCRIPTION

Figure 1:
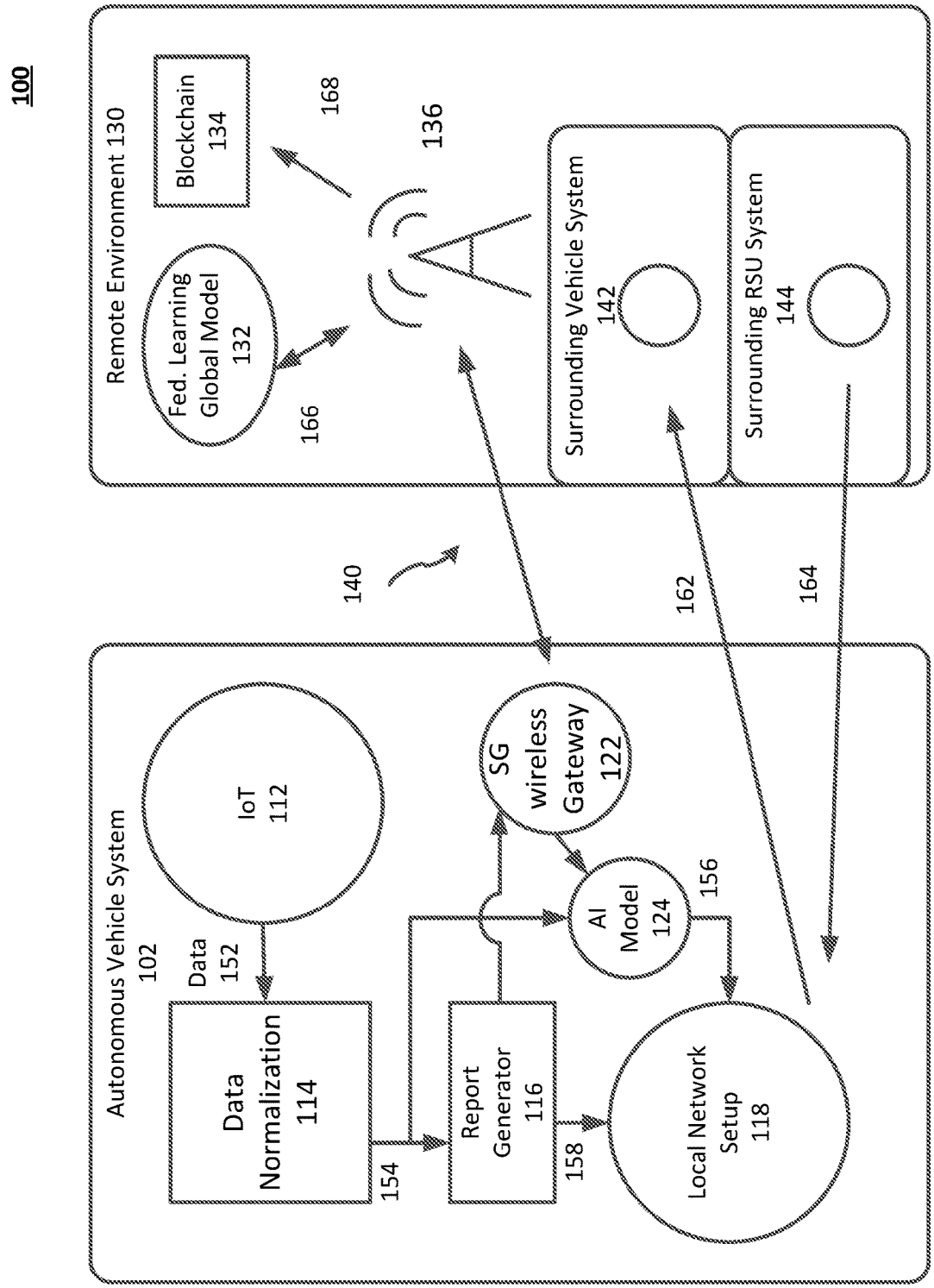
FIG. 1 is a block diagram of an in-vehicle architecture, in accordance with an exemplary aspect of the disclosure.

In the drawings, like reference numerals designate identical or corresponding parts throughout the several views. Further, as used herein, the words "a," "an" and the like generally carry a meaning of "one or more," unless stated otherwise. The drawings are generally drawn to scale unless specified otherwise or illustrating schematic structures or flowcharts.

Furthermore, the terms "approximately," "approximate," "about," and similar terms generally refer to ranges that include the identified value within a margin of 20%, 10%, or preferably 5%, and any values therebetween.

This disclosure relates to a Cooperative Health Intelligent Emergency Response System for autonomous vehicles (Avs) that allows the vehicle to act collaboratively with different Cooperative Intelligent Transport Systems (C-ITS) to respond to emergency alerts coming from an in-vehicle intelligent health monitoring system. The disclosure provides an advanced in-vehicle intelligent health monitoring system that employs federated learning to protect user privacy with wider accessibility. The disclosure provides a Cooperative Health Intelligent Emergency Response system that reduces the time for an individual suffering a health abnormality to receive emergency treatment. The disclosure provides a set of algorithms that implement a framework by applying deep federated learning and Vehicle-to-Many devices (V2X) connectivity. The disclosure provides a machine learning model that predicts an impending health issue. The disclosure provides a system and method that is optimized for the problem of selecting the best decision that minimizes the delay for a passenger suffering a health abnormality to get the treatment. The disclosure provides comprehensive experiments for both deep federated learning and vehicular networks to test and evaluate the system.

With the expected increase in the percentage of the population living in urban areas to about 60% of the global population by 2030, there has been an increasing interest in creating smart cities to improve the quality of life. According to forecasts, investments in smart cities are expected to reach $158 billion by 2022. A smart city employs information and communication technologies over connected objects in an urban area to improve its operations. This connected-objects arrangement uses wireless technologies to transmit data collected from citizens, buildings, devices, and vehicles through the IoT.

IoT has been integrated into today's lifestyle through connecting everything to almost everything, including smartphones, smart buildings, smart homes, as well as healthcare wearable devices. Moreover, IoT sensors and devices have contributed toward the improvement of healthcare systems by facilitating the health workflow, speeding up access to medical records, increasing the accuracy of collected data from different sources, sharing capabilities, as well as fighting pandemics. According to reports published by the U.S. Institute of Medicine that medical errors claiming the lives of 400,000 people each year due to issues related to data inefficiency. More specifically, it is the inability to access a patient's medical history, missed and delayed diagnoses, or corrupted health data that are often a proximal cause for such deaths. IoT technological advancements have significantly influenced the healthcare system in connecting it to the user's personal device which can capture, store, and notify health providers of the relevant health data in real time and thereby increase effective health support and reduce the mortality rate.

Autonomous Vehicles (AVs) are another key technology that plays a game-changing role in smart cities and intelligent transportation systems. An AV is a vehicle that can drive itself without human intervention or control by sensing its environments. AVs are equipped with IoT devices, sensors, and machine learning capabilities to operate safely on the roads with functions such as, auto cruise control, blind-spot detection, lane departure detection, lane keep assist, parking assist, automatic braking, etc.

Using IoT devices, AVs can be connected to anything in vehicle-to-everything (V2X) related, including vehicle-to-network (V2N), vehicle-to-vehicle (V2V), vehicle-to-infrastructure (V2I), vehicle-to-pedestrian (V2P), vehicle-to-cloud (V2C), and vehicle-to-device (V2D). These different forms of communications enable all elements to coordinate their actions by interacting together through the sharing of information, and this is the domain of Cooperative Intelligent Transport Systems (C-ITS). *See Cooperative, Connected and Automated Mobility (CCAM)*. Accessed: Apr. 20, 2021. [Online]. Available: ec.europa.eu/transport/themes/its/c-its_en, incorporated herein by reference in its entirety.

C-ITS aims to improve road safety, traffic efficiency, provide driving comfort, reduce fuel and energy consumptions, reduce harmful emissions, reduce travel time, adapt to different situations, and facilitate transportation access for people with disabilities and the elderly, etc.

While the AV in C-ITS can monitor itself and the surrounding environment and communicate with other elements of the intelligent transportation systems at the same time, in some embodiments, the AV can also monitor and communicate with passengers inside the vehicle through IoT devices integrated into the AV system. The monitoring and communication aim to enable the vehicle to assist the passengers and meet their needs.

A passenger health monitoring system is an important application for ITS as the vehicle will be aware of the passenger's health condition, and can react according to it to save driver's life. In Germany, a study found that around 24% of highway accidents are caused by fatigue. To migrate to C-ITS from ITS, the vehicle communicates with other elements of the ITS which includes other vehicles and roadside units (RSUs) in V2V and V2I connections to better handle the situation and increase the chances of saving the passenger's life by performing a Cooperative Health Emergency Response. Roadside units (RSUs) are non-mobile units, while vehicles are mobile. In AVs, data collected from health monitoring IoT devices embedded in the system such as ECG, heart rate, skin color, motion, respiratory rate, oxygen levels, and other data that can be used in an Artificial Intelligence (AI) model. Provided such data, the AI model can be trained to predict combinations of abnormalities in the passenger's health status that indicate an impending health emergency condition. Conditions such as fatigue, shock, losing consciousness, heart attacks, heart failure, shortness of breath, or even brain damage, are predicted using the AI model, and subsequently send alerts so that the vehicle can respond to save the passenger's life.

There is a need for a system and method for cooperative vehicle behavior in health emergencies. The present disclosure is directed to a system and method for cooperative response for AVs when drivers and/or passengers have abnormal health conditions that indicate an impending emergency health issue. This approach not only deals with monitoring the passenger's health status, but also deals with the vehicle's interaction with the surrounding environment through V2V and V2I connections to respond to the driver's and/or passenger's impending health issue.

An object is to reduce the total time to receive the first emergency treatment by an emergency treatment provider. Embodiments use a federated intelligent health monitoring system to protect user privacy and provide information security with wider accessibility, by adopting 5G cellular networks and local area networks. Embodiments include two phases: the first phase is the in-vehicle phase, and the second is the out-vehicle phase. Although the in-vehicle phase is described as occurring before the out-vehicle phase, embodiments include concurrent operation of the in-vehicle phase and the out-vehicle phase, allowing for much of the functions of the out-vehicle phase to be previously performed as needed when an alert is broadcast.

In-Vehicle Phase

FIG. 1 is a block diagram of an in-vehicle architecture, in accordance with an exemplary aspect of the disclosure. In some embodiments, the in-vehicle phase 100 utilizes a federated intelligent health monitoring system that monitors the passenger's healthcare status. Note that, for purposes of this disclosure, a passenger may include a driver as well as a passenger of a vehicle, and thus, driver and passenger may be used interchangeably. Also note that a vehicle is not limited to transporting a single passenger, but can transport more than a single passenger. Moreover, the in-vehicle phase 100 includes storage of the passenger health status reports in a secure database with limited access for involved parties only. The in-vehicle phase 100 employs IoT devices and sensors to monitor the passengers' body metrics such as blood pressure, electrocardiogram, facial expression, movement, oxygen levels, and more. As shown in FIG. 1, the data captured by IoT devices and sensors 112 in an Autonomous Vehicle (AV) System 102 are used in generating healthcare status reports 116, and are used by a machine learning (or AI) model 124 that detects abnormal patterns in the healthcare status of the passenger. The data will be normalized before being used by the intelligent model 124 as it enters the data normalization stage 114 to be cleaned and pre-processed. If the prediction process indicates an impending abnormal health condition, the machine learning model 124 will send alerts to the vehicle network system 118 to prepare for the next phase of the system.

In some embodiments, some operations of the in-vehicle phase of the autonomous vehicle system 102 may be included in a mobile application that is performed in a portable mobile device, such as a smartphone, tablet computer, a wearable computing device, to name a few. In particular, operations including a data normalization 114, report generator 116, and a machine learning model 124 can be included in a mobile application (App). The computer program for the App may be stored in a computer readable storage medium, such as a flash drive or other non-volatile memory device. The portable mobile device may be configured with a wireless gateway 122, as well as include short-range wireless communication for communication with an in-vehicle network 118 and Internet of Things (IoT) sensor devices 112.

In some embodiments, the machine learning model 124 is a local model that is part of the Federated Learning process. A Federated Learning process is a process of training many substantially equivalent machine learning models where local machine learning models train with local training data and each local machine learning model periodically shares its local parameters with a global machine learning model. The global machine learning model updates its parameters using the local parameters, then broadcasts the updated parameters back to the local machine learning models. The term federated comes from the use of a global machine learning model as the guiding parameters for the local machine learning models. The training data itself is kept secure with the local machine learning model. Any global training data is kept secure with the global machine learning model. In order to update a local machine learning model 124 continuously and make use of the data captured by the devices 112, the machine learning model 124 preferably goes through the following steps 1) Conduct a local training process using the captured data.
2) The model updates sent to a cloud service 130 that has a global model 132 through a cellular network 140 that includes a wireless gateway 122 inside the vehicle 102 connected to a wireless base station 136. In some embodiments, the cellular network may be any wireless communications network, including, but not limited to, 3G, 4G, 5G, 6G.
3) The cloud service 130 receives such updates from different vehicles registered with this service.
4) The updates are aggregated and used to train the global model 132.
5) The global model 132 is shared again with the vehicles so that the vehicles can use a more up-to-date model and the process continues.

Moreover, the reports generated by the Vehicle System's Report Generator 116 will be sent to other vehicles 142 and road side units (RSUs) 144 in case of an emergency through V2V and V2I communications, and will also be stored in a cloud service 130, secure, and distributed blockchain 134 through the cellular network 140 to allow the passenger's healthcare professionals access these reports at any time and be aware of the passenger's case and health history. The purpose of using a blockchain database 134 is to provide information security for the user and protect the sensitive data from cyber-attacks and manipulations.

Out-Vehicle Phase

Figure 2:
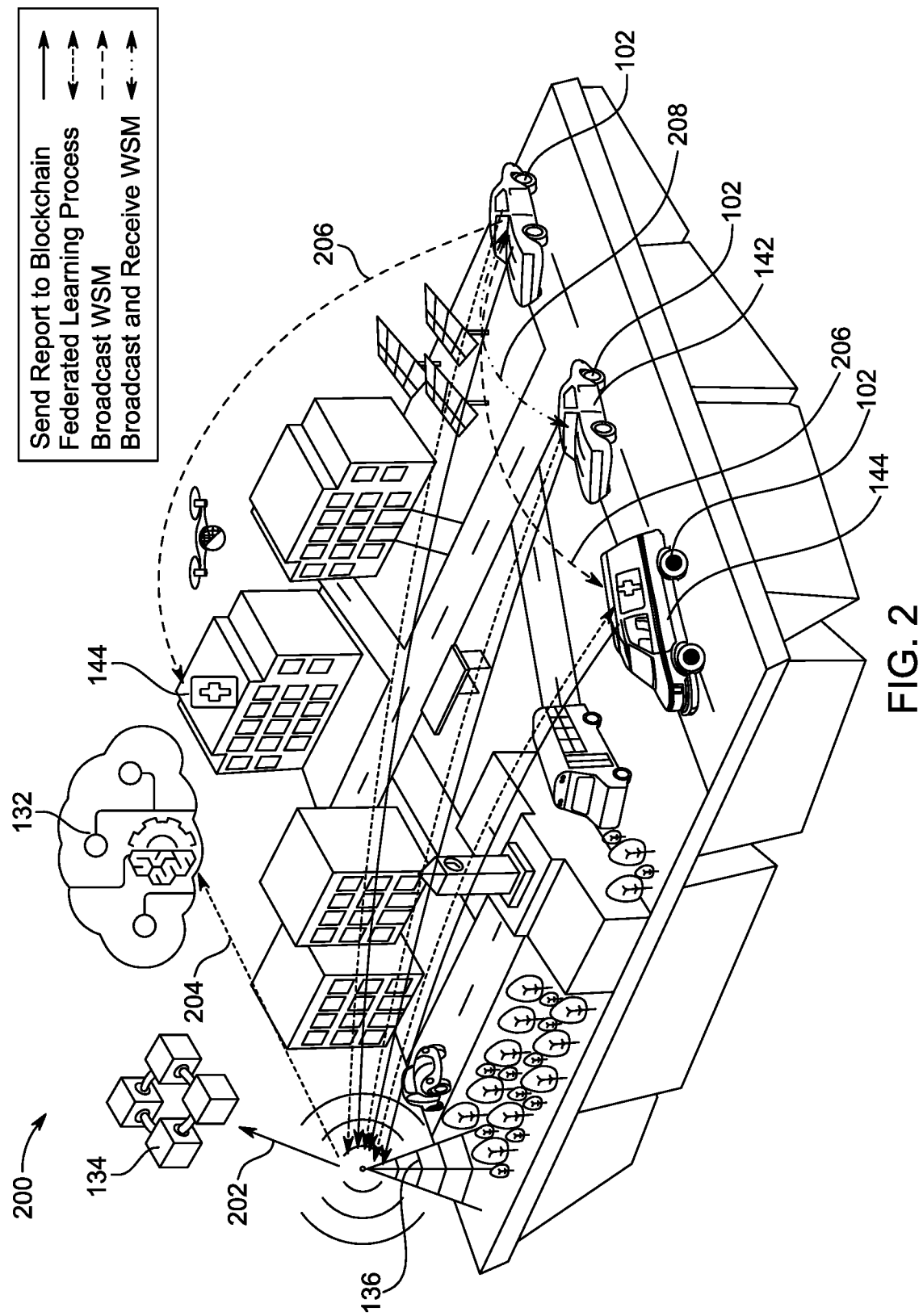
FIG. 2 illustrates an out-vehicle system, in accordance with an exemplary aspect of the disclosure.

FIG. 2 illustrates an out-vehicle system, in accordance with an exemplary aspect of the disclosure. As mentioned above, in some embodiments, operations of the out-vehicle phase 200 may be performed concurrently with the in-vehicle phase 100, such that some operations of the out-vehicle phase 200 may be completed before a health alert is broadcast. In an embodiment, the out-vehicle phase 200 will begin with the abnormal health alert. Then, the following steps will be performed 1) The vehicle 102 sends an emergency message to all surrounding vehicles 142 and RSUs. 144.
2) All vehicles 142 and RSUs 144 receive this message, but only vehicles and RSUs that can provide emergency treatment to respond to the emergency message.
3) The vehicle 102 that has the emergency case chooses the closest emergency provider from the list of emergency treatment providers who sent their consent for help.
4) The vehicle 102 arranges with the emergency provider (142, 144) regarding the treatment receiving process. If it is a vehicle 142, both vehicles 102 and 142 schedule parking in the nearest parking area. Otherwise, the emergency provider is the RSU 144, and thus, the vehicle 102 changes direction to the RSU 144 position, so that the passenger receives treatment there.
5) After the vehicle 102 selects the closest emergency treatment provider, it sends 202 the passenger's health status report to the treatment provider to assess the case prior to arrival.

Framework

To lay out the foundation of the analysis of formulating the cooperative intelligent transportation system, the following terms are defined;

The decision variables $$a_j^i = \begin{cases} 1, \text{ if vehicle } i \text{ is selected to go to hosptial } j \\ 0, \text{ Otherwise} \end{cases} \quad (1)$$

The set of available hospitals $$\mathcal{M} = \{1, 2, 3, \ldots, M\}, \quad (2)$$

The set of available vehicles $$\mathcal{N} = \{1, 2, 3, \ldots, N\}, \quad (3)$$

An objective is to select the best decision that minimizes the delay to get the treatment. This objective can be expressed as:

$$\min_{a_j^i \in \{0,1\}} T = \sum_i^M \sum_j^N \left( \frac{d_j^i}{S_j^i} + D_j^i \right) a_j^i \text{ s.t. } \sum_i^M \sum_j^N a_j^i = 1 \quad (4)$$

Note that $D_j^i$, $d_j^i$, and $S_j^i$ are hospital i and vehicle j, having dependencies that are represented respectively:
1) $D_j^i$ is other delay dependent of hospital and car (response time, waiting time, and others).
2) $S_j^i$ is the estimated speed of car j to hospital i.
3) $d_j^i$ is the travel distance by car j to hospital i.

The formulation is a Bilevel Linear Programming problem (BLP) that can be written in a standard matrix form as:

$$\begin{cases} \min C^T X \\ \text{s.t. } AX = b \\ X \in 0, 1 \end{cases} \quad (5)$$

$$C = \left[ \frac{d_1^1}{S_1^1} + D_1^1 \frac{d_2^2}{S_2^2} + D_2^2 \ldots \frac{d_N^M}{S_N^M} + D_N^M \right]_{1 \times (N \times M)}$$

$$A = [111 \ldots 1]_{1 \times (N \times M)}$$

$$b = [1]$$

The system optimization is a BLP, which is nondeterministic polynomial-time (NP-hard) in general methods. However, the special structure of the problem reveals that it constitutes a uni-modular optimization, in which the optimal solution lies on the vertex of the optimization space, hence, Linear programming (LP) methods can be used to find the optimal solution in a polynomial time.

C-Healthier Algorithm Implementation

The Cooperative Health Intelligent Emergency Response (also referred to as C-HEALTHIER) consists of two parts: in-vehicle (FIG. 1) and out-vehicle (FIG. 2). The in-vehicle is a federated intelligent health monitoring system and the vehicle's reaction to the emergency alert. At the same time, the out-vehicle is the cooperative behavior between the vehicle, and the surrounding vehicles and RSUs.

Figure 3:
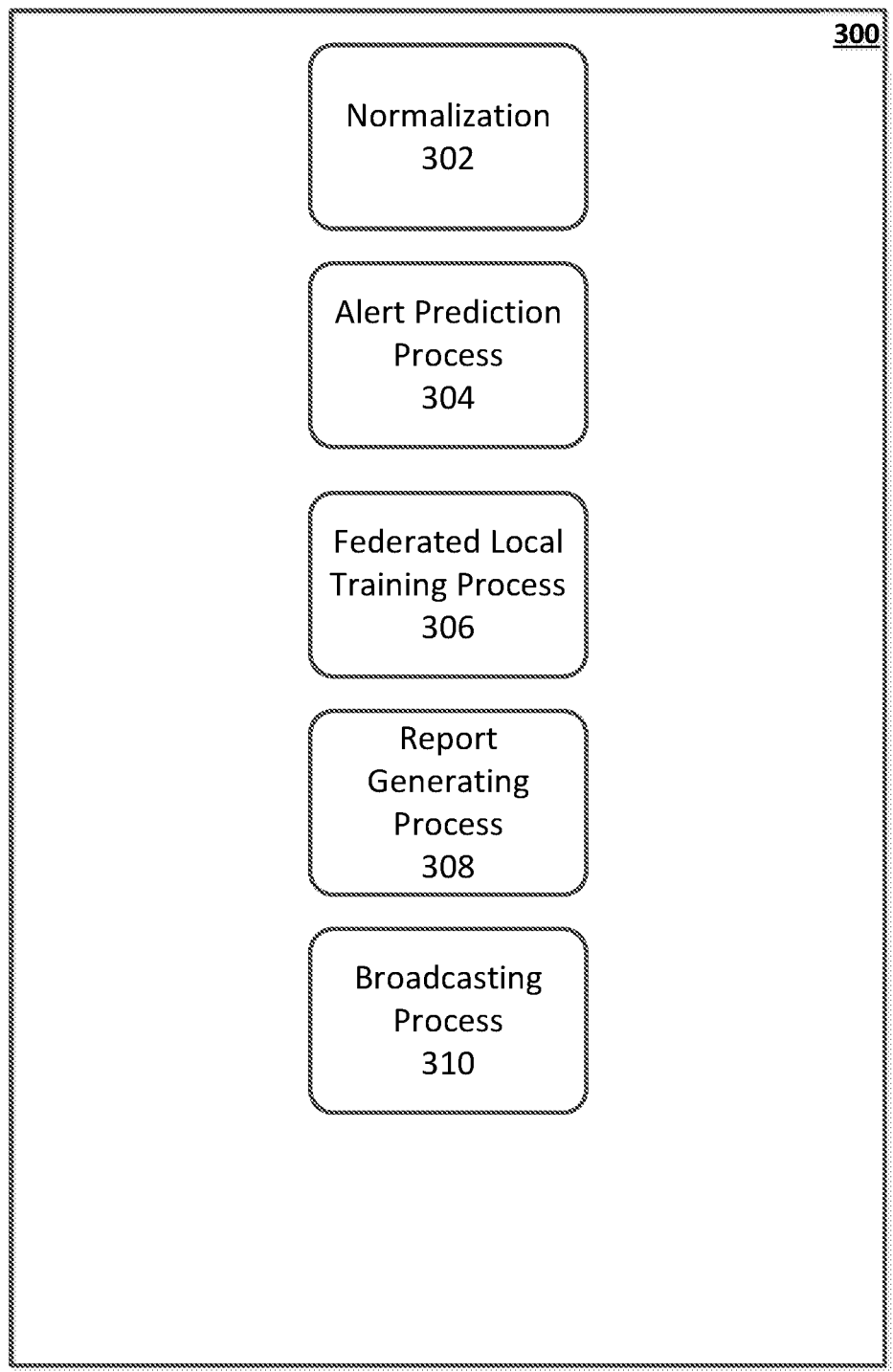
FIG. 3 is a block diagram of a federated intelligent health monitoring system, in accordance with an exemplary aspect of the disclosure.

FIG. 3 is a block diagram of a federated intelligent health monitoring system, in accordance with an exemplary aspect of the disclosure. The Federated Intelligent Health Monitoring System includes 5 processes: Normalization process 302, Alert prediction process 304, local training process 306, Report generating process 308, and the Broadcasting process 310. First, data 152 captured by IoT devices 112 are normalized 302 then the normalized data 154 are used by the local machine learning model 124 to predict health abnormalities and subsequently send emergency alerts 156. Also, the normalized data 154 are used as training data by the same local model 124, where the local model 124 gets new weights to be broadcast to the global model 132 and used there.

---

Algorithm 1 Federated Intelligent Health Monitoring System

---

Input: D = Data Captured
Output: Alert, mw, report, Process Success: S
1 ND = Normalized data,
2 mw = model weights.
3 lr = learning rate
4 function Normalization process( )
5 | for record ∈ D do
6 | | ND = normalizer(record)
7 | end
8 end
9 function Alert Prediction Process( )
10 | for record ∈ ND do
11 | | label = local_model(record)
12 | | if (label ! = 0) then
13 | | | return Alert
14 | | end
15 | end
16 end
17 function Federated Local Training Process( )
18 | for record ∈ ND do
19 | | mw ← mw × −lr × Δ loss(mw, record)
20 | end
21 | return mw
22 end
23 function Report Generating Process( )
24 | for record ∈ ND do
25 | | report = report_generator(record)
26 | end
27 | return report
28 end
29 function Broadcasting Process( )

30 | mw $\xrightarrow{broadcast}$ Cloud Server

31 | report $\xrightarrow{broadcast}$ Blockchain

32 | return S
33 end

---

Moreover, the normalized data 154 are used by the report generator 116 to generate a health status report 158 that is sent to the emergency treatment provider and broadcast to the blockchain database 134 to be stored there and become accessible for the respective health professionals.

Figure 4:
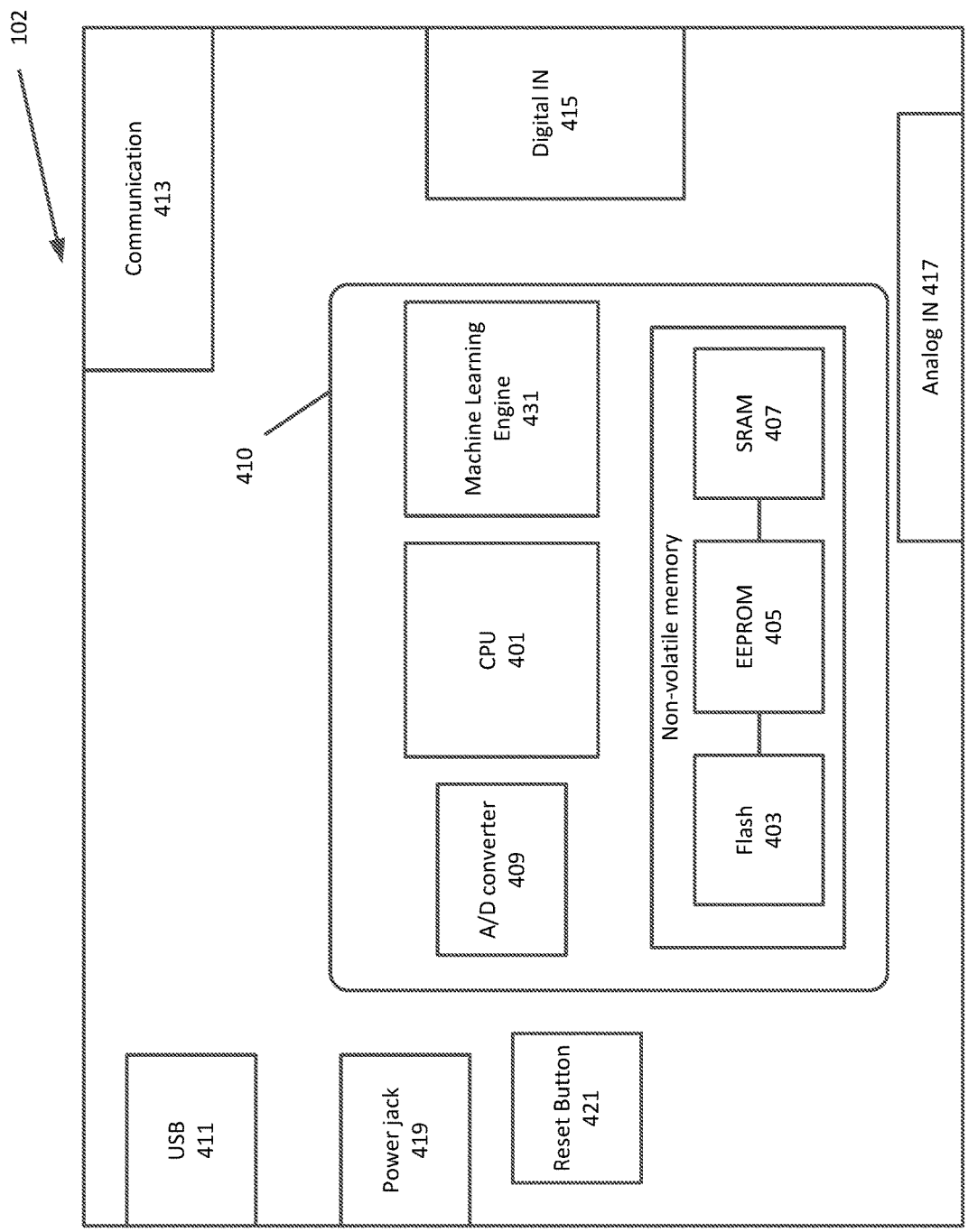
FIG. 4 is a block diagram for an in-vehicle controller.

FIG. 4 is a block diagram for an in-vehicle controller.

The computer-based control system 102 may be based on a microcontroller as the in-vehicle controller. A microcontroller may contain one or more processor cores (CPUs) along with memory (volatile and non-volatile) and programmable input/output peripherals. Program memory in the form of flash, ROM, EPROM, or EEPROM is often included on chip, as well as a secondary RAM for data storage. In one embodiment, the computer-based system 102 is an integrated circuit board 102 with a microcontroller 410. The board includes digital I/O pins 415, analog inputs 417, hardware serial ports 413, a USB connection 411, a power jack 419, and a reset button 421. Although a microcontroller-based board 102 is shown in FIG. 4, it should be understood that other microcontroller configurations are possible. Variations can include the number of pins, whether or not the board includes communication ports or a reset button. Microcontrollers vary based on the number of processing cores, size of non-volatile memory, the size of data memory, as well as whether or not it includes an A/D converter or D/A converter.

The microcontroller 410 is a RISC-based microcontroller having flash memory 403, SRAM 407, EEPROM 405, general purpose I/O lines, general purpose registers, a real time counter flexible timer/counters, a A/D converter 409, and a JTAG interface for on-chip debugging. The microcontroller is a single SOC. The recommended input voltage is between 7-12V.

In some embodiments, the microcontroller 410 includes a machine learning engine 431 for performing training and inference processing for a machine learning model.

Figure 5:
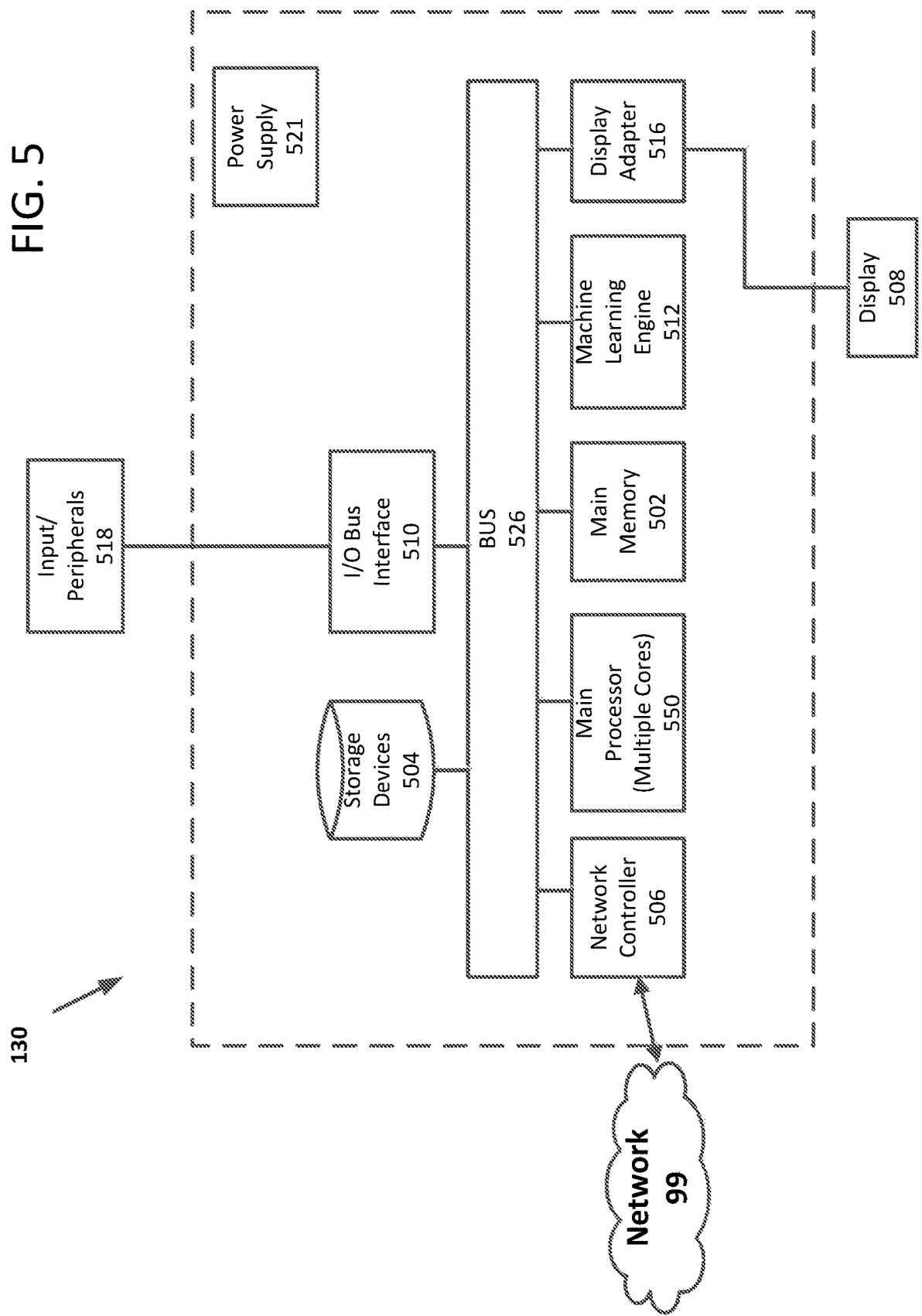
FIG. 5 is a block diagram of an out-vehicle server.

FIG. 5 is a block diagram of an out-vehicle server. FIG. 5 is a block diagram illustrating an example computer system for implementing the machine learning training and inference methods according to an exemplary aspect of the disclosure. The computer system may be an AI workstation running a server operating system, for example Ubuntu Linux OS, Windows Server, a version of Unix OS, or Mac OS Server. The computer system 500 may include one or more central processing units (CPU) 550 having multiple cores. The computer system 500 may include a graphics board 512 having multiple GPUs, each GPU having GPU memory. The graphics board 512 may perform many of the mathematical operations of the disclosed machine learning methods. The computer system 500 includes main memory 502, typically random access memory RAM, which contains the software being executed by the processing cores 550 and GPUs 512, as well as a non-volatile storage device 504 for storing data and the software programs. Several interfaces for interacting with the computer system 500 may be provided, including an I/O Bus Interface 510, Input/Peripherals 518 such as a keyboard, touch pad, mouse, Display Adapter 516 and one or more Displays 508, and a Network Controller 506 to enable wired or wireless communication through a network 99. The interfaces, memory and processors may communicate over the system bus 526. The computer system 500 includes a power supply 521, which may be a redundant power supply.

In some embodiments, the computer system 500 may include a server CPU and a graphics card, in which the GPUs have multiple cores. In some embodiments, the computer system 500 may include a machine learning engine 512.

Figure 6:
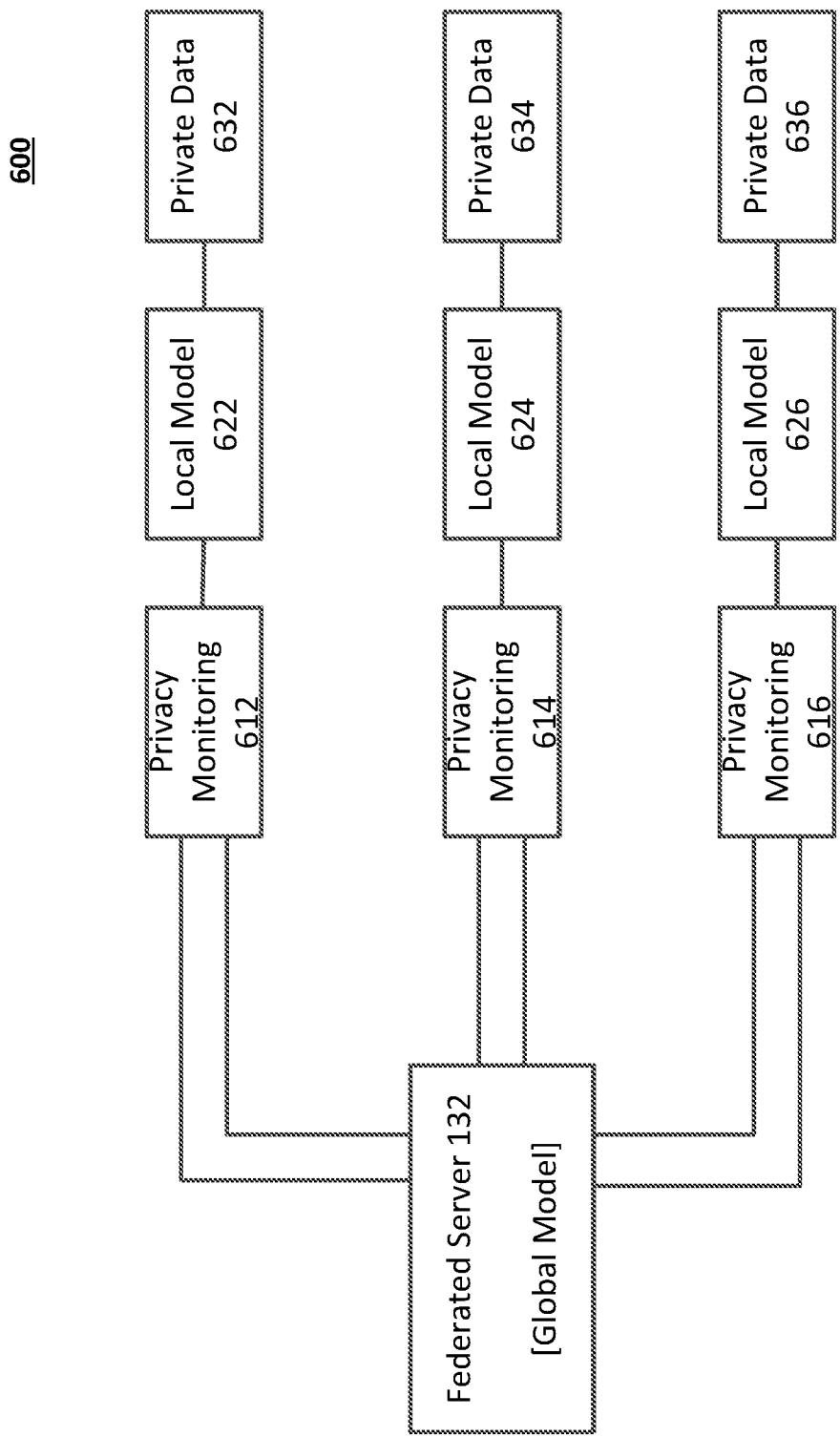
FIG. 6 is a block diagram for a federated learning system.

FIG. 6 is a block diagram for a federated learning system.

Vehicles 102 can build their own local machine learning model (622, 624, 626) to help automatically predict an emergency medical condition. However, a vehicle 102 by itself will typically not have sufficient number of training examples to train a deep learning network. Also, the training data involving medical information about a passenger may include private information. The federated learning system enables use of a larger number of training examples while keeping individual training examples in a secure storage. Only network parameters are shared. In the federated machine learning system, a centralized server maintains a global deep neural network 132 and each participating hospital 144 or other vehicle 142 would be given a copy of network parameters in order to train on their own dataset.

In particular, once the local machine learning model has been trained locally for a small number of iterations, for example five iterations, the participants send their updated version of the network parameters back to the centralized server 130 and keep their dataset within their own secure infrastructure. Each vehicle includes its own privacy monitoring 612, 614, 616, and others. Each vehicle includes its own secure private data storage 632, 634, 636.

The central server 130 then aggregates the contributions from all of the participants 124. In order to maintain security, only the updated network parameters are then shared with the participating vehicles, so that they will continue local training.

Local Training Process

Personal health monitoring devices in the form of mobile applications or built-in sensors can actively monitor a user's vital health parameters, such as the electrocardiogram (ECG), blood pressure, heart rate, and the sugar level which reduces the potential errors of data recording. These devices can capture and transfer data anonymously to the cloud and compare it with historical data for symptoms of any illness or notify the appropriate health personnel (doctor, nurse, or health agent). Fewer errors mean better performance, cost, efficiency, and improvements in healthcare services where an error can literally be the difference between life and death. This intelligent context-aware IoT health era is made possible by the convergence of technology and healthcare. See X. Zhou, W. Liang, K. I. K. Wang, H. Wang, L. T. Yang, and Q. Jin, "Deep-learning-enhanced human activity recognition for Internet of healthcare things," *IEEE Internet Things J.*, vol. 7, no. 7, pp. 6429-6438, July 2020, incorporated herein by reference in its entirety. In turn, this convergence in technology can improve the quality of life and solve many challenges such as information sharing, diagnoses inefficiency, monitoring cost reduction, operations optimization, medication errors, etc.

Digital twin (DT) technology refers to a digital replica of the physical object. DT combines artificial intelligence (AI), data analytics, IoT, and virtual and augmented reality paired with digital and physical objects. See I. Al Ridhawi, S. Otoum, M. Aloqaily, and A. Boukerche, "Generalizing AI: Challenges and opportunities for plug and play AI solutions," *IEEE Netw.*, early access, Sep. 30, 2020, doi: 10.1109/MNET.011.2000371, incorporated herein by reference in its entirety. This integration allows real-time data analysis, status monitoring, risk management, cost reduction, and future opportunities prediction.

For healthcare systems, having a virtual replica of a patient could be an optimal solution for health promotion, increase control over health, and improve healthcare operations. DT can be integrating with healthcare to improve its processes and those of corresponding intelligent IoT healthcare systems that use the DT framework. The framework employs a real-time data set. This framework combines IoT, data analytics, and machine learning to make the patients' virtual replica a reality, give the healthcare professionals more capabilities to control and enhance a patient's health, and take in the cooperation of patients with similar cases into the process to utilize real-life scenarios. The framework comprises three phases:

1) processing and prediction phase;
2) monitoring and correction phase;
3) comparison phase.

Each phase is responsible for improving an aspect of healthcare operations, the patient's aspect, the healthcare professional's aspect, or other patients with similar cases.

Toward this objective, an ECG classifier diagnoses heart disease and detects heart problems. The machine learning classifier is trained using real-time data of ECG rhythms collected from different patients through sensing electrodes. The collected results are.

A. Framework Phases

Figure 7:
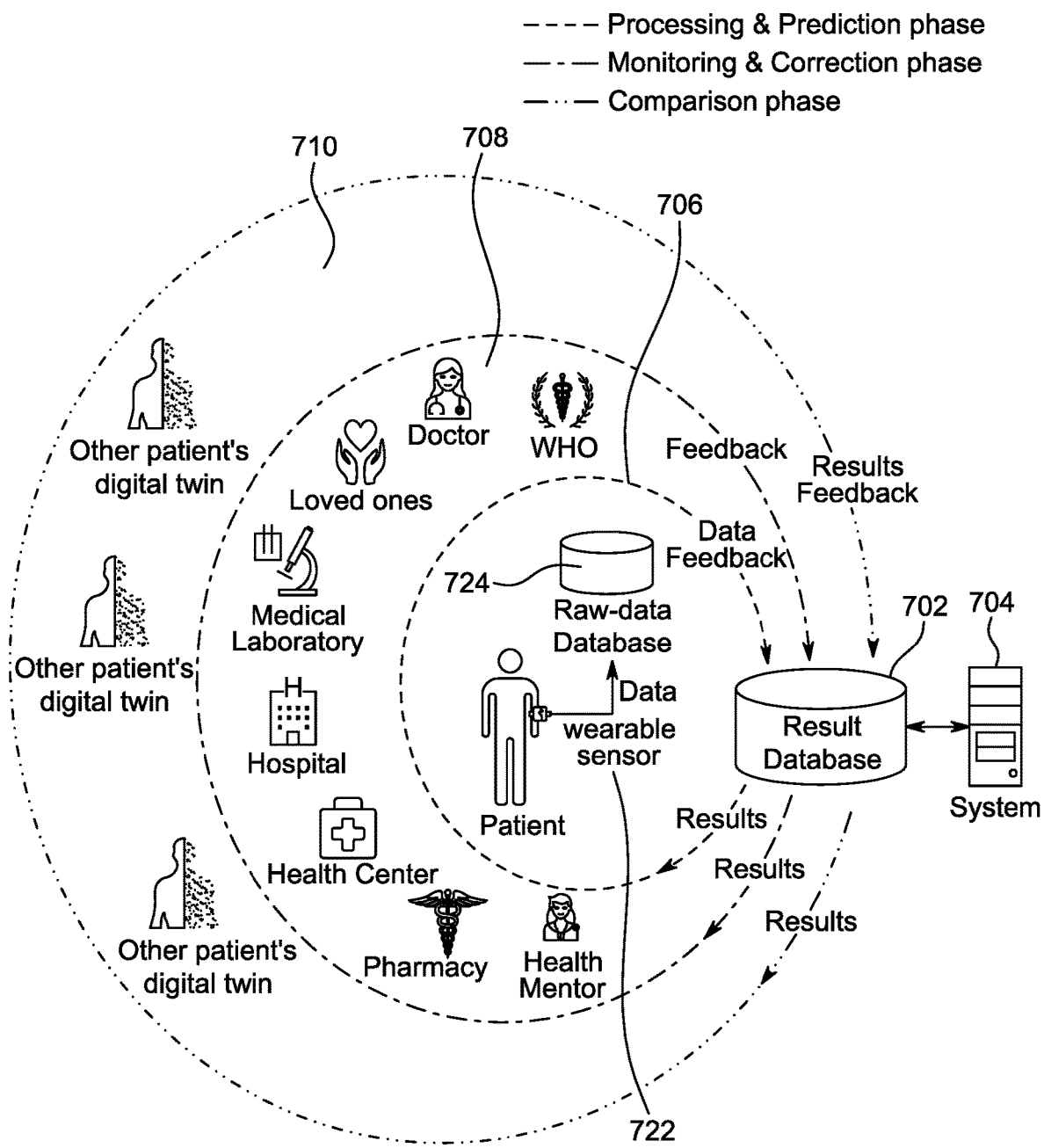
FIG. 7 illustrates a digital twin framework, in accordance with an exemplary aspect of the disclosure.

FIG. 7 illustrates a digital twin framework, in accordance with an exemplary aspect of the disclosure. As illustrated in the framework overview shown in FIG. 7, the framework is threefold: Processing and Prediction Phase 706, Monitoring and Correction Phase 708, Comparison Phase 710.

Processing and Prediction Phase: The processing and prediction phase 706 is patient-centered and begins with capturing the patient data using IoT wearable sensors 722. These sensors 722 transfer real-time data of human body metrics that are important to monitor the health status and help in detection of anomalies. The transferred data is stored temporarily in a cloud database 724 responsible for raw-data storage. This data is used by a machine learning system in the training and prediction process. Through data analytics and machine learning capabilities, the DT framework builds classifiers and predictive models that detect health anomalies that are indications of an impending emergency health condition that is likely to occur using the raw-data after cleansing, preprocessing, and representation. The machine learning model results are stored in another scalable, secure, and immutable cloud database called the result database 702. The result database 702 is accessible by the patient and the other framework phases' components for continuous feedback, correction, and model optimization.

Monitoring and Correction Phase: The monitoring and correction phase 708 requires intervention from the healthcare professionals from the patient domain. Healthcare professionals who provide treatments and advice based on formal training and experience use the results of the predictive models from the result database. This is along with clinical diagnosis and monitoring of the patient's health status to improve healthcare. By continuously feeding the predictive models with real-time data that help in detecting the body metrics anomalies, proactive monitoring and identification of impending emergency health issues is accomplished before they occur. Thus permitting the identification of the right treatments and helping healthcare professionals to design a better lifestyle for the patient. The professionals can correct, verify the results, and give informative feedback besides the read permissions of the result database, thus optimizing the model.

Comparison Phase: The comparison phase 710 is the cooperation of patients with similar cases takes place in the third phase to utilize real-life scenarios, enhance patients' Digital Twin (DT), and thereby enhance the whole framework. By obtaining data and results of DTs for similar cases and/or patients, the model is able to compare the current patient results with other patients. This process expands the predictive models' domain by having real-life scenarios with more reliable results to improve models' accuracy. It also gives healthcare professionals the ability to make more advanced and accurate decisions. Decisions not only based on real-time data monitoring but also those that rely on past, present, and predicted future events for other patients, so that they can simulate, modify, or avoid other patients' experiences.

System Implementation

The DT includes an ECG classifier that diagnoses heart disease and detects heart problems. The ECG classifier can be implemented as a deep learning model or using other machine learning models. In a preferred embodiment, the architecture and training method for the ECG classifier was chosen based on a performance evaluation comparison of five implemented models with different deep learning and traditional machine learning algorithms. Training of the ECG classifier may be performed offline using a real time training dataset, while inference operation may be performed in the cooperative health intelligent emergency response system during operation.

The DT may be incorporated as part of the cooperative health intelligent emergency response system (also referred to herein as C-HealthIER system), which is implemented as a cooperative intelligent transport system (also referred to as C-ITS) (See FIGS. 1 and 2). In some embodiments, the C-ITS involves a vehicle 102, also referred to as the emergency vehicle, that requires an emergency response by way of an alert, one or more other vehicles 142 that can provide emergency response services, such as an ambulance, and a hospital or other stationary medical facility 144 that can provide a response to emergency health-related conditions. Other stationary medical facilities can include express/emergency medical facilities.

The emergency vehicle 102 may transport a driver as well as one or more passengers. The emergency vehicle 102 may be one of a range of autonomous vehicle configurations. Six levels of driving automation have been defined including: Level 0, no driving automation; Level 1, driver assistance; Level 2, partial driving automation; Level 3, conditional driving automation; Level 4, high driving automation; Level 5, full driving automation. Level 5 vehicles are able to go anywhere and do anything that an experienced human driver can do. Level 4 vehicles human have the option to manually override. Thus, in most autonomous vehicles the driver is in control of driving or at least must remain alert and ready to take control if the system is unable to execute the task. The emergency vehicle 102 may be equipped with an embedded controller 410 for controlling the vehicle according to emergency conditions, may be augmented with emergency control functions performed in a portable mobile device, such as a smartphone or tablet computer, or may be supplemented with an independent portable mobile device that provides emergency alert services as a device that is not connected to an emergency vehicle.

Sensors that provide sensor information to an emergency controller 410 may be sensors that are built into the emergency vehicle 102, may be health sensors worn by a driver or passenger, or may be a combination of vehicle built-in sensors and user wearable sensors. In this disclosure, the sensors are collectively referred to as Internet of Things (IoT) sensors 112.

In some embodiments, IoT wearable sensors 722 include smart watches, sensors that can be worn on the upper arm, sensors that can be worn around the waist, sensors in gloves, as well as sensors that are built into a vehicles, such as sensors that are built into the steering wheel of a vehicle.

In one embodiment, smartphone technologies may be used to obtain ECG data from a driver or passenger. A detector may be held by, or attached to, the user by at least two fingers, or strapped across the user's chest. The detector sends the data to the user's smartphone, where a mobile application records the data as an ECG.

In a similar manner, a smartwatch or other wearable device may detect and monitor a wearer's heart rate. Heart rate data may be stored in the smartwatch or wearable device for later transfer, or may be continuously transferred to a health condition controller 410. Examples of wearable device include gloves or special vests equipped with sensors.

A continuous glucose monitor (CGM) can be worn by a user and automatically checks blood sugar levels at timed intervals, for example, every five minutes. The CGM provides real-time data to a mobile application or health condition controller 410.

Figure 8A:
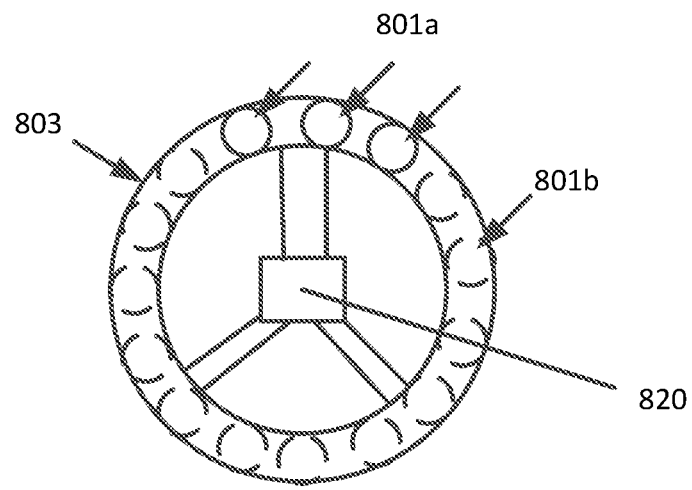
FIGS. 8A, 8B illustrate a steering wheel sensor arrangement, according to an exemplary aspect of the disclosure.
Figure 8B:
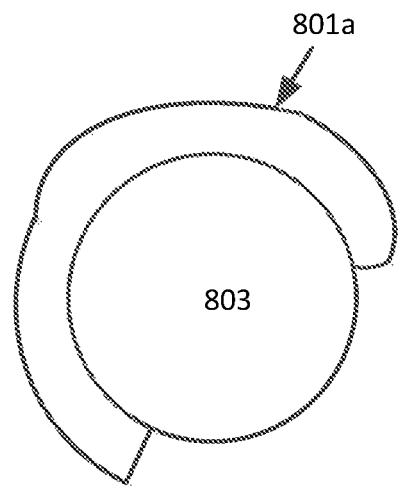

In one embodiment, as in FIG. 8A, sensors 801a, 801b for sensing heart rate and/or electrocardiogram (ECG) can be built into (or mounted on) the steering wheel 803 of a vehicle 102. The sensors 801a, 801b can be wired to a health condition controller 410 through a steering column 820. The sensors 801a, 801b are preferably capacitive sensors that detect touch. As shown in FIG. 8B, each of the sensors 801a, 801b for ECG or heart rate measurement may be substantially wrapped around the steering wheel in order to measure ECG by way of bending fingers to grip the steering wheel 803. The ECG/heart rate sensors are mounted equally spaced around a parameter of the steering wheel, in order to accommodate a continuous ECG/heart rate signal in a case that the steering wheel is rotated by repositioning of the hands.

In one embodiment, the ECG sensors include one ECG sensor 801a for placement of one finger of the user and a second ECG sensor 801b for placement of a second finger of the user, in order to obtain two ECG signals. The one ECG sensor 801a and the second ECG sensor 801b each have a width to accommodate one finger.

In some embodiments, an audio and/or visual display indication will be provided in order to inform a user that the ECG sensors 801a, 801b are measuring continuous ECG signals, or the sensors are not picking up heart rate or ECG signals. The audio and/or visual display indication may be provided by the vehicle display, such as an infotainment system, or may be generated by a mobile APP for output by the mobile device or transmitted for output by a vehicle display and audio output device.

Figure 9:
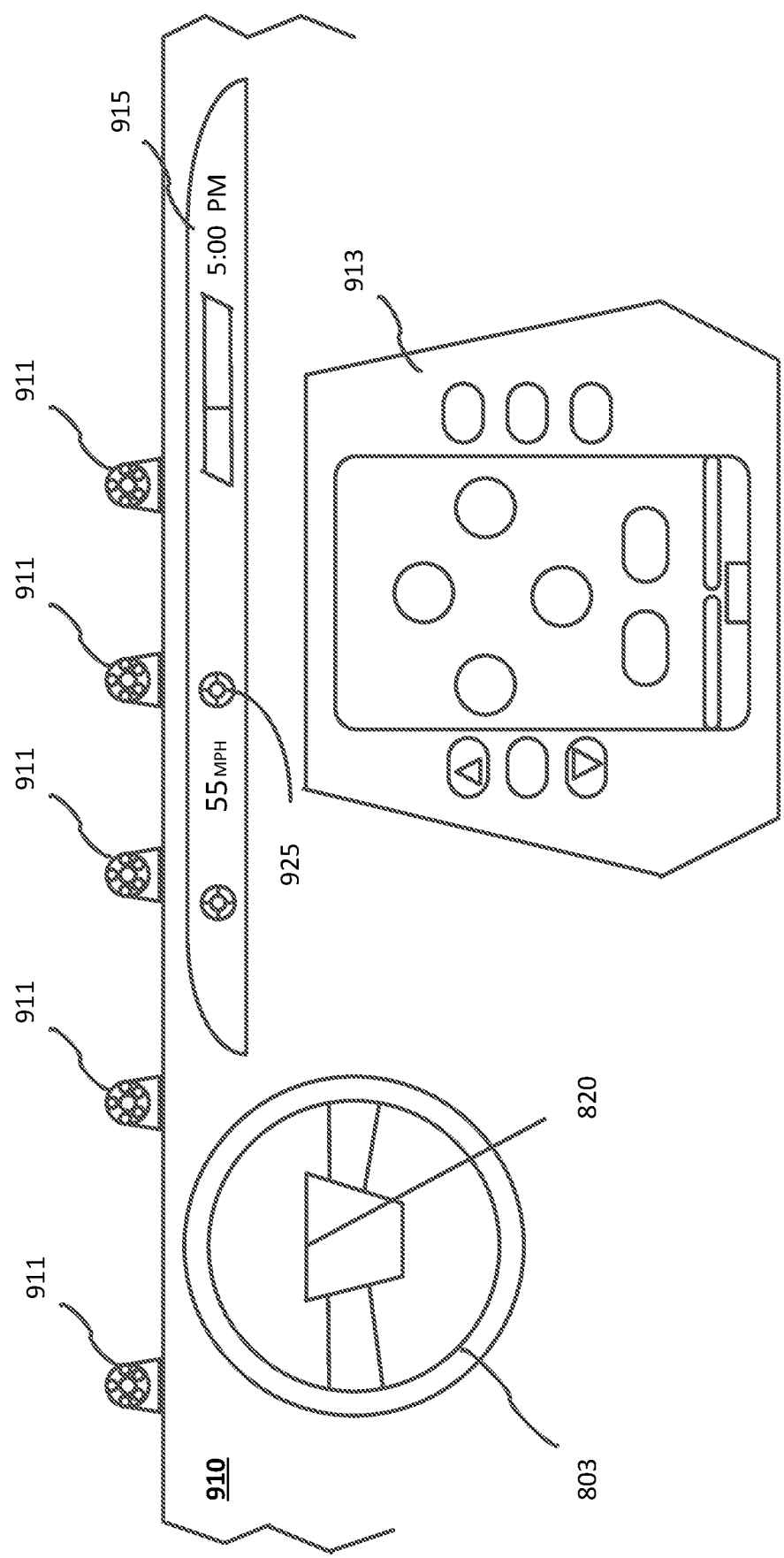
FIG. 9 illustrates a vehicle dashboard, according to an exemplary aspect of the disclosure.

In one embodiment, as in FIG. 9, one or more cameras 911, 925 can be mounted in the vehicle 102 cabin, such as in the vehicle dashboard 910, for monitoring the condition of the driver or a passenger. For example, the camera(s) 911, together with the image processing system associated with the camera can tract the driver's/passenger's eye movement and/or head position or movement in order to detect sleepiness or other reduced focus state. Display devices 913, 915 may be used to display messages to a driver or passenger, regarding health emergency conditions.

Figure 10:
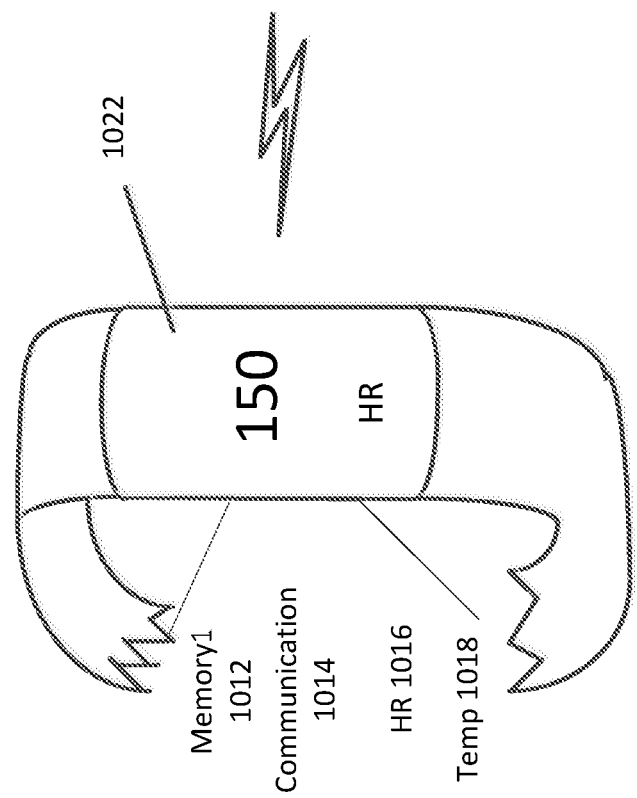
FIG. 10 illustrates a smartwatch as a sensor arrangement, in accordance with an exemplary aspect of the disclosure.

In one embodiment, as in FIG. 10, a smartwatch 1002 or other wearable sensor device may be used to monitor health data, including, but not limited to, ECG, heart rate 1016 and temperature 1018, when being worn by a user. The smartwatch 1002 is configured with a memory 1012, communication circuitry 1014 and a display device 1022. The communication circuitry 1014 may transmit sensor measurement signals to a communication device in a vehicle 102 or to a smartphone 1004, having a wireless communications device, using a short-range communications protocol such as Bluetooth, Bluetooth Low Energy, or WiFi.

In some embodiments, when heart rate, ECG signals, or other body metrics are being measured by one sensor, such as the steering wheel mounted sensors 801a, 801b or a wearable device, but the measurement is cut off, the one or more cameras 911, 925 may be used to verify the health condition of the user. For example, the user may momentarily take their hand off of the steering wheel while heart rate is being measured. The one or more cameras 911, 925 will verify that the reason for removal of a hand(s) from the steering wheel was not due to an emergency medical condition of the user, such as fainting, heart attack, falling asleep, etc. In such case, the user may be presented with an audio or visual display indication to notify the user that heart rate, ECG signals, or other sensor measurements are not being made.

In some embodiments, if a user has a wearable health sensor and the vehicle 102 has heart rate and ECG sensors, or other built-in health sensors, each of the sensors may make measurements as a primary and backup measurement, or one sensor may be switched over to another comparable sensor when a measurement has been cut off for the one sensor but the other comparable sensor can perform measurements.

In order to apply the DT framework in a real-life scenario, a use case is a patient DT that monitors real-time health status and detects body metrics anomalies. The implemented use case boils down to build a machine learning model that diagnoses heart diseases and detects heart problems over predicting normal and abnormal heart rhythm. By capturing the ECG signals through wearable sensors or smartwatches, then convert them into a digital format. The collected data will be ready to train a machine learning algorithm after the preprocessing and filtering phase. After training, a predictive model for normal and abnormal rhythms that describe a particular heart condition is ready and in place.

Accordingly, five models were built and trained using real-time ECG rhythms through various machine learning algorithms to test performance on the data set and obtain the best accuracy. The applied algorithms are convolutional neural network (CNN), multilayer perceptron (MLP), logistic regression (LR), long-short-term memory network (LSTM), and support vector classification (SVC).

A. Data Set

The data set used is based on the MITBIH Arrhythmia Database. See G. B. Moody and R. G. Mark, "The impact of the MIT-BIH arrhythmia database," *IEEE Eng. Med. Biol. Mag.*, vol. 20, no. 3, pp. 45-50, May/June 2001, incorporated herein by reference in its entirety. It contains 48 half-hour excerpts of two-channel ambulatory ECG recordings, obtained from 47 subjects studied by the BIH Arrhythmia Laboratory between the years of 1975 and 1979.

Upper and lower signals were obtained by placing the electrodes on the chest, then the analog outputs of the playback unit were digitized at 360 Hz per signal relative to real time using the analog-to-digital converter (ADC) hardware constructed at the MIT Biomedical Engineering Center and at the BIH Biomedical Engineering Laboratory. The data set contains five classes as listed as follows.

1) N: Normal beat.
2) S: Supraventricular premature beat.
3) V: Premature ventricular contraction.
4) F: Fusion of ventricular and normal beat.
5) Q: Unclassifiable beat.

B. System Workflow

Figure 11:
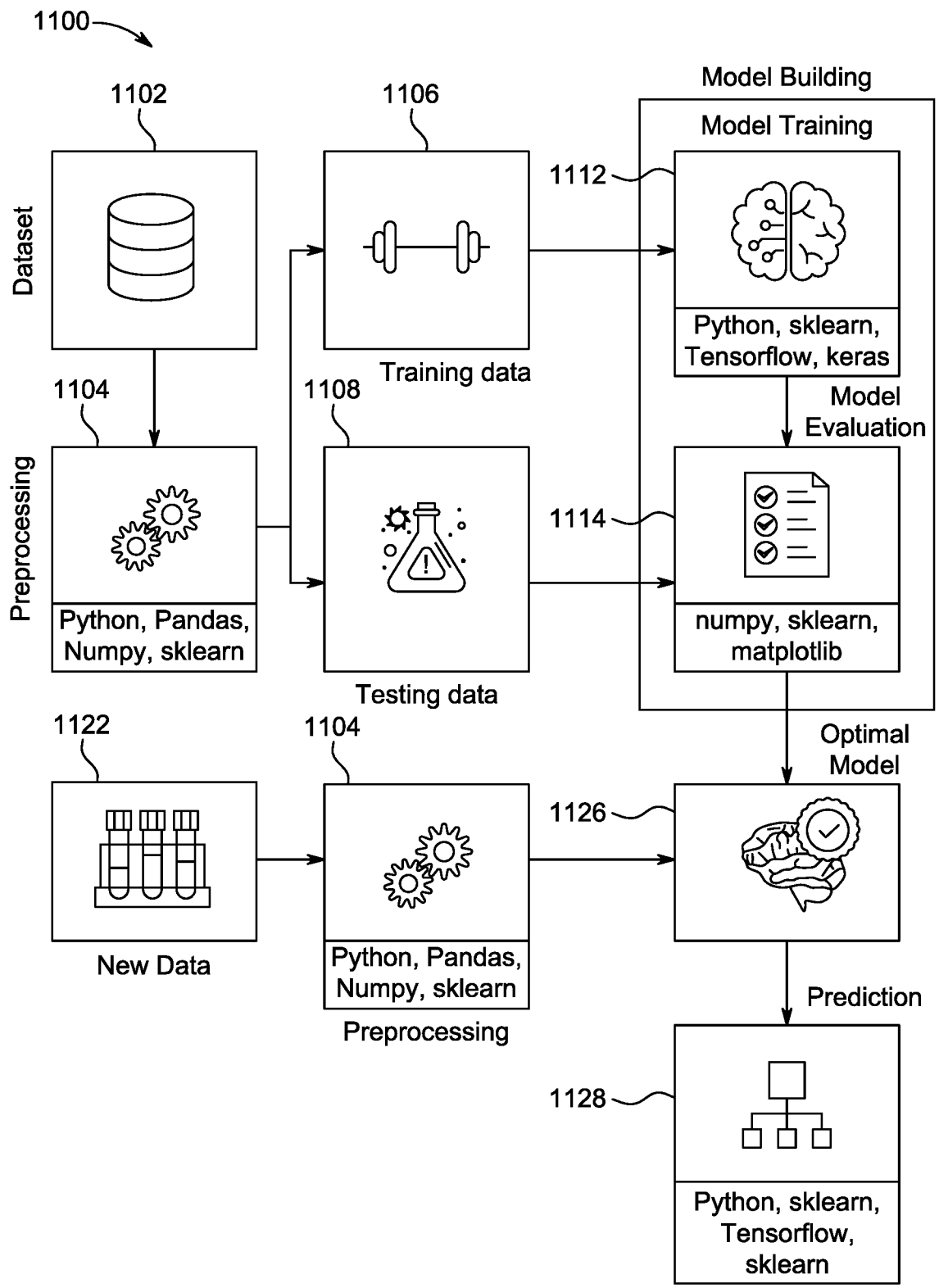
FIG. 11 is a workflow diagram, in accordance with an exemplary aspect of the disclosure.
Figure 12A:
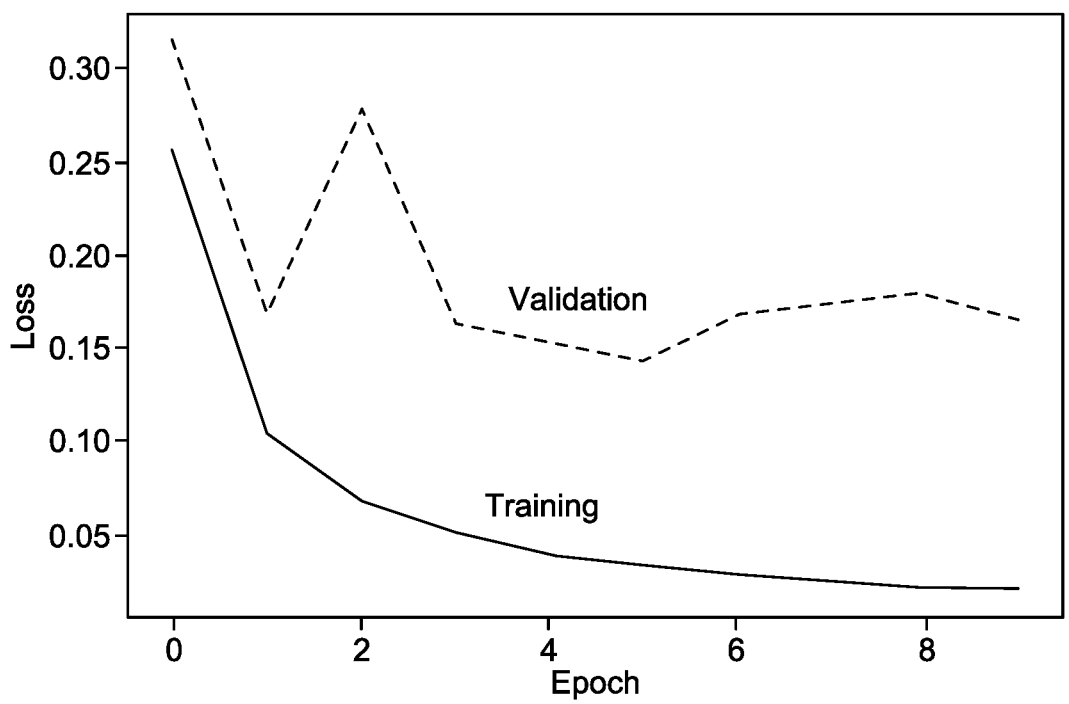
FIGS. 12A and 12B are graphs of long short-term memory model loss and accuracy performance, respectively.
Figure 12B:
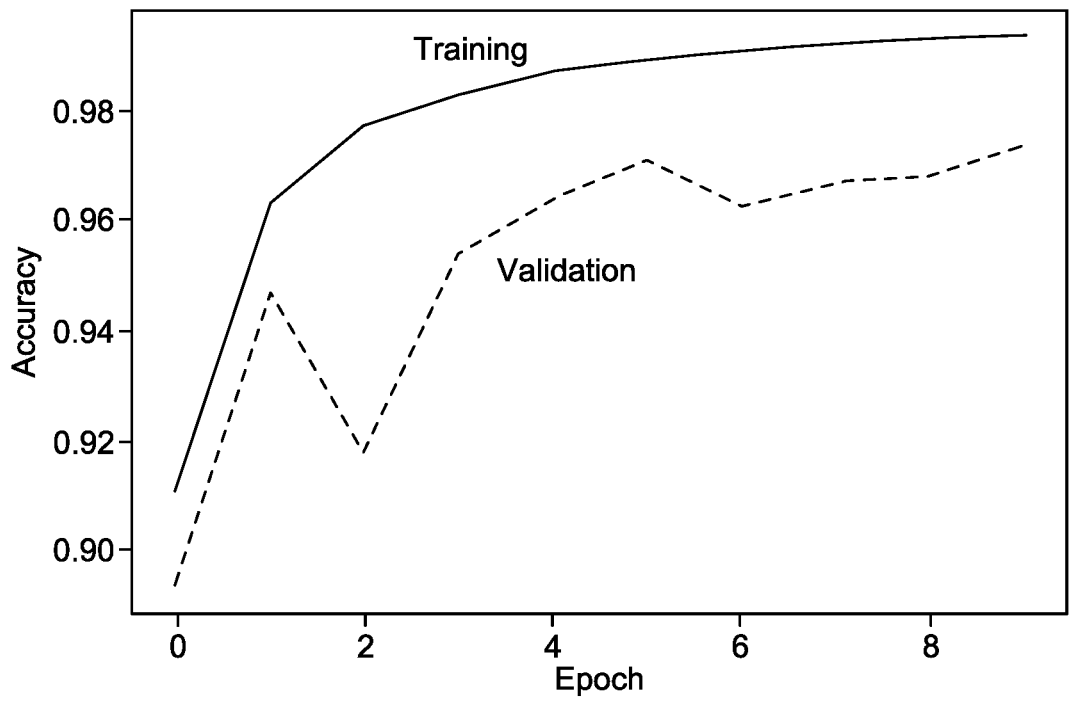
Figure 13A:
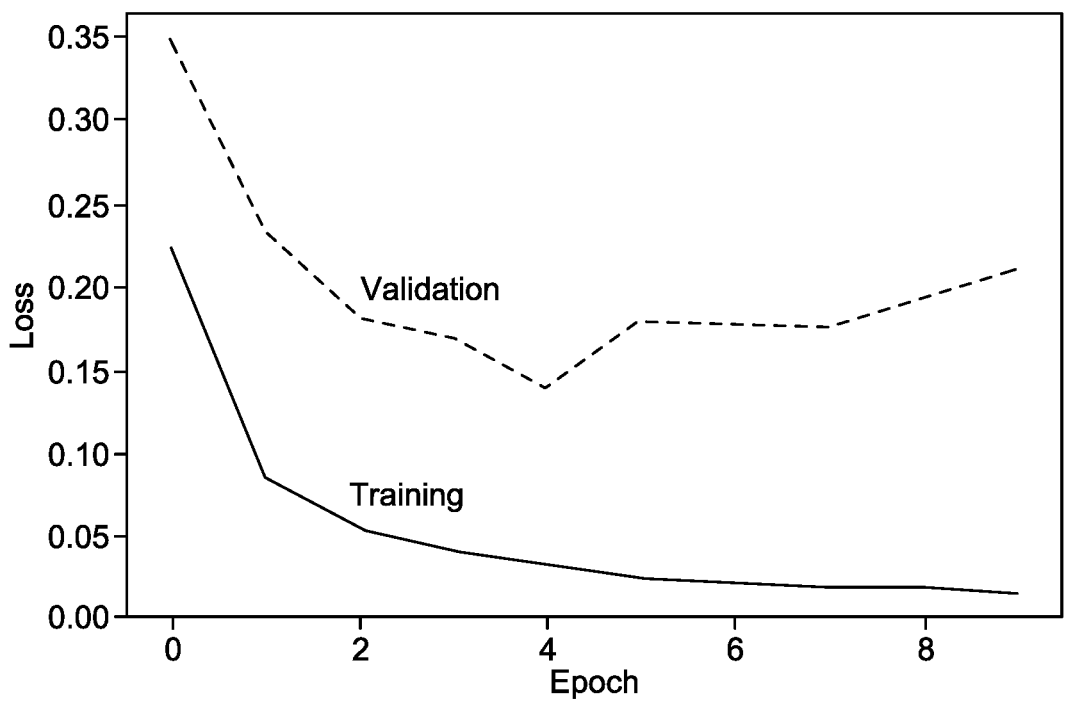
FIGS. 13A and 13B are graphs of convolutional neural network model loss and accuracy performance, respectively.
Figure 13B:
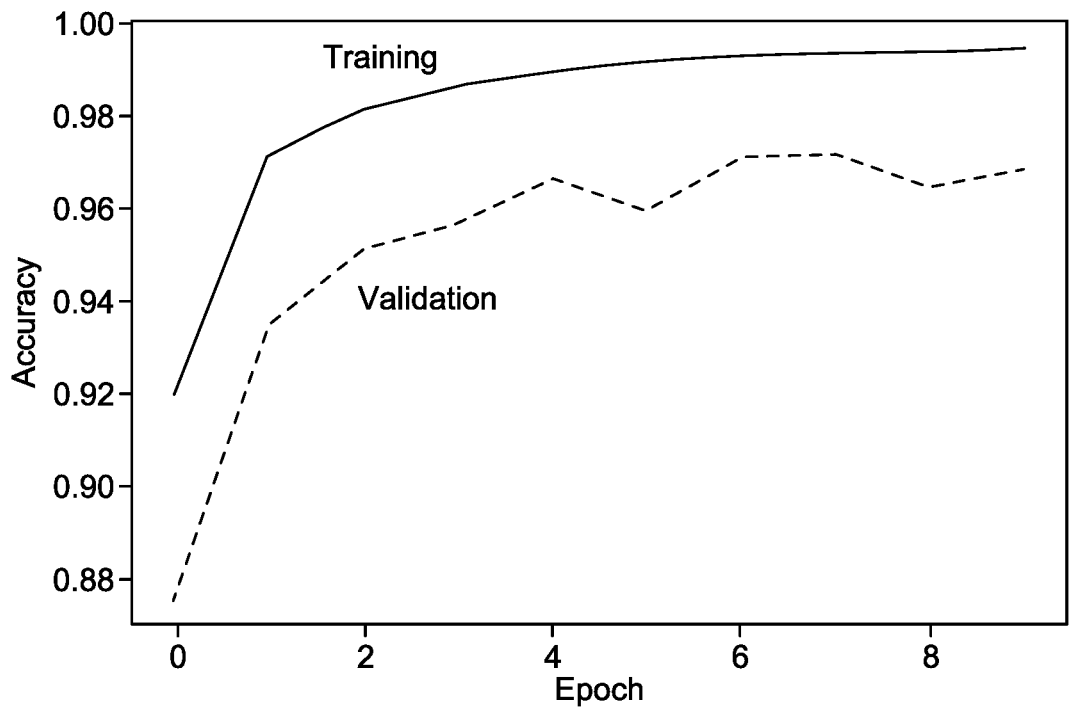

FIG. 11 is a workflow diagram, in accordance with an exemplary aspect of the disclosure. FIG. 11 describes the followed workflow in the DT system construction process. First, the obtained data set was stored in a database 1102 for easy retrieval and processing. Then, the stored data had some preprocessing operations 1104, such as cleansing, resampling, reshaping, and padding. After that, the data were split into two chunks: 1) training data 1106 and 2) testing data 1108 to be used in the model-building phase. The model building phase consists of two stages: 1) model training 1112 and 2) model evaluation 1114. The model training phase 1112 used the training data to train the model and the evaluation phase 1114 used the testing data to assess the model performance. The model building phase was repeated five times with different algorithms to find the optimal model 1126. Finally, after saving the optimal model, the system is ready to receive new data samples 1122 for the prediction process 1128.

Five different models were built to obtain the best accuracy for the data set. The parameters, performance, collected results, and evaluation for each applied model is described. An experiment was carried out using Python, Sklearn library, Tensorflow, and Keras. Also, other libraries were used to help in data preprocessing and results evaluation, such as Pandas, Numpy, and Matplotlib.

Below, the main parameters of each used algorithm and the model structure are described in detail.

First, in order to experience the potential of neural-network-based algorithms, the LSTM sequential model was constructed using LSTM and trained with a 0.01 learning rate over 10 epochs. The optimal model saved at epoch 5 with a minimum achieved validation loss of 0.1430, a 0.9709 validation accuracy, a 0.0329 training loss, and a 0.9896 training accuracy.

Another neural-network-based model, the CNN model, was applied. This model was constructed using the CNN and trained with a 0.01 learning rate over 10 epochs. The optimal model saved at epoch 4 with a minimum achieved validation loss of 0.1391, a 0.9667 validation accuracy, a 0.0331 training loss, and a 0.9896 training accuracy.

FIGS. 12A, 12B, 13A, 13B illustrate the performance of loss and accuracy for the LSTM sequential and CNN models over training epochs, respectively. Although the accuracy increases over the epochs, the loss also increases. This indicates that the models are less certain about their predictions. Accordingly, the best LSTM model was saved at epoch 5 and the best CNN model was saved at epoch 4 with the minimum achieved validation loss. The results show that the LSTM validation accuracy is higher than the CNN validation accuracy but the CNN validation loss is lower than the LSTM validation loss. The difference between them is merely fractions which makes their performance very close to each other.

The MLP model was constructed using the MLP algorithm and achieved 0.956 testing accuracy over 800 iterations. Also, two experiments were tested on traditional machine learning algorithms. The SVC model was constructed using the SVC algorithm and achieved 0.756 testing accuracy on the linear kernel. The last applied model was the LR. This model was constructed using the LR algorithm and achieved 0.676 testing accuracy over 900 iterations with saga solver.

A. Evaluation

Next the evaluation metrics used to compare the applied model performance and choose the optimal one is described.

1) Accuracy: Accuracy, as shown in (1), gives the percentage of correctly predicted samples which are the true positives (TPs) and true negatives (TNs) out of all data samples (TPs, TNs, false positives (FPs), and false negatives (FNs)). It measures how often the algorithm correctly classifies a data sample $$\text{Accuracy} = \frac{TP + TN}{TP + NP + FP + FN}. \quad (1)$$

Figure 14:
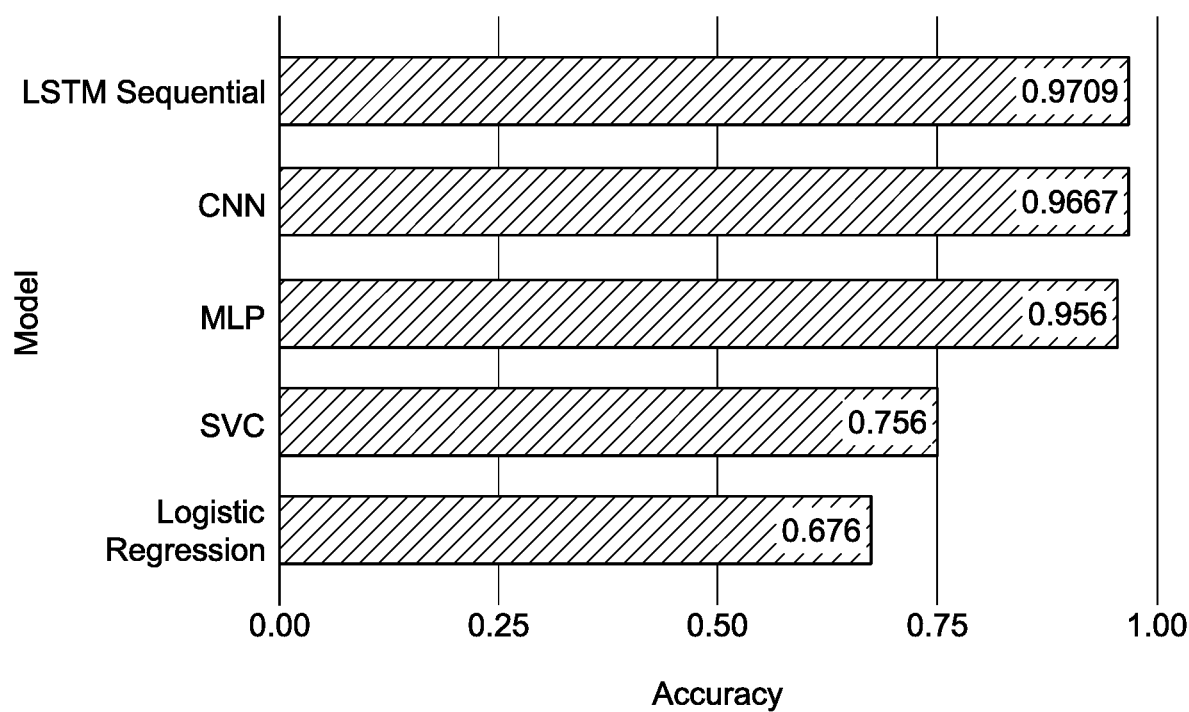
FIG. 14 is a chart of model accuracy.

FIG. 14 compares the accuracy achieved across the five models, and it is clear that the LSTM model has achieved the highest accuracy. It also shows that the neural-network-based algorithms perform better than other traditional algorithms at accuracy score.

2) Confusion Matrix: For the purpose that the testing data set is imbalanced, the accuracy rate may sometimes be misleading. In order to ensure that the models perform well, Tables II-VI show the confusion matrix that describes the performance of each model. By obtaining the confusion matrix, we were able to find the TP, FP, TN, and FN values.

TABLE II

LSTM MODEL CONFUSION MATRIX

| Classes | N | S | V | F | Q |
|---|---|---|---|---|---|
| N | 17,682 | 291 | 71 | 59 | 15 |
| S | 73 | 467 | 8 | 7 | 1 |
| V | 37 | 10 | 1,375 | 24 | 2 |
| F | 11 | 1 | 7 | 143 | 0 |
| Q | 14 | 1 | 5 | 0 | 1,588 |

TABLE III

CNN MODEL CONFUSION MATRIX

| Classes | N | S | V | F | Q |
|---|---|---|---|---|---|
| N | 17,584 | 327 | 97 | 69 | 41 |
| S | 64 | 476 | 9 | 5 | 2 |
| V | 29 | 10 | 1,370 | 31 | 8 |
| F | 10 | 2 | 8 | 142 | 0 |
| Q | 11 | 3 | 3 | 0 | 1,591 |

TABLE IV

MLP MODEL CONFUSION MATRIX

| Classes | N | S | V | F | Q |
|---|---|---|---|---|---|
| N | 17,430 | 393 | 165 | 62 | 68 |
| S | 93 | 443 | 14 | 3 | 3 |
| V | 50 | 13 | 1,351 | 26 | 8 |
| F | 16 | 4 | 7 | 134 | 1 |
| Q | 17 | 7 | 8 | 0 | 1,576 |

TABLE V

SVC MODEL CONFUSION MATRIX

| Classes | N | S | V | F | Q |
|---|---|---|---|---|---|
| N | 13,456 | 869 | 2,241 | 1,207 | 345 |
| S | 142 | 360 | 28 | 24 | 2 |
| V | 150 | 32 | 1,147 | 99 | 20 |
| F | 11 | 0 | 8 | 143 | 0 |
| Q | 69 | 6 | 57 | 14 | 1,462 |

TABLE VI

LR MODEL CONFUSION MATRIX

Figure 15A:
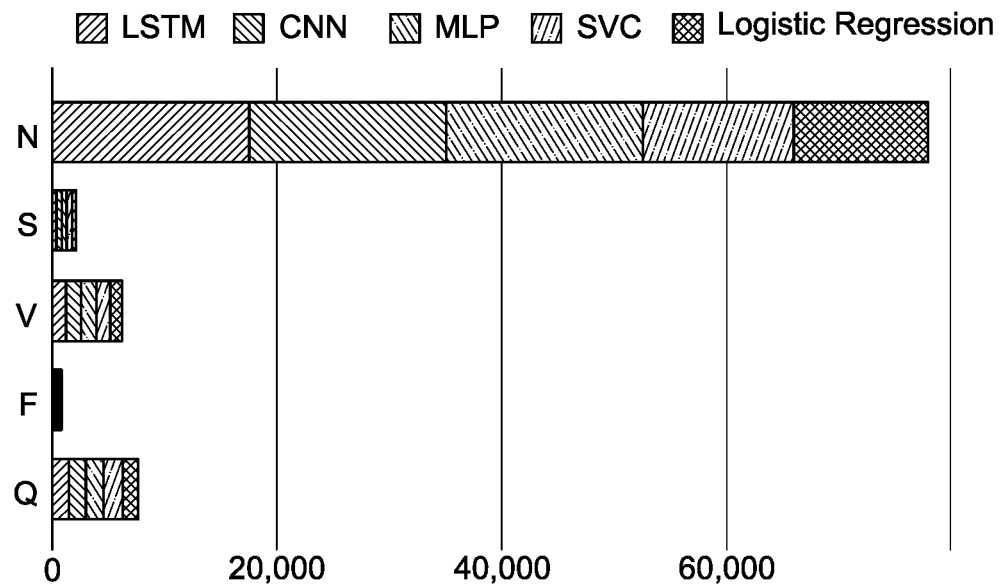
FIGS. 15A, 15B, 15C, 15D are charts of values of TR, TN, FP, and FN, respectively.
Figure 15B:
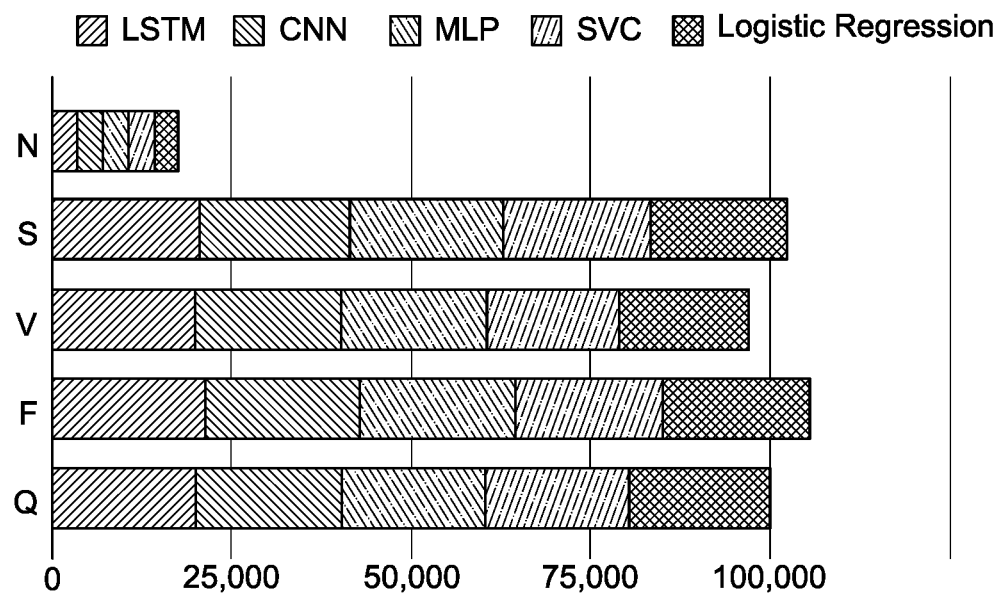
Figure 15C:
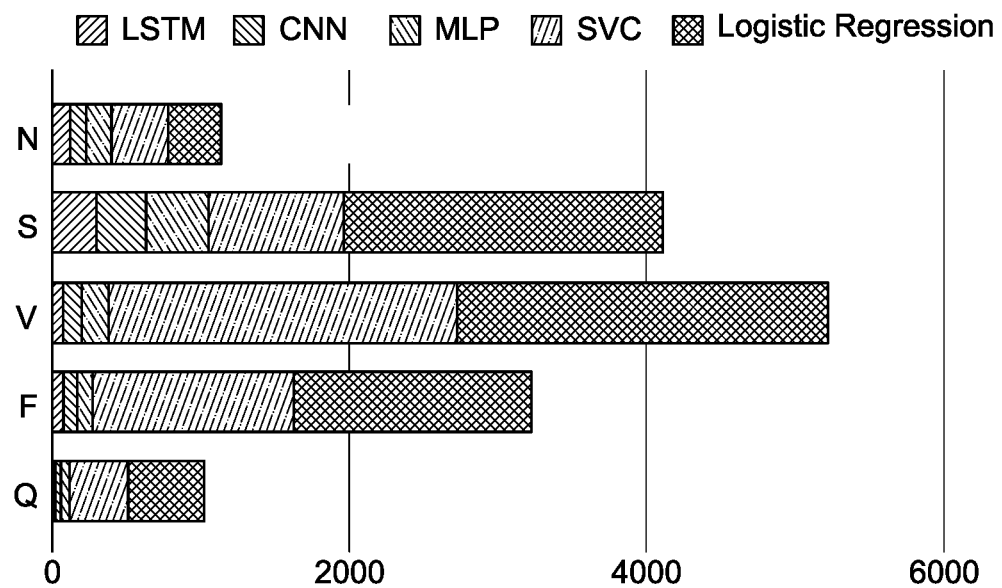

| Classes | N | S | V | F | Q |
|---|---|---|---|---|---|
| N | 11,790 | 2,085 | 2,369 | 1,415 | 459 |
| S | 125 | 370 | 31 | 20 | 10 |
| V | 158 | 53 | 1,038 | 153 | 46 |
| F | 11 | 0 | 9 | 142 | 0 |
| Q | 49 | 5 | 73 | 13 | 1,468 | a) True positives: A TP value is considered when the model correctly predicts the positive class. FIG. 15A (FIG. 7(a)) compares the TPs values for each model across the five classes. Neural-network-based models almost have similar TP values across classes and higher than SVC and LR models values.

b) True negatives: A TN value is considered when the model correctly predicts the negative class. FIG. 15B (FIG. 7(b)) compares the TNs values for each model across the five classes. Neural-network-based models almost have similar TN values across classes and higher than SVC and LR models values.

c) False positives (type I error): An FP value is considered when the model incorrectly predicts the positive class. FIG. 15C (FIG. 7(c)) compares the FPs values for each model across the five classes. The SVC and LR models have a higher type I error for some classes than the rest of the models, especially in the S, V, and F classes which were predicted as S, V, and F but they were not actually from these classes.

d) False negatives (type II error): A FN value is considered when the model incorrectly predicts the negative class.

Figure 15D:
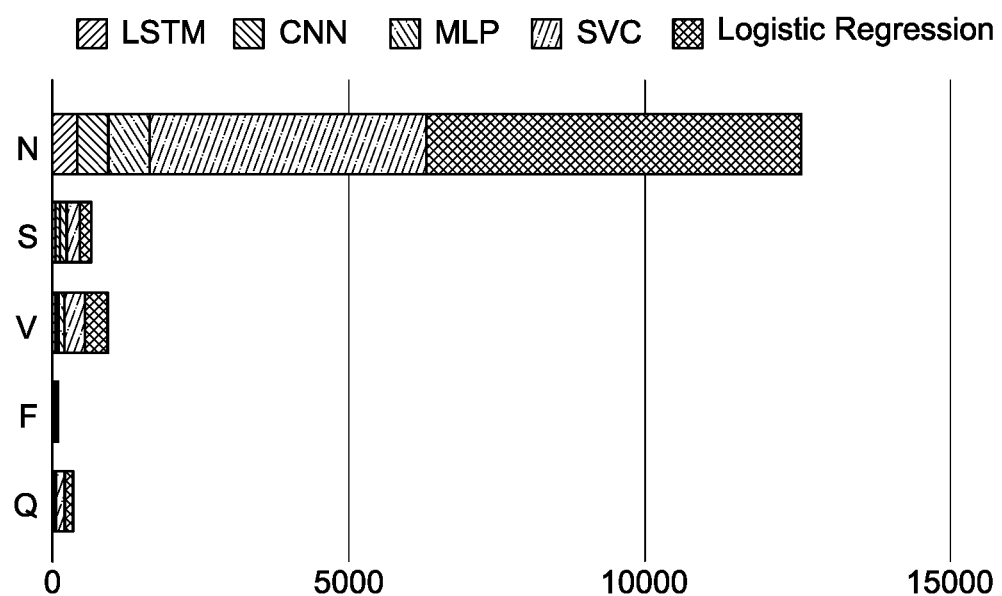

FIG. 15D (FIG. 7(d)) compares the FPs values for each model across the five classes. The SVC and LR models have a higher type II error for some classes than the rest of the models, especially in the N class that considers a patient to have normal ECG rhythms, which means the model predicts a bad condition where the patient has normal beats. This explains the high FPs for S, V, and F classes in SVC and LR models.

3) Classification Report: After obtaining the confusion matrix values, we were able to calculate the main classification metrics: Precision, Recall, and F1-score using the classification report. Tables VII-XI show the classification report to describe the complete performance for each model.

TABLE VII

LSTM MODEL CLASSIFICATION REPORT

| | Metrics | | |
|---|---|---|---|
| Classes | precision | recall | f1-score |
| N | 0.99 | 0.98 | 0.98 |
| S | 0.61 | 0.84 | 0.7 |
| V | 0.94 | 0.95 | 0.94 |
| F | 0.61 | 0.88 | 0.72 |
| Q | 0.99 | 0.99 | 0.99 |
| macro avg | 0.83 | 0.93 | 0.87 |
| weighted avg | 0.98 | 0.97 | 0.97 |

TABLE VIII

CNN MODEL CLASSIFICATION REPORT

| | Metrics | | |
|---|---|---|---|
| Classes | precision | recall | f1-score |
| N | 0.99 | 0.97 | 0.98 |
| S | 0.58 | 0.86 | 0.69 |
| V | 0.92 | 0.95 | 0.93 |
| F | 0.57 | 0.88 | 0.69 |
| Q | 0.97 | 0.99 | 0.98 |
| macro avg | 0.81 | 0.93 | 0.86 |
| weighted avg | 0.97 | 0.97 | 0.97 |

TABLE IX

MLP MODEL CLASSIFICATION REPORT

| Classes | Metrics | | |
|---|---|---|---|
| | precision | recall | f1-score |
| N | 0.99 | 0.96 | 0.98 |
| S | 0.52 | 0.8 | 0.63 |
| V | 0.87 | 0.93 | 0.9 |
| F | 0.6 | 0.83 | 0.69 |
| Q | 0.95 | 0.98 | 0.97 |
| macro avg | 0.79 | 0.9 | 0.83 |
| weighted avg | 0.96 | 0.96 | 0.96 |

Precision, as shown in (2), is the accuracy of positive predictions. The SVC and LR models show a low precision scores for S, V, and F classes which indicates a large number of FPs $$\text{Precision} = \frac{TP}{TP + FP}. \tag{2}$$

TABLE X

SVC MODEL CLASSIFICATION REPORT

| Classes | Metrics | | |
|---|---|---|---|
| | precision | recall | f1-score |
| N | 0.97 | 0.74 | 0.84 |
| S | 0.28 | 0.65 | 0.39 |
| V | 0.33 | 0.79 | 0.47 |
| F | 0.1 | 0.88 | 0.17 |
| Q | 0.8 | 0.91 | 0.85 |
| macro avg | 0.5 | 0.79 | 0.55 |
| weighted avg | 0.89 | 0.76 | 0.8 |

TABLE XI

LR MODEL CLASSIFICATION REPORT

| Classes | Metrics | | |
|---|---|---|---|
| | precision | recall | f1-score |
| N | 0.97 | 0.65 | 0.78 |
| S | 0.15 | 0.67 | 0.24 |
| V | 0.29 | 0.72 | 0.42 |
| F | 0.08 | 0.88 | 0.15 |
| Q | 0.74 | 0.91 | 0.82 |
| macro avg | 0.45 | 0.76 | 0.48 |
| weighted avg | 0.88 | 0.68 | 0.74 |

Recall, as shown in (3), is the fraction of positive samples that were correctly identified from the actual positives. The SVC and LR show a lower recall score, indicating many FN values, compared to neural-network-based models, but all scores are considered good scores $$\text{Recall} = \frac{TP}{TP + FN}. \tag{3}$$

F1-Score, as shown in (4), is the harmonic mean of Precision and Recall. The SVC and LR models show a low F1-score for S, V, and F classes. Also, neural-network-based models show a lower F1-Score for S and F compared to other classes, which means the models do not perform very well in predicting these classes $$F1\text{-score} = \frac{2 \times TP}{(2 \times TP) + FP + FN}. \tag{4}$$

4) Macro Average and Weighted Average: Macro average, as shown in (5), computes the metric for each label and returns the average without considering the proportion for each label in the data set (averaging the unweighted mean per label)

$$\text{Macro Avg.} = \frac{\Sigma m}{N} \tag{5}$$

where m=metric score for each class and N=number of classes.

Weighted average, as shown in (6), computes the metric for each label and returns the average considering the proportion for each label in the data set (averaging the support-weighted mean per label)

$$\text{Weighted Avg.} = \Sigma(S \times m) \tag{6}$$

where s=percentage of samples for each class from total samples.

Figure 16:
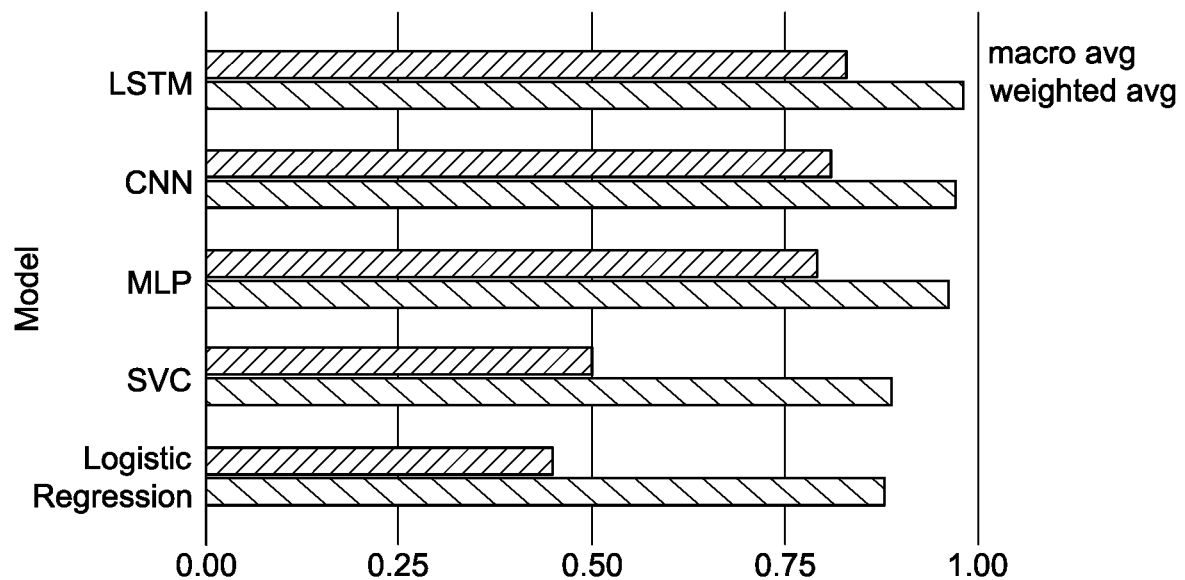
FIG. 16 is a chart of precision score.
Figure 17:
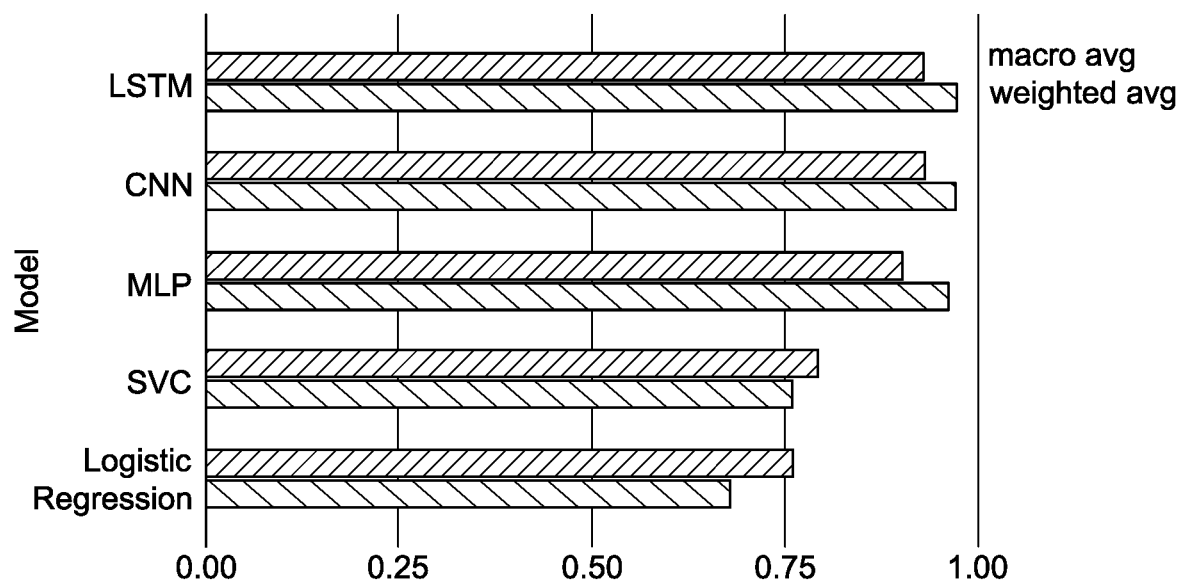
FIG. 17 is a chart of recall score.
Figure 18:
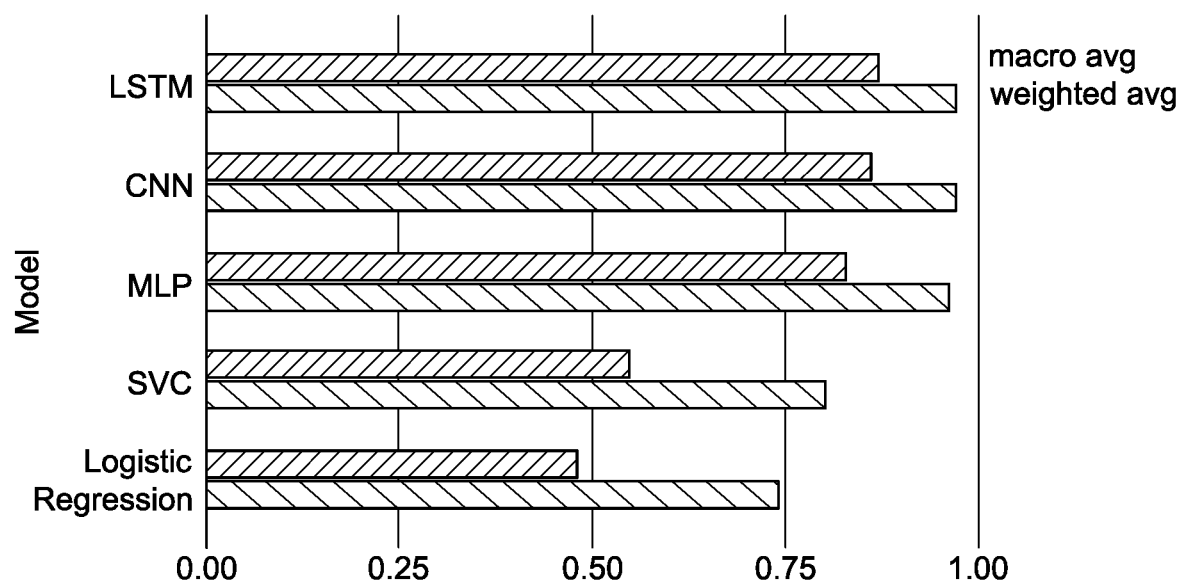
FIG. 18 is a chart of F1 score.

FIGS. 16-18 illustrate a comparison of weighted average and macro average between the models for Precision, Recall, and F1-score. It is clear that the LSTM model always gets the highest score across all metrics. Also, the neural-network based models perform better across the whole data set than traditional machine algorithms models.

Figure 19:
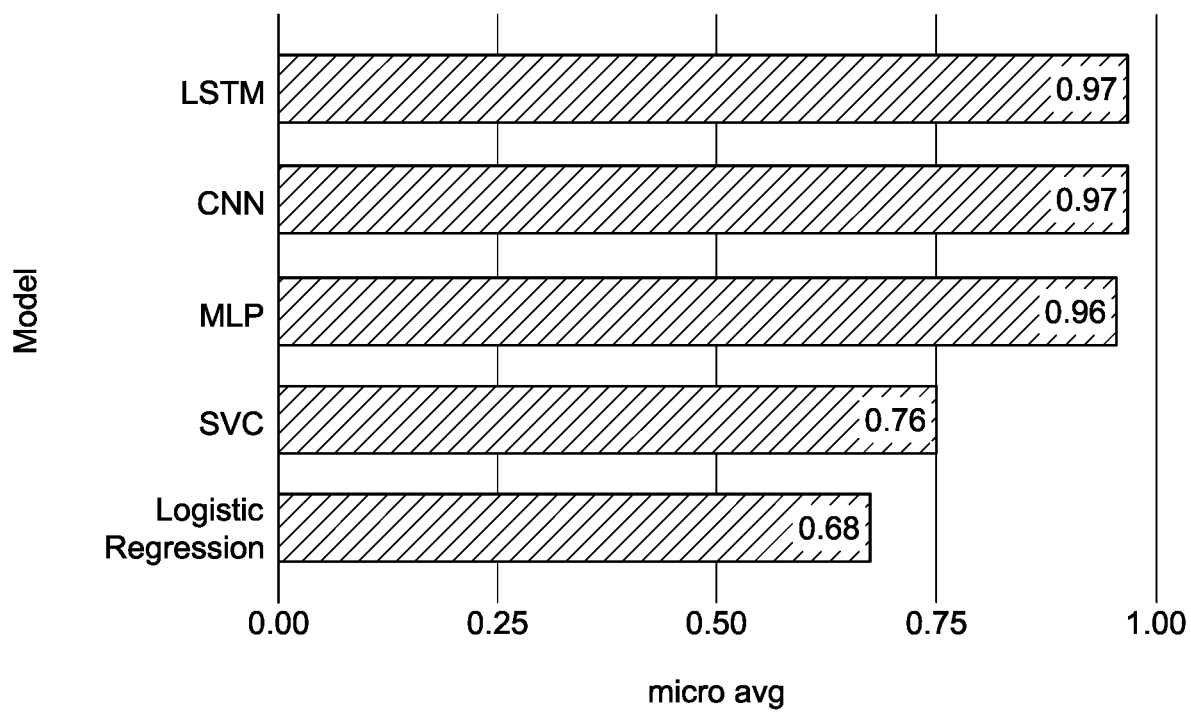
FIG. 19 is a chart of micro average.
Figure 20A:
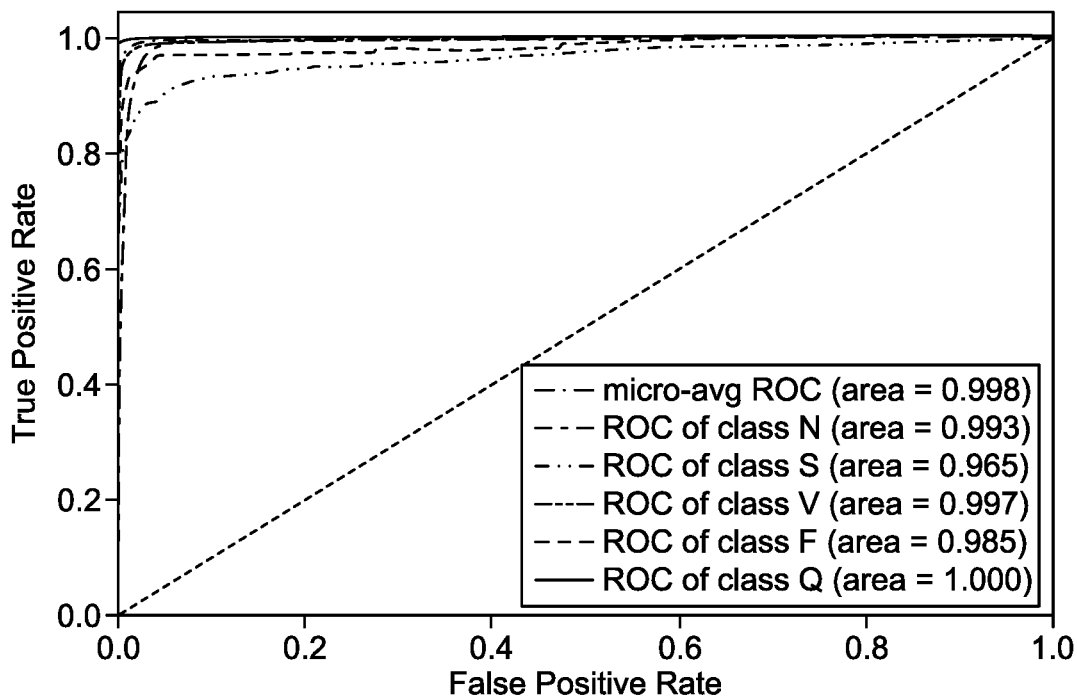
FIGS. 20A, 20B, 20C, 20D, 20E are graphs of ROC curves.
Figure 20B:
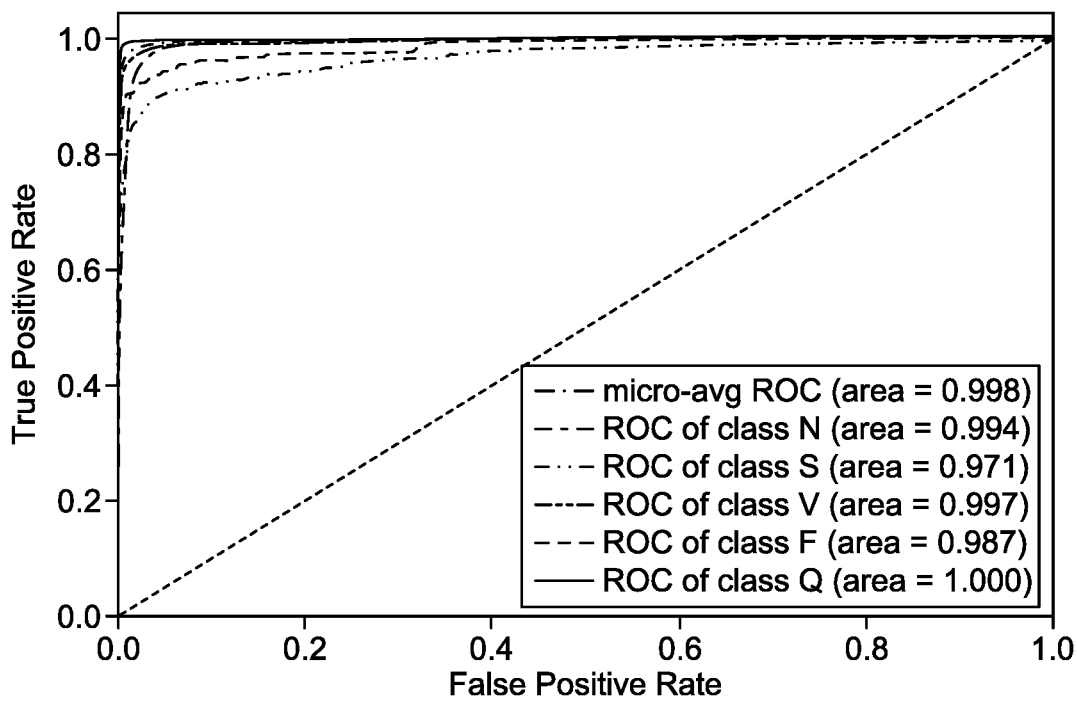
Figure 20C:
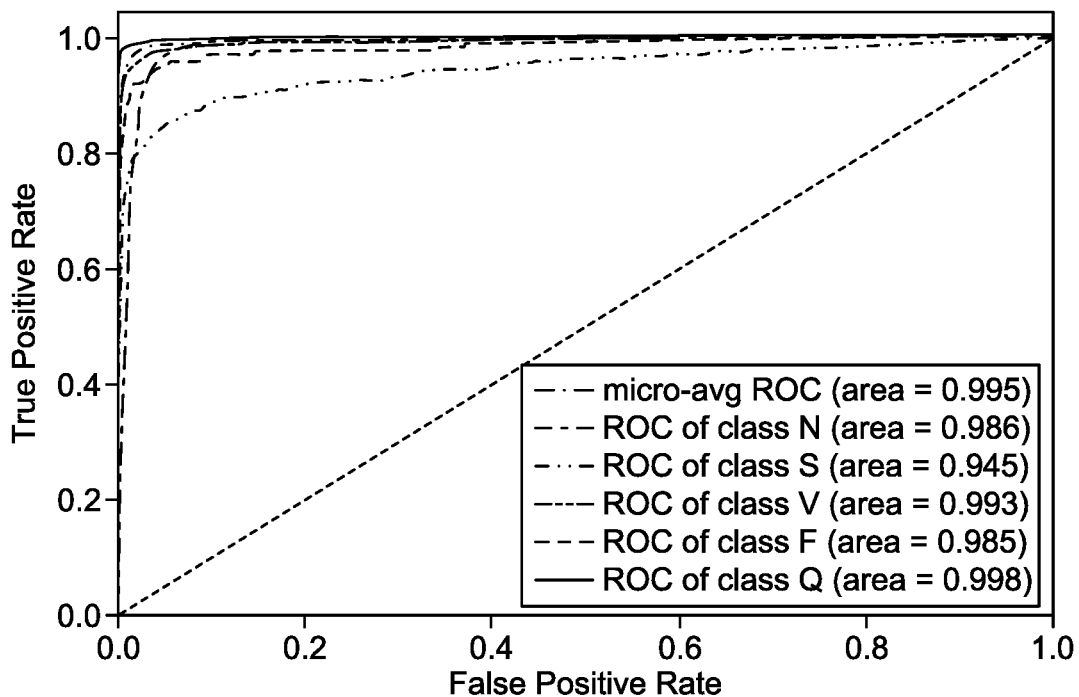
Figure 20D:
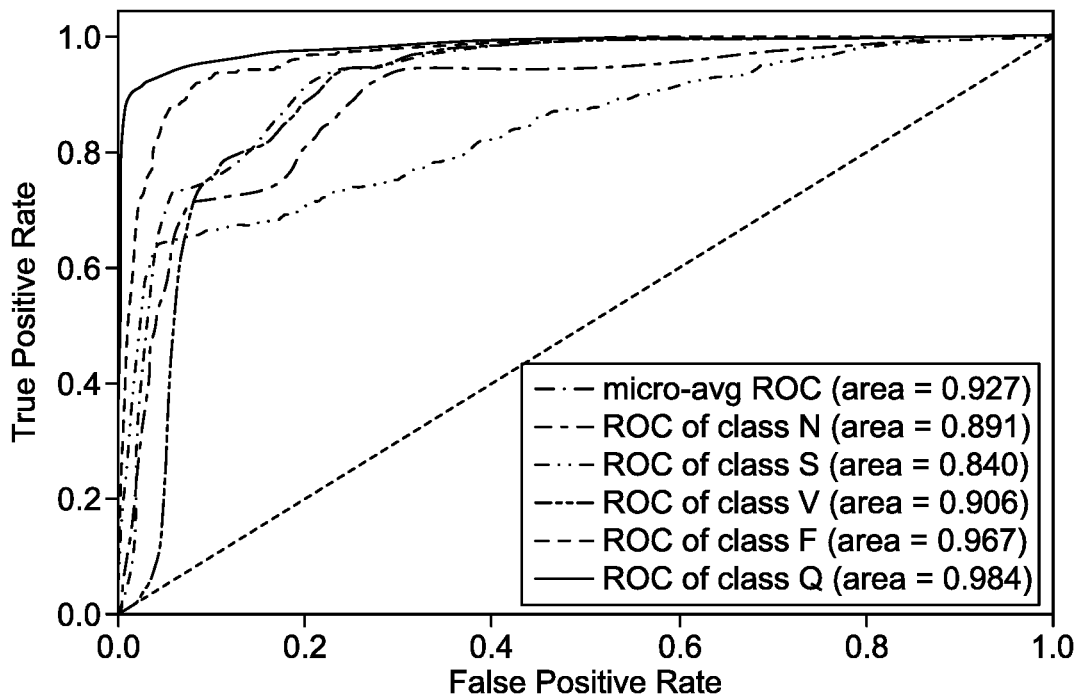
Figure 20E:
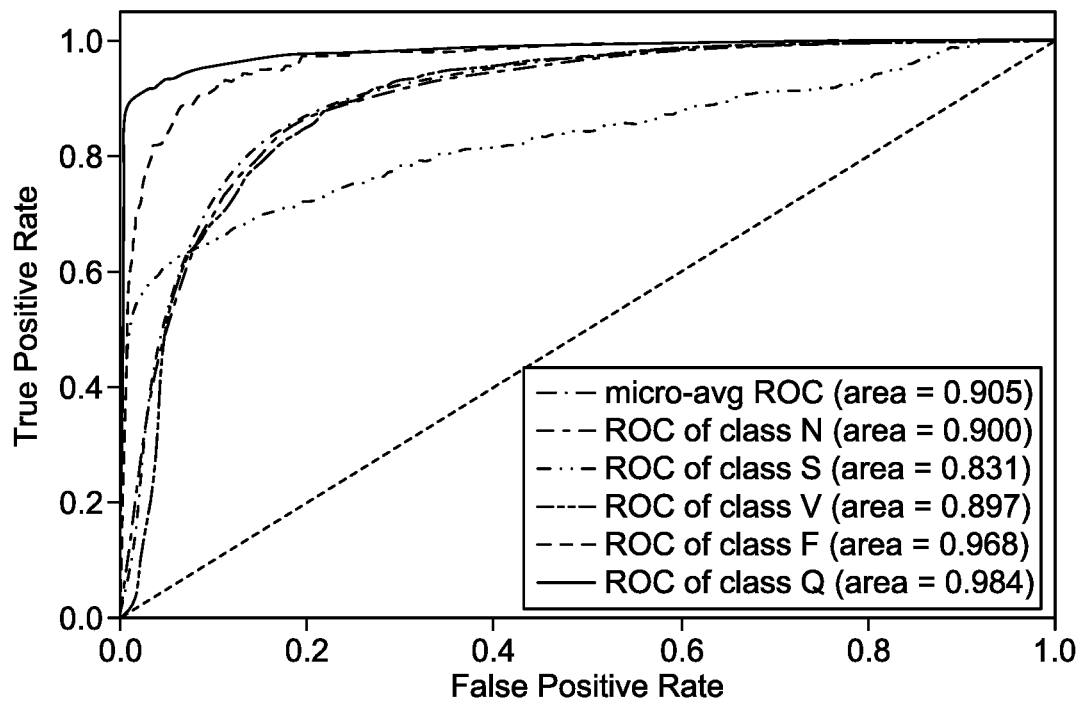

5) Micro Average: Micro average is an averaging technique which calculates the total TP, FN, and FP when the testing data set is imbalanced. MicroAvg aggregates the contributions of all classes to compute the average metric. It is the same for all metrics in the classification report and gives the same results as accuracy. Therefore, the same findings were considered that neural-network-based models performed better in classifying the data set than other models. FIG. 19 compares the micro average achieved across the five models.

6) ROC and AUC: The receiver operating characteristic curve is a probability model to compare the TP rate against the FP rate at different thresholds using the graphical plot (sensitivity against specificity). The area under the curve measures the ability of a classifier to distinguish between different classes. The higher AUC close to 1 means the classifier performs well. An AUC close to 0.50 means the classifier is guessing and has no separation capacity. The lower AUC close to 0 means that the model is 100% wrong and it predicts the opposite class.

FIGS. 20A, 20B, 20C, 20D, 20E illustrate the receiver operating characteristic curve for each model using the one-versus-rest method and the legends show the area under the curve for micro average ROC. All models had an AUC score above 80 for all classes which means that all models can distinguish between classes well.

The experiments show that the neural-network-based models perform better than traditional machine learning algorithms in terms of evaluation metrics. For accuracy, the LSTM sequential model achieved the highest accuracy score with 0.97. Also, the deep NN models achieved higher scores than SVC and logistics regression models.

The confusion matrices showed that the traditional algorithms (SVC and logistics regression) misclassified some classes with higher FP and FN values than neural-network-based algorithms.

Precision, Recall, and F1-score metrics showed that neural-network-based algorithms achieved higher scores than other models, taking into consideration the macro and weighted average results for each metric. Furthermore, they showed that the LSTM sequential model achieved 0.83, 0.93, and 0.87 macro average for Precision, Recall, and F1-score, respectively, and 0.98, 0.97, and 0.97 weighted average for Precision, Recall, and F1-score, respectively, which were the highest scores across all models. Finally, the area under the curve (ROC) showed that all models had a high AUC score above 80 for all classes which means all models can distinguish between classes.

Federated learning is used to train the DT for health issue prediction in order to improve trust, security and privacy, standardization, diversity and multisourcing.

Trust

The concept of the DT itself of having a virtual replica for a physical asset may have a gap since it relies on devices to transfer the data, while these devices may be crashed or disconnected for any reason. Also, DTs typically require a contribution from field professionals. These professionals must be qualified and ethical to give accurate feedback, edit and preserve data.

Security and Privacy

Protecting the DT systems from unauthorized access, abuse, modification, or disclosure will be a challenge as in any other information system. As DT systems process large volumes of sensitive and personal data, this will make it a target for threat actors and cyberattacks. In addition, the use of the IoT devices and sensors may add more complexity in terms of implementing proper security as the traditional security controls mostly do not fit with them. Processing personal user's data could raise regulatory risks. Complying with privacy regulations such as GDPR in Europe or regulations at relevant national protection laws could be a mandatory and adding more challenges when designing DT systems.

Standardization

Lack of standards is another critical challenge. This factor affects security, privacy, interactions, roles, contribution protocols, data transmission, and synchronization between the virtual and physical world. Setting global standards would help to spread the trend of DTs more rapidly and make it a reality faster.

Diversity and Multisourcing

Another problem facing DTs is the data diversity and their multiple sources. This occurs due to the different sources through which data is captured, also the diversity of data types. Which causes problems in processing and building machine learning models as this data is heterogeneous.

A combination of federated learning and distributed blockchain are used to build trust and increase security and privacy. Federated learning reduces the amount of data exchange, particularly the exchange of health-related data, between devices. Individual's private health-related data is securely maintained locally, while health emergency reports are maintained securely in a distributed blockchain.

In embodiments, actions performed by the out-vehicle phase 200 are triggered by an emergency alert generated by the in-vehicle phase. After predicting an abnormal health status that indicates a high risk of a health condition that would require emergence medical assistance, the in-vehicle system will begin its process. Algorithms 2 and 3 will work simultaneously as the vehicle will broadcast an emergency alert 162, 164 to all surrounding vehicles 142 and RSUs 144 requesting an emergency treatment provider. Upon receiving the emergency message, vehicles 142 and RSUs 144 that can provide emergency treatment will broadcast their position coordinates.

---

Algorithm 2 Vehicle Emergency Response System

Input: Alert
Output: min_distance, closest_Coords, S_I D,
    S_type, emergency_message( ),
    health_report_message( )
1 function emergency_message( )
2 | if (Alert) then
3 | |  $V \xrightarrow{broadcast}$ emergency_message( )
4 | end
5 end
6 function closest_provider( )
7 |  closest_Coords = (x,y)
8 |  min_distance = 9897878888
9 |  S_ID = "sssss"
10 |  S_type = "sssss"
11 |  while $V \xleftarrow{receive}$ position_message( ) do
12 | |  $V_x$_Coords = position_message( ).coordinates
13 | |  V_distance = V_Coords − $V_x$_Coords
14 | |  if V_distance < min_distance then
15 | | |  min_distance = V_distance
16 | | |  closest_Coords = $V_x$_Coords
17 | | |  S_ID = position_message( ).sender_ID
18 | | |  S_type = position_message( ).type
19 | |  end
20 |  end
21 |  return min_distance, closest_Coords, S_ID, S_type
22 end
23 function perform_action( )
24 |  if (S_type = = RSU) then
25 | |  $V \xrightarrow{broadcast}$ health_report_message(S_ID)
26 | |  V ← set_destination(closest_Coords)
27 |  end
28 |  else if (S_type = = AV) then
29 | |  V ← set_parking_(x,y)
30 | |  $V \xrightarrow{broadcast}$ set_parking_message(x, y, S_ID)
31 | |  $V \xrightarrow{broadcast}$ health_report_message(S_ID)
32 |  end
33 end

---

Algorithm 3 Surrounding AVs and RSUs

Input: emergency_message( ), set_parking_message( )
Output: Process Completed: P
1 function emergency response( )
2 |  if (AV || RSU ← receiveemergency_message( )) then
3 | |  if (RSU is hospital) then
4 | | |  $1_{RSU} \xrightarrow{broadcast}$ position_message($V$)
5 | |  end
6 | |  if (AV = = (is ambulance || has Doctor)) then
7 | | |  $1_{AV} \xrightarrow{broadcast}$ position_message($V$)

-continued

Algorithm 3 Surrounding AVs and RSUs

```
8  |   |  end
9  |  end
10 |  if (AV_{S_ID} ← receiveset_parking_message( )) then
11 |   |  x = set_parking_message( ).x
12 |   |  y = set_parking_message( ).y
13 |   |  AV_{S_ID} ← set_parking(x, y)
14 |  end
15 |  return P
16 end
```

Figure 21A:
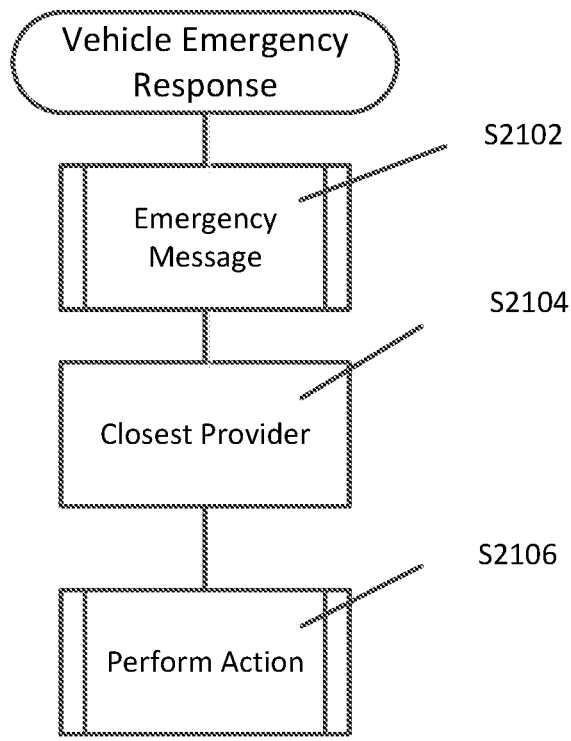
FIGS. 21A, 21B is a flowchart of a vehicle emergency response system, in accordance with an exemplary aspect of the disclosure.
Figure 21B:
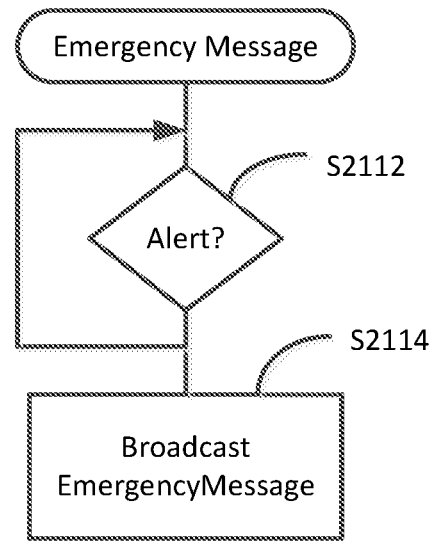

FIGS. 21A, 21B is a flowchart of a vehicle emergency response system, in accordance with an exemplary aspect of the disclosure. In S2102, the vehicle 102 with the impending emergency case broadcasts an alert message. In S2112, if an alert is detected, in S2114, the vehicle 102 will broadcast an emergency message. In S2104, the vehicle 102 selects the vehicle or RSU that is the closest distance. In S2106, the vehicle 102 will perform the next action.

The vehicle emergency response system, as in FIGS. 1 and 2, is an alert system for a driver or a passenger of a vehicle 102. An emergency health condition may be detected while the vehicle is being driven. In some embodiments, an emergency health condition may be detected while a driver or passenger is proximate to a vehicle 102, but the vehicle is parked or otherwise not being driven. For example, the vehicle may have been involved in an accident. In other cases, the driver and/or passenger has exited the vehicle 102. In still other cases, the vehicle 102 may be parked at the driver's residence while the driver is at the residence, or parked at a workplace of the driver, again while the driver is at the workplace.

In some embodiments, before step S2114, where the vehicle 102 broadcasts an emergency message, the driver or passenger may be provided with a means to override the automatic broadcast of an alert message. For example, the vehicle 102 or mobile app of a smartphone may be provided with a message asking for authorization to send an alert message. In certain circumstances, the alert message may be automatically broadcast when an emergency health condition has a high likelihood of being life-threatening. A life-threatening condition may be one that the driver is unable to drive the vehicle 102, or one that the driver or passenger has a high risk of death.

In some embodiments, the driver or passenger may be provided with an interactive interface, such as in a touch display in the vehicle 102, or in a user interface of a mobile app, that the driver or passenger can pre-register. The driver or passenger may submit pre-registration information that identifies the person, as well as provide pre-existing health conditions, medications being taken, and physical ailments that may impair the driver or passenger while in a vehicle, or proximate to the vehicle. The sensor data obtained from IoT devices 112 may be configured to focus on monitoring of the pre-existing health conditions. In some embodiments, the vehicle emergency response may set the broadcast of an emergency message based on a risk level of a driver, such as setting a predetermined threshold, which when exceeded will automatically broadcast the emergency message in S2114.

When the vehicle 102 with the impending emergency case receives the position messages from other vehicles, it will calculate the distance to each emergency treatment provider and select the closest. Also, it will save the provider type, whether it is RSU 144 or vehicle 142, and its ID. In some embodiments, the vehicle 102 will perform a monitoring function to periodically ping nearby ambulances or health care facilities to obtain availability and position data. In such case, the vehicle 102 may maintain information of position and distance of potential providers in advance of a health emergency.

Figure 22:
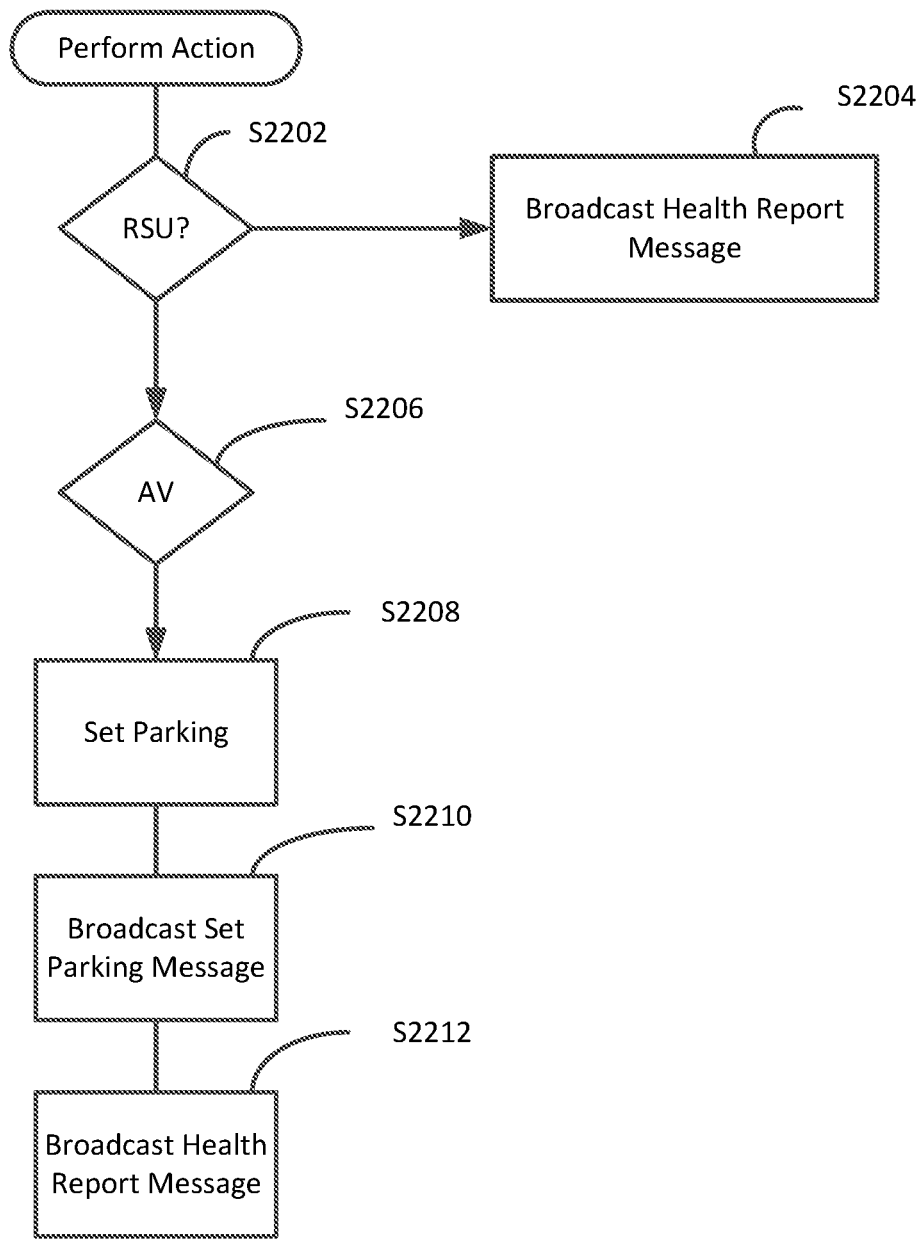
FIG. 22 is a flowchart of a perform action sub-process of the flowchart of FIG. 18.

Depending on the type of provider, the vehicle 142 will perform the next action. FIG. 22 is a flowchart of a perform action sub-process of the flowchart of FIG. 21. In S2202, if the provider is RSU 144, in S2204, the vehicle will change the destination to the RSU position and will send it a health status report. In S2206, if the provider is another vehicle, in S2208, the vehicle will set parking at (x,y) coordinates, then, in S2210, send a parking message to the other vehicle with the coordinates (x,y), and finally, in S2212, will send it a health status report.

Figure 23:
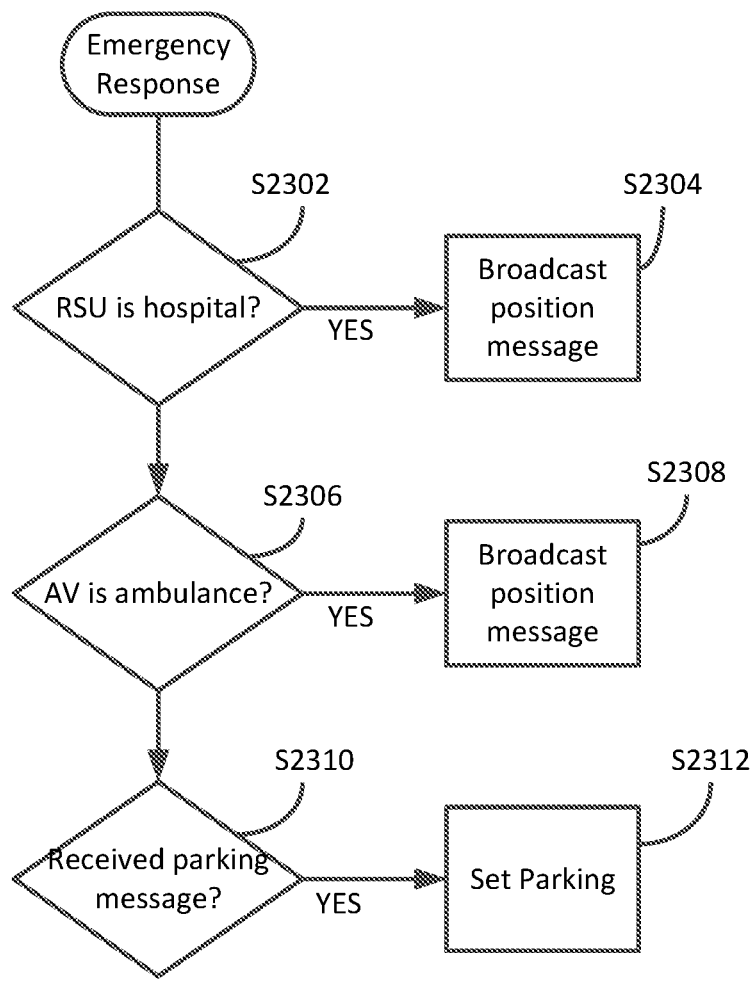
FIG. 23 is a flowchart of emergency response function, in accordance with an exemplary aspect of the disclosure.

FIG. 23 is a flowchart of emergency response function, in accordance with an exemplary aspect of the disclosure. In FIG. 23, in S2302, if the RSU is a hospital, in S2304, the hospital will broadcast a position message. In S2306, if the other vehicle is an ambulance or a doctor, in S2308, the ambulance will broadcast a position message.

In S2310, the last action will be carried out by the other vehicle, as, in S2312, it will set parking at the coordinates (x,y) sent by the vehicle with the emergency case to provide the treatment there.

To evaluate the performance of C-HealthIER, it was applied to existing scenarios for rescuing a vehicle's driver who has an abnormal health condition that makes him unable to continue driving until he receives emergency treatment. The evaluation was performed by simulating two scenarios: the C-HealthIER system and the Autopilot mode for the self-driving car.

Simulation Setup

The simulation was performed using a vehicle network simulation framework: Veins (Vehicle in Network Simulation). Veins is a framework used to create vehicle networks by simulating road traffic with SUMO and wireless communication with OMNeT++. OMNeT++ is an event-based network simulator, and SUMO is a road traffic simulator. Simulation environment specifications and parameters are mentioned in Table II and Table III.

TABLE II

SIMULATION ENVIRONMENT SPECIFICATIONS

| Software | Hardware |
| --- | --- |
| Veins 5.1 | RAM 16 GB DDR4 |
| SUMO 1.8.0 | Processor Intel i7-10750H |
| Omnet++ 5.6.1 | CUP @ 2.60 GHz × 6 |

TABLE III

SIMULATION PARAMETERS

| Parameter | Value |
| --- | --- |
| Communication Standard | IEEE 802.11p |
| Vehicle Length | 2.0 |
| Vehicle Speed | 1.0 |
| Vehicle Acceleration | 1.0 |
| Simulation Time Limit | 3000 s |
| RSU Position X, Y, Z | 280, 230, 3 |
| Parking Area Position X, Y, Z | 300, 26, 3 |

TABLE III-continued

SIMULATION PARAMETERS

| Parameter | Value |
|---|---|
| Vehicles that provide health emergency | car.node[2], car.node[7] |
| Bitrate | 6 Mbps |
| Header Length | 80 bi |

Deep Federated Learning

A deep federated learning model was built using MIT-ECG dataset on a pre-trained model via Tensorflow Federated Framework. The testing data was re-sampled and used as training and testing data for the federated learning process.

The federated learning process was run for 6 federated average rounds. Each round trained on 12000 data samples for 120 participants.

This trained deep federated learning model is used to predict the health status abnormality by the vehicle system.

The Simulation of C-HealthIER Scenarios

In this scenario, the V2V and V2I wireless network and communication were implemented through wireless access in a vehicle environment (WAVE) IEEE 802.11p standard.

At the second 27 of the simulation time, the car.node[0] will receive a health emergency alert sent by the intelligent health monitoring system for predicting an abnormality before it occurs. Based on the alert, the vehicle will handle self-massage to broadcast a short wave message (WSM) to all car nodes and RSU nodes. In response, car.node[2], car.node[7], and rsu.node[0] will broadcast a WSM message that contains their coordinates.

When car.node[0] receives the WSM messages containing the coordinates, it calculates the driving distance to each node. Depending on which type of node has the shortest distance, car.node[0] will take the next action.

Various cases were performed on this simulation to test car.node[0] actions. In one case (Car-node case), the car node[2] was the nearest to car.node[0], so the car.node[0] broadcast parking instructions to it and based on that, the car node[2] set parking at the same position. In another case (RSU-node case), rsu.node[0] was the nearest to car.node[0], so the car.node[0] changed its destination to the rsu.node[0] position.

The Simulation of Autopilot Mode for Self-Driving Car

This simulation implements the Autopilot mode response for self-driving cars if the driver has an abnormal health condition that prevents him from continuing to drive, loses consciousness, and thus loses control of the vehicle.

According to Tesla, if the driver doesn't touch the steering wheel for three alerts, the driver will be banned from using Autopilot during the trip and then the car will automatically stop after 60 seconds, so the car will need 60 seconds to stop. *See Autopilot and Full Self-Driving Capability.* Accessed: May 20, 2021. [Online]. Available: www.tesla.com/, incorporated herein by reference in its entirety.

In this scenario, the driver of car.node[0] loses consciousness at the second 20 and takes his hands off the steering wheel. car.node[0] will stop after 60 seconds. Then car.node[8] "ambulance" will depart from the rsu.node[0] "hospital" to stop at the same position as car.node[2] to take the driver to the hospital. In the simulation, the average emergency response time in the USA of 15 minutes (900 seconds) was used for car.node[8] to respond to the emergency case.

The average waiting time in a hospital's emergency department depends on the emergency case. In the UK, the average wait time for the patient to be seen and treated in the emergency department is 77 minutes in 2021. Therefore, the waiting time to receive emergency treatment must be added to the total simulation time.

In an alternative Autopilot mode, a fully autonomous vehicle can drive without driver intervention. In such case, when the provider is an emergency hospital, the car will set its destination to the provider hospital and will automatically drive to the provider hospital. When the provider is an emergency response vehicle, the car will communicate coordinates as a meeting destination for meeting the provider response vehicle, and will automatically drive to location coordinates of the provider response vehicle.

The Simulation of Traffic Density

Multiple scenarios were implemented at different traffic density levels to verify the effect of traffic on C-HealthIER's approach and AutoPilot mode. Table IV shows the simulation environment parameters: the time when the health emergency occurs, total cars, and the corresponding traffic density level in each scenario. Low, Medium, and High density levels were considered based on the road capacity.

TABLE IV

TRAFFIC DENSITY SIMULATION ENVIRONMENT

| Scenario | Emergency Occurrence Time | Total Cars | Traffic Density Level |
|---|---|---|---|
| AutoPilot mode | 20 | 50 | Low |
| C-HealthIER "Car-node case" | 84 | 64 | Low |
| C-HealthIER" RSU-node case) | 84 | 64 | Low |
| AutoPilot mode | 20 | 135 | Medium |
| C-HealthIER "Car-node case" | 117 | 135 | Medium |
| C-HealthIER "RSU-node case" | 117 | 135 | Medium |
| AutoPilot mode | 20 | 340 | High |
| C-HealthIER "Car-node case" | 244 | 382 | High |
| C-HealthIER "RSU-node case" | 244 | 382 | High |

The Simulation of Two Emergency Cases in One Scenario

Two emergency cases in one scenario were also tested in the simulation under two different scenarios. In scenario 1, both car.node[0] and car.node[1] have passenger health emergencies at a close time and the two vehicles car.node[2] and car.node[7] will provide emergency treatment. When the emergency case occurs at car.node[0] both of them will respond to the help message, while when the emergency case occurs at car.node[3] only one vehicle (car.node[7]) will respond to the help message as the other vehicle (car.node[2]) is occupied to help car.node[0] passenger.

In scenario 2, only the rsu.node[0] will be available to provide the healthcare emergency treatment, both car.node [0] and car.node[1] will send help messages to rsu.node[0] and rsu.node[0] will respond to the message. Then both vehicles will change the direction to rsu.node[0] to receive the treatment there.

As stated before, one aspect of the framework is to minimize the total time to receive the first emergency treatment for maximizing rescue chances for the AV passenger.

Figure 24A:
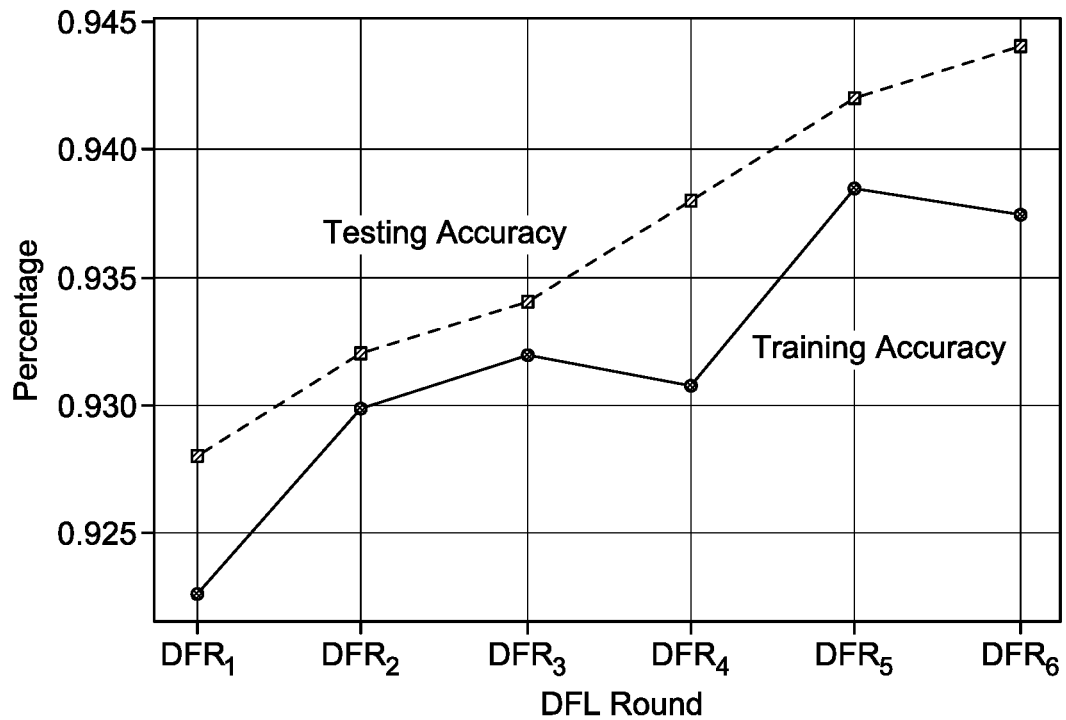
FIGS. 24A and 24B are graphs illustrating Deep Federated Learning model loss and accuracy performance.
Figure 24B:
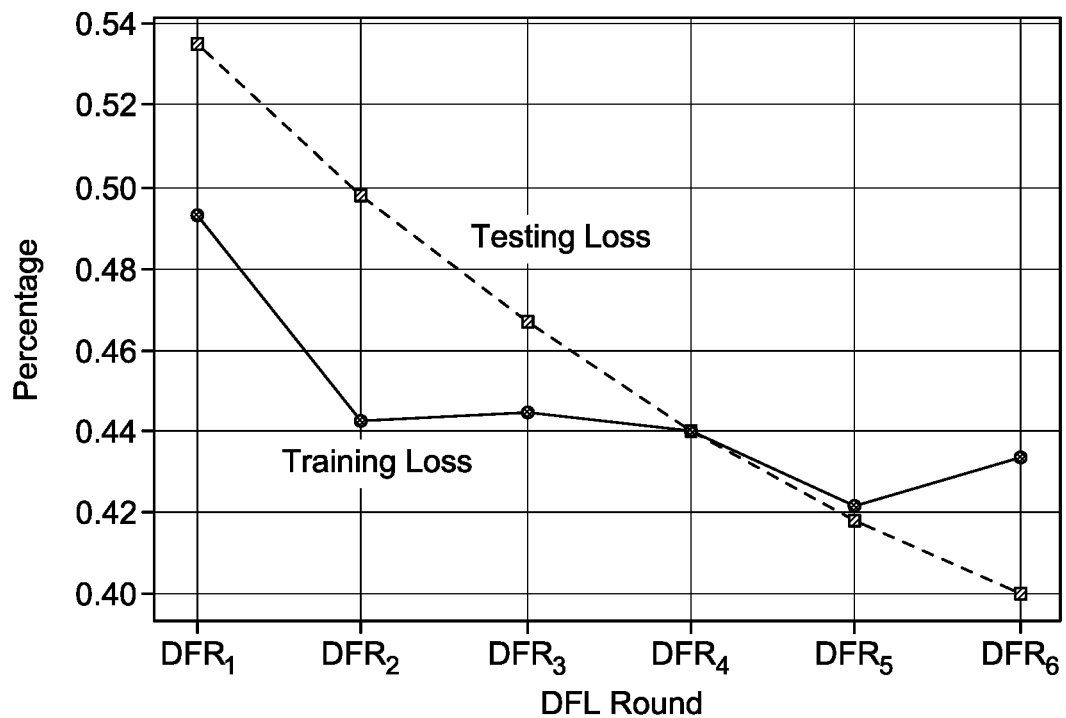

Deep Federated Learning Model: FIG. 24A shows the deep federated learning model's accuracy results over the deep federated rounds (DFR). The training accuracy increased over rounds from 92% up to 93.7%. Also, the testing accuracy increased from 92.8% up to 94.4%. At the same time, the model loss, as shown in FIG. 24B, decreased over the DFR for both training and testing samples by 6% and 13%, respectively, indicating that the model has no overfitting effect. Moreover, the classification report results of testing data are presented in Table V. The results of Precision, Recall, and F1-score increased from round 1 to round 6 by 1% to reach 94% for both macro and weighted averages. Compared to the centralized model that was used to initiate the process, the accuracy decreased. However, in the federated learning phase, the model is updated, the captured data is used, and privacy is preserved.

Figure 25:
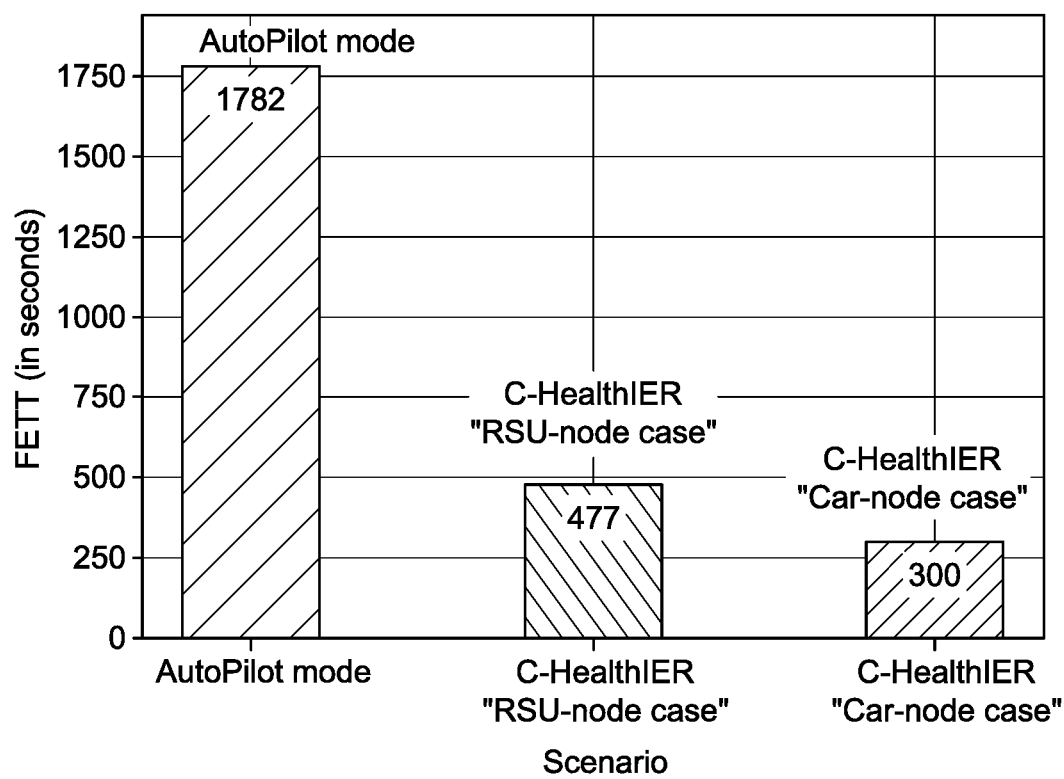
FIG. 25 is a graph illustrating the first emergency treatment time (FETT)

First Emergency Treatment Time (FETT): The total scenario time is the time that the simulation takes until the last action is executed. As shown in FIG. 25, the Autopilot mode scenario took 1782 seconds, while the C-HealthIER scenario took approximately 73% and 83.1% less time, respectively.

Total Emergency Treatment Time: Since the goal was to maximize the passenger's rescue chances, the full time to receive the first emergency treatment time should be considered, including waiting time if any. Accordingly, the waiting in the emergency department should be added to FETT. Table VI shows the waiting time that should be considered to have the Total Emergency Treatment Time.

TABLE V

DFR CLASSIFICATION REPORT

| Round | Average | precision | Recall | F1-score |
|---|---|---|---|---|
| $DFR_1$ | macro avg | 0.93 | 0.93 | 0.93 |
| | weighted avg | 0.93 | 0.93 | 0.93 |
| $DFR_2$ | macro avg | 0.94 | 0.93 | 0.93 |
| | weighted avg | 0.94 | 0.93 | 0.93 |
| $DFR_3$ | macro avg | 0.94 | 0.93 | 0.93 |
| | weighted avg | 0.94 | 0.93 | 0.93 |
| $DFR_4$ | macro avg | 0.94 | 0.94 | 0.94 |
| | weighted avg | 0.94 | 0.94 | 0.94 |
| $DFR_5$ | macro avg | 0.94 | 0.94 | 0.94 |
| | weighted avg | 0.94 | 0.94 | 0.94 |
| $DFR_6$ | macro avg | 0.94 | 0.94 | 0.94 |
| | weighted avg | 0.94 | 0.94 | 0.94 |

TABLE VI

TOTAL EMERGENCY TREATMENT TIME

| Scenario | FETT | Waiting time | First Total Emergency Treatment Time |
|---|---|---|---|
| AutoPilot mode | 1782 second | 4620 seconds | 6402 seconds |
| C-HealthIER RSU-node case | 477 seconds | 0 seconds | 477 seconds |
| C-HealthIER Car-node case | 300 seconds | 0 seconds | 300 seconds |

Based on the UK statistics of the average waiting time to receive the treatment in the emergency department, the Autopilot mode scenario took 6402 seconds to the first emergency treatment, as 4620 seconds of waiting time were added to 1782 seconds as the first emergency treatment time. C-HealthIER scenarios did not require a wait time as a passenger's health status report was sent prior to the arrival to conduct any rescue procedures, allowing the healthcare provider to prepare ahead of time on how to handle the case. Moreover, the intelligent health monitoring system predicts the abnormality condition before it occurs, so the passengers' condition is not severe yet, requiring less effort to deal with the case.

Figure 26:
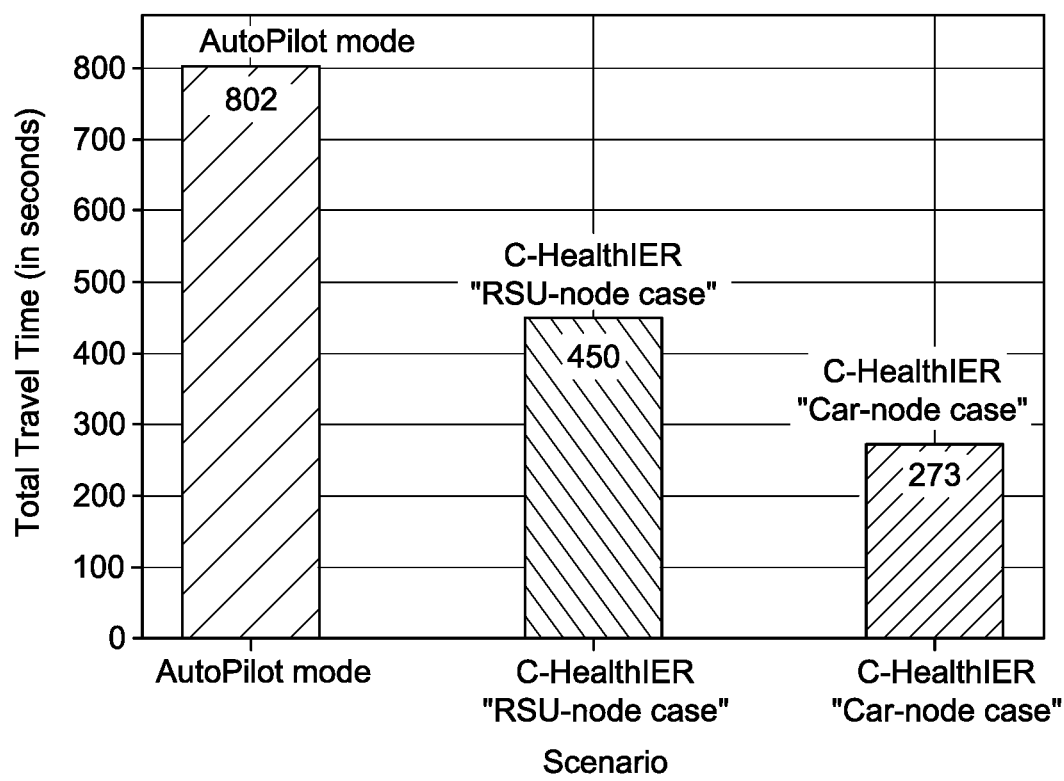
FIG. 26 is a graph illustrating the travel time to first emergency treatment.

Travel Time to First Emergency Response: The total travel time to the first emergency response is when a health emergency occurs up to the time the vehicle arrives for the first emergency treatment. As shown in FIG. 26, the travel time for the AutoPilot mode scenario is roughly twice the C-HealthIER "RSU-node" case scenario because the vehicle heads straight to the hospital instead of waiting for the ambulance to travel the double distance back and forth and thus takes double time. C-HealthIER "Car-node" case scenario depends on the parking area position, and it took the vehicle 273 seconds to travel from the health emergency to its stop in the parking area.

Figure 27:
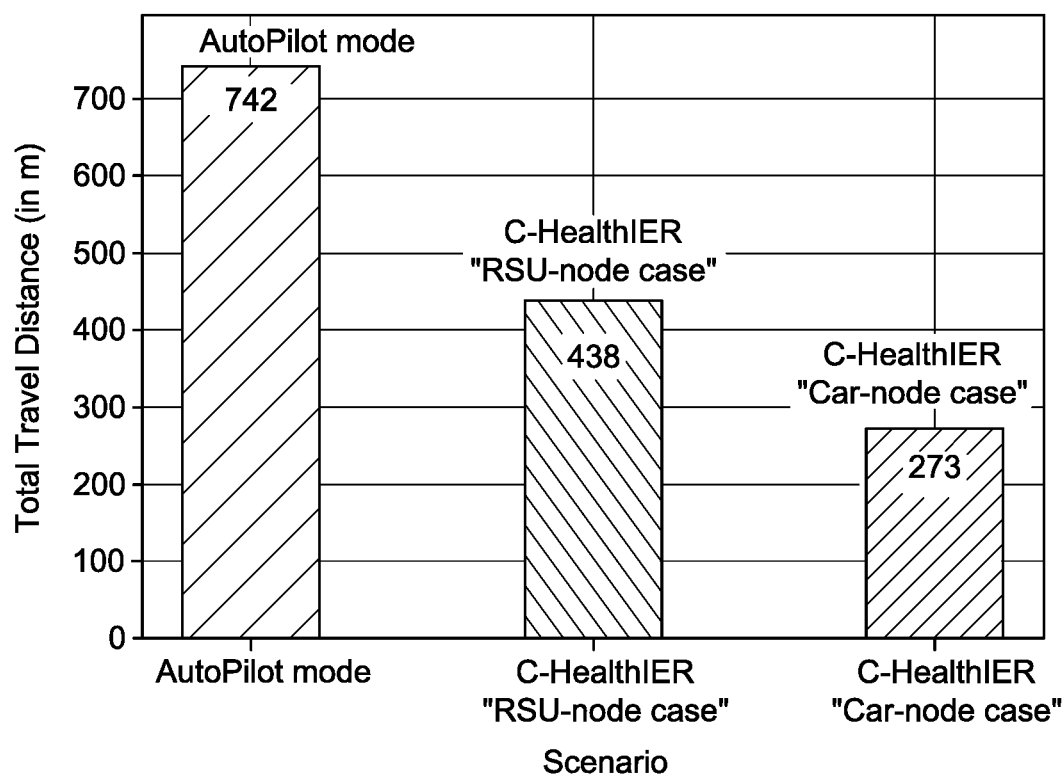
FIG. 27 is a graph illustrating the distance to first emergency treatment.

Travel Distance to First Emergency Treatment: It is the distance the vehicle travels from the moment the health emergency occurs until it arrives at the first emergency treatment place FIG. 27 illustrates the travel distance that was taken in each scenario. In the C-HealthIER "RSU-node" case scenario, the travel distance is less than in the Autopilot mode scenario because in the former scenario, the vehicle is heading directly to the hospital, wherein in the latter where the ambulance moves back and forth from a hospital. As mentioned earlier, the C-HealthIER "Car-node" case scenario is based on the location of the parking area, and the travel distance is 273 meters for this scenario.

Figure 28:
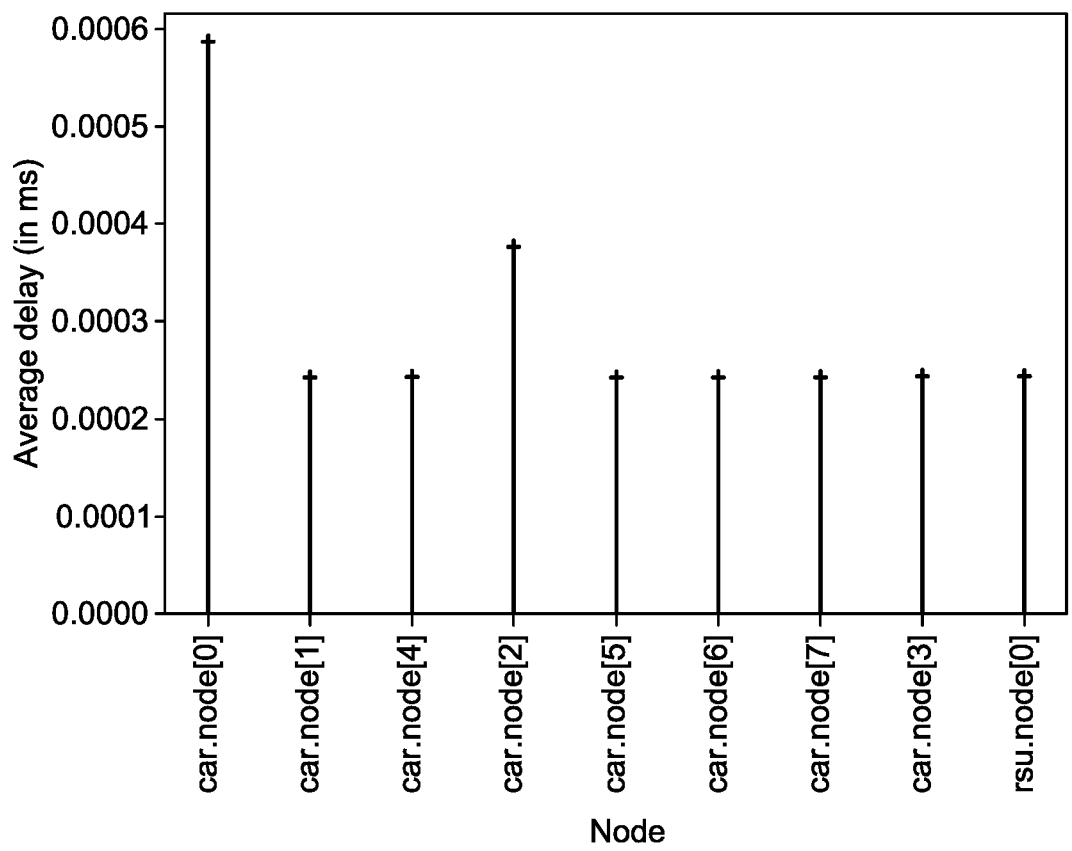
FIG. 28 is a graph illustrating "Car-node" case delay.
Figure 29:
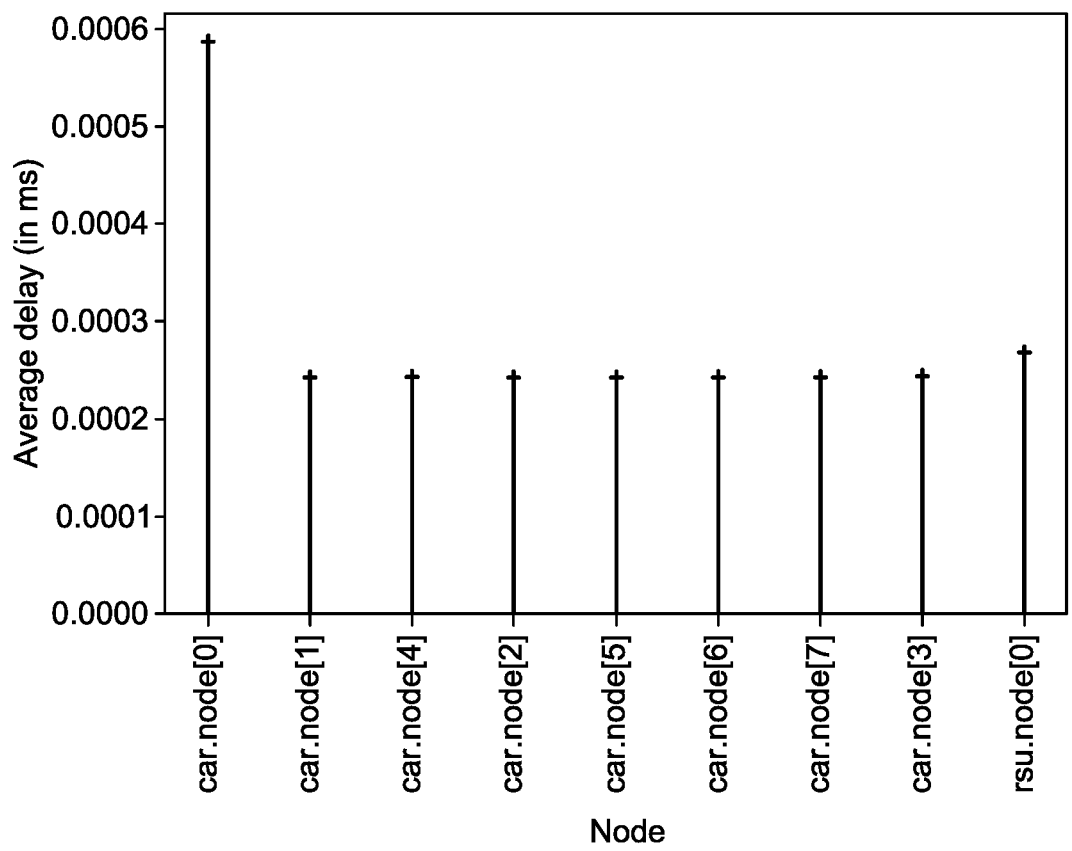
FIG. 29 is a graph illustrating "RSU-node" case delay.

End-To-End Delay: This is the time that was taken for a packet to be transmitted from its source to its destination. FIGS. 28, 29 show the average end-to-end delay for messages received by each node in the C-HealthIER "Car-node" case and "RSU-node" case scenarios, respectively.

FIG. 28 illustrates the C-HealthIER "Car-node" case, car.node[0] and car.node[2] have a higher average delay than other nodes because they receive more messages during the health emergency response as car.node[0] is the vehicle that has the emergency case and car.node[2] is the nearest vehicle that provides the health emergency treatment.

FIG. 29 illustrates the C-HealthIER "RSU-node" case, car.node[0] has the highest average end-to-end delay as it is the vehicle that has the emergency case and received 3 messages. The rsu.node[0] is the second highest node in average delay as it is the nearest RSU that provides health emergency treatment and received 2 messages.

Figure 30:
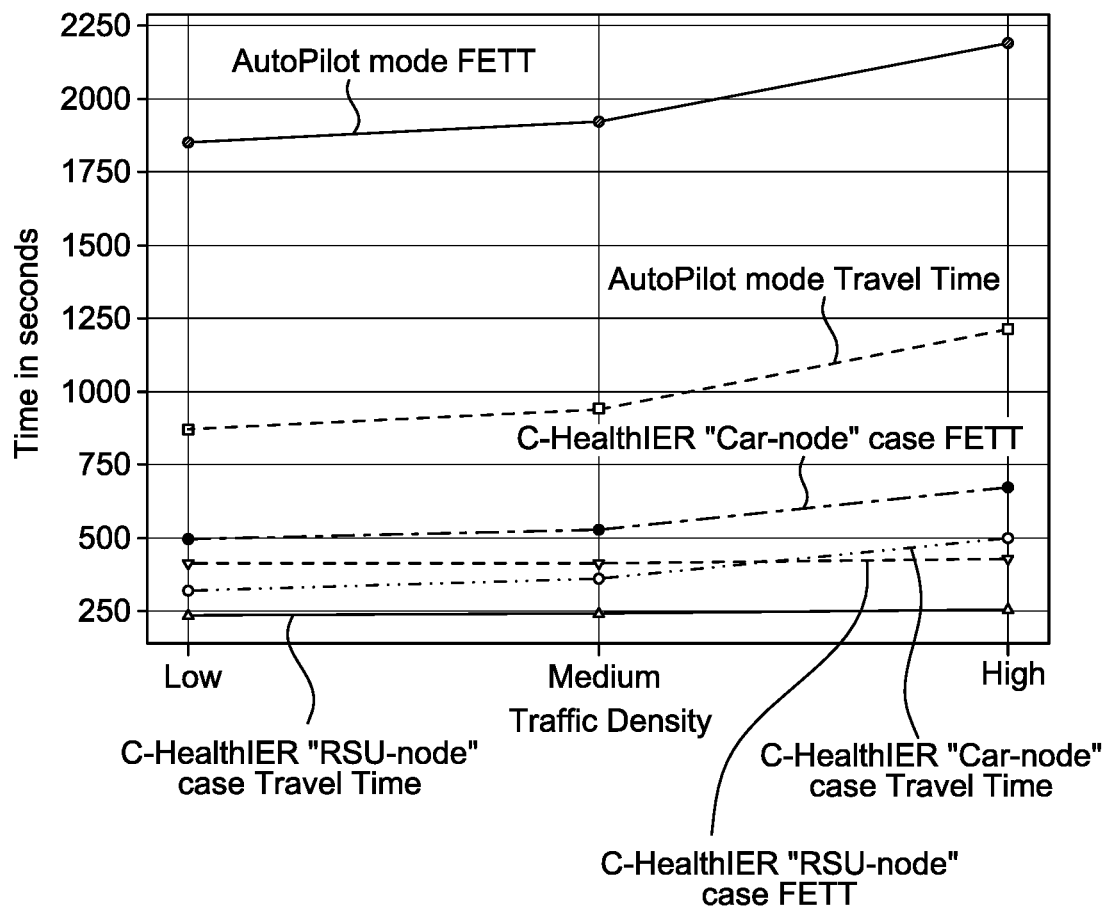
FIG. 30 is a graph illustrating the First Emergency Treatment Time and travel time in traffic density levels.

Traffic Density: The First Emergency Treatment Time (FETT) and Travel Time were also tested on different traffic density levels. The results are illustrated in (FIG. 9) FIG. 30 as follows: The Travel time in the C-HealthIER "Car-node" case and C-HealthIER "RSU-node" case increased slightly while the travel time in the AutoPilot mode increased significantly by increasing the traffic density levels. The First Emergency treatment Time (FETT) also increased in all scenarios over increasing the traffic density levels. However, both C-HealthIER scenarios achieved less FETT time than the AutoPilot mode.

Two Emergency Cases in One Scenario: The FETT and the Travel Time were calculated for these simulation scenarios as shown in Table VII. The results were influenced by the distance between vehicles and different parking areas in scenario 1. Overall, both scenarios achieved FETT and travel time less than FETT and travel time achieved by the normal Autopilot mode scenario for a single vehicle.

TABLE VII

TWO EMERGENCY CASES IN ONE SCENARIO RESULTS

| Scenario | Node | Emergency Treatment Provider | Emergency Occurrence Time | FETT in Sec | Travel Time in Sec |
|---|---|---|---|---|---|
| Scenario 1 | car.node[0] | car.node[2] | 25 | 300 | 276 |
| | car.node[1] | car.node[7] | 27 | 350 | 360 |
| Scenario 2 | car.node[0] | rsu.node[0] | 25 | 457 | 432 |
| | car.node[1] | rsu.node[0] | 27 | 457 | 430 |

Towards reducing the time of receiving the emergency treatment for AVs' passengers with abnormal health conditions within a C-ITS environment the present disclosure describes a cooperative health intelligent emergency response system for AVs that use deep federated learning, V2V and V2I connections to detect abnormal health status of a passenger and react accordingly. Furthermore, the present disclosure implements a set of algorithms in various simulated scenarios to validate the system performance.

In summary of the simulation results, C-HealthIER reduces the TMTT by 92.5% and 95.3% compared to the AutoPilot mode total time. Also, C-HealthIER reduces FETT by 73.2% and 83.1% compared to the AutoPilot mode FETT. For the two scenarios, the C-HealthIER reduces the travel distance by 40.9% and 63.2%, thus, the travel time is reduced by 43.8% and 65.9% compared to the AutoPilot mode. For more collected results at different levels of traffic density, the C-HealthIER still achieves the lowest FETT and travel time compared to the Autopilot mode even during the high-level density.

Alternative Intelligent Cooperative Health Emergency Response Algorithm

In an alternative embodiment, to implement the framework, the intelligent healthcare monitoring system must first operate independently to monitor the health status using the IoT devices and predict the abnormalities in health status using the AI model, and then interact with the emergency response system.

Figure 31:
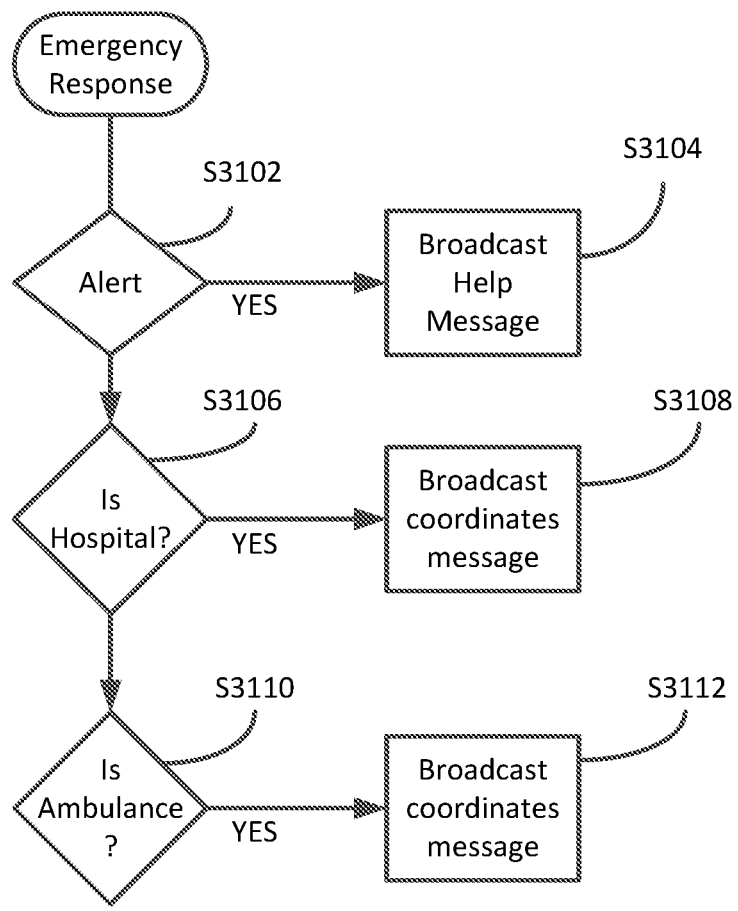
FIG. 31 is a flowchart of an alternative emergency response function, in accordance with an exemplary aspect of the disclosure.

FIG. 31 is a flowchart of an alternative emergency response function, in accordance with an exemplary aspect of the disclosure upon the emergency alert, Algorithm 1 will work in the application layer of the vehicle network. First, in S3102, the AV that has the emergency case ($AV_0$) will, in S3104, broadcast a help_message( ) to the surrounding AVs and RSUs by establishing V2V and V2I connections. The help_message( ) contains a help code to mark the initiated connections as a cooperative health emergency response. In S3106, if the receiver is a hospital or, S3110, an vehicle that is ambulance or has a Doctor, in S3108, S3112, it will broadcast a cords_message( ) back to $AV_0$ contains its coordinates, ID, and type if it is RSU or AV.

Figure 32:
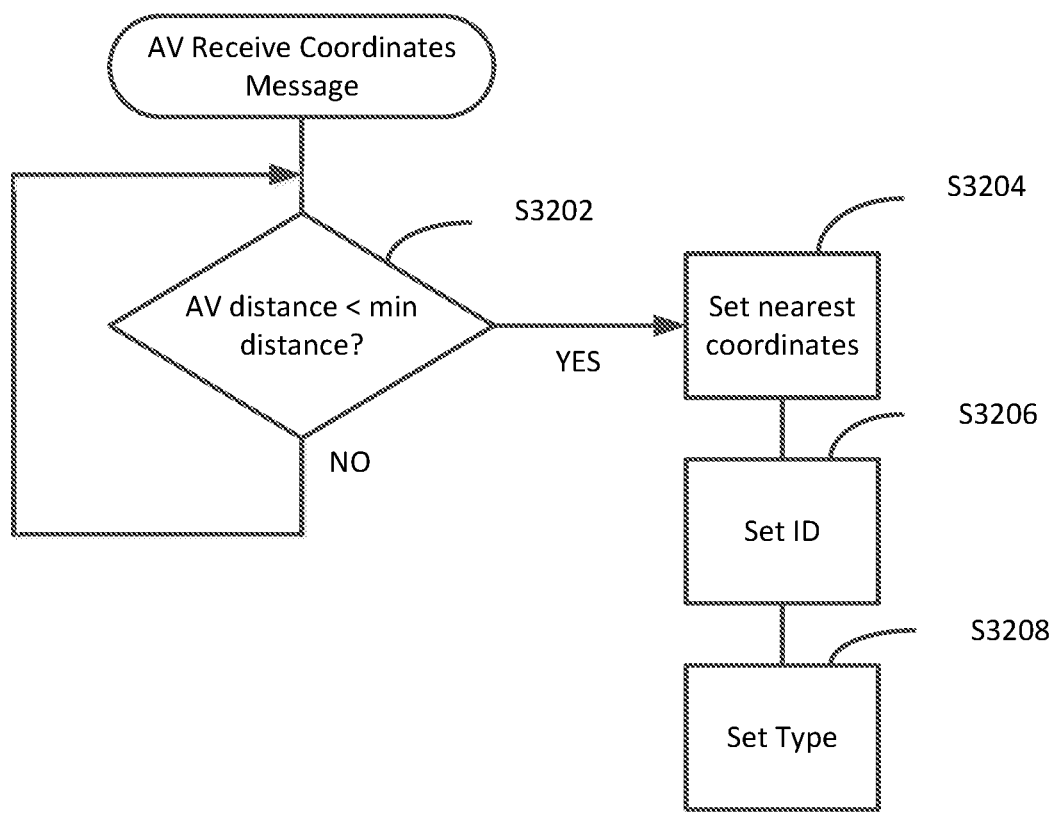
FIG. 32 is a flowchart of AV receive coordinates message, in accordance with an exemplary aspect of the disclosure.

FIG. 32 is a flowchart of AV receive coordinates message, in accordance with an exemplary aspect of the disclosure. While $AV_0$ is receiving the response messages, in S3202, $AV_0$ will calculate the distance with each message sender and compare it with other distances to find the minimum distance. In S3204, $AV_0$ calculates the shortest distance sender ID, in S3206, sets ID, then in S3208, $AV_0$ will set vehicle type.

Figure 33:
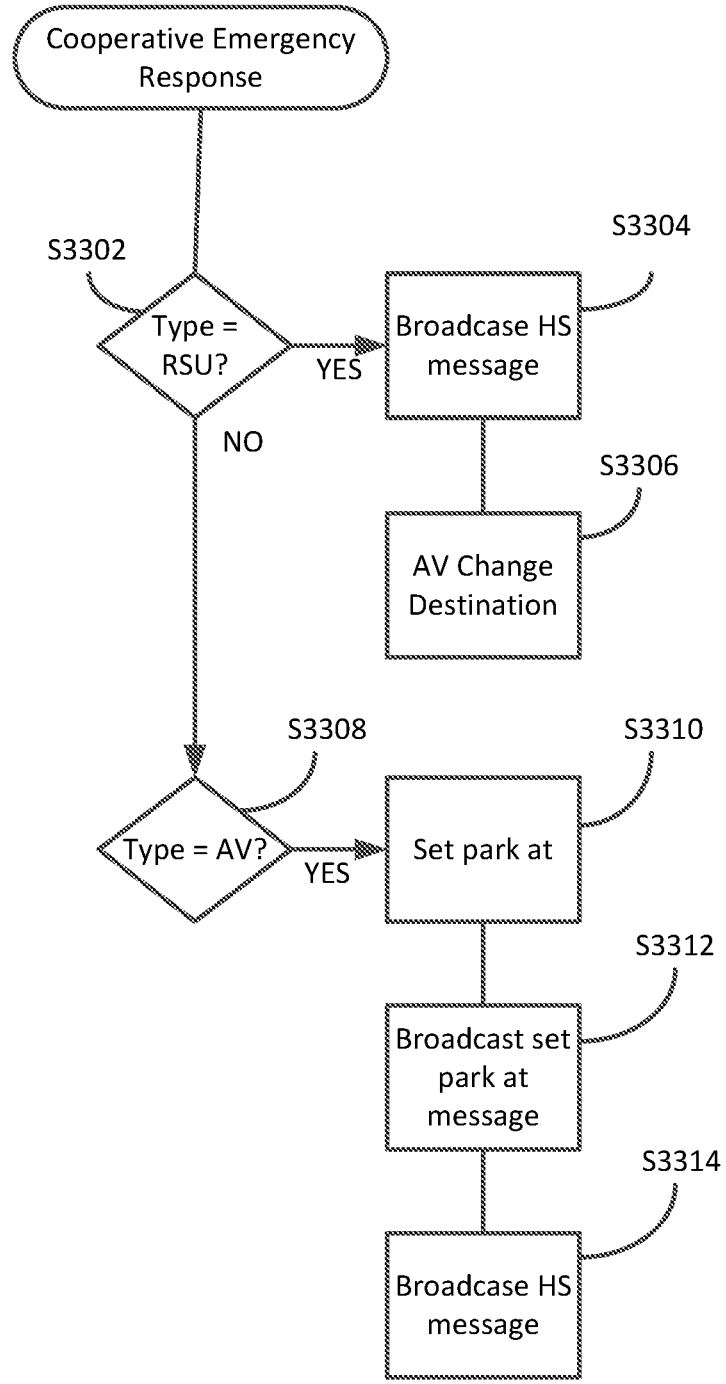
FIG. 33 is a flowchart of cooperative emergency response, in accordance with an exemplary aspect of the disclosure.

FIG. 33 is a flowchart of cooperative emergency response, in accordance with an exemplary aspect of the disclosure. After selecting the shortest distance sender ID, $AV_0$ will check its type. In S3302, if the type is RSU, in S3304, $AV_0$ will broadcast HS message( ) that contains the health status report of the passenger. Moreover, in S3306, $AV_0$ will change its destination to the sender's coordinates. In S3308, if the type is AV, in S3310, $AV_0$ will schedule parking at (x,y) position, then, in S3312, broadcast a set_parkAt_message( ) that contains set_parkAt( ) action at the (x,y) position. Furthermore, in S3314, $AV_0$ will broadcast HS message( ) that contains the health status report of the passenger.

---

Algorithm 1: Cooperative Emergency Response

```
Input: Alert, RSUs, AVs, AV_0
Output: Response Success: S
1  function emergency response( )
2  |    nearest_Coord = (x,y), min_distance = 99999
3  |    S_ID = "xxx", S_type = "xxx"
4  |    If (Alert) then
5  |    |    AV_0  broadcast→  help_message( )
6  |    |    RSUs & AVs  receive←  help_message( )
7  |    end
8  |    for P ∈ RSUs & AVs do
9  |    |    if (P is hospital) then
10 |    |    |  P  broadcast→  coordinates_message(AV_0)
11 |    |    end
12 |    |    ((P is ambulance)||(P has Doctor)) then
13 |    |    |  P  broadcast→  coordinates_message(AV_0)
14 |    |    end
15 |    end
16 |    while AV_0  receive←  coords_message( ) do
17 |    |    AV_x_ Loc = coords_message( ).coordinates
18 |    |    AV_distance= AV_0_ Coord − AV_x_ Coord
19 |    |    If AV_distance < min_distance then
20 |    |    |    min_distance = AV_distance
21 |    |    |    nearest_Coord = AV_x_Coord
22 |    |    |    S_ID = coords_message( ).sender_ID
23 |    |    |    S_type = coords_message( ).type
24 |    |    end
25 |    end
26 |    if (S_type = = RSU) then
27 |    |    AV_0  broadcast→  HS_message(S_ID)
28 |    |    AV_0 ←change_destination(nearest_Coord)
29 |    end
30 |    else if (S_type = = AV) then
31 |    |    AV_0 ← set_park At(x,y)
32 |    |    AV_0  broadcast→  set_parkAt_message(x, y, S_ID)
33 |    |    AV_0  broadcast→  HS_message(S_ID)
34 |    end
35 |    if (AV_S_ID ← receive set_park At_message( )) then
36 |    |    x = set_parkAt_message( ).x
37 |    |    y = set_parkAt_message( ).y
38 |    |    AV_S_ID ← set_parkAt(x,y)
39 |    end
40 |    return S
41 end
```

Figure 34:
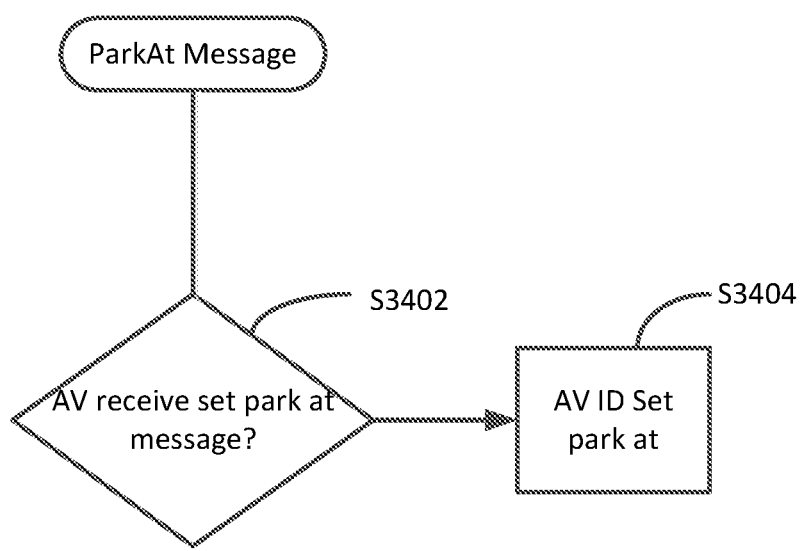
FIG. 34 is a flowchart of a ParkAt Message, in accordance with an exemplary aspect of the disclosure.

FIG. 34 is a flowchart of a ParkAt Message, in accordance with an exemplary aspect of the disclosure. At the final step, in S3402, the shortest distance sender will receive the broadcast messages from $AV_0$. In S3404, from the set_parkAt message( ), x and y positions will be extracted to schedule parking there to meet $AV_0$.

Numerous modifications and variations of the present invention are possible in light of the above teachings. It is therefore to be understood that within the scope of the appended claims, the invention may be practiced otherwise than as specifically described herein.

The invention claimed is:

1. A system for emergency health response, comprising:
a plurality of health monitoring devices including sensors for measuring ECG, heart rate, skin color, motion, respiratory rate, and oxygen level of a user that is inside a subject vehicle;
a local machine learning device to predict abnormalities in a health status of the user that are indications of an impending emergency health condition based on measurements by the plurality of health monitoring devices, wherein the abnormalities in the user's health status and associated sensor data are stored in a distributed blockchain;
a long-range communications device connected to the local machine learning device configured to transmit an emergency alert message to one or more of an emergency response vehicle and a stationary emergency health care facility that are within a communication range of the communications device, and for receiving response messages from an emergency response vehicle and a stationary emergency health care facility that are available to provide emergency treatment for an emergency health condition indicated in the emergency alert message;
a health condition controller to select an emergency response vehicle and a stationary emergency health care facility, as a provider, from among the emergency response vehicles or the stationary emergency health care facilities that sent the response messages;
a global machine learning device configured to:
coordinate with the local machine learning device and perform a federated learning process in which:
the local machine learning device is configured to update local parameters, and
send, using the communications device, the updated local parameters to
the global machine learning device,
wherein the global machine learning device is further configured to:
aggregate updates of local parameters from different local machine learning devices, including the local machine learning device and use the aggregated updated parameters to train the global machine learning device, and
share global parameters of the global machine learning device with the different local machine learning devices;
wherein when the provider is a stationary emergency health care facility, the subject vehicle sets a destination to a provider health care facility and transmits, via the communications device, health status information of the user to the provider health care facility,
and wherein when the provider is an emergency response vehicle, the subject vehicle communicates coordinates as a meeting destination for meeting a provider response vehicle, and transmit, via the communications device, the health status information of the user to the provider response vehicle.

2. The system of claim 1, wherein the local machine learning device is a long short-term memory deep learning network.

3. The system of claim 1, further comprising:
an in-vehicle sub-system that includes the local machine learning device,
wherein when the local machine learning device predicts an abnormality in the health status that indicates an impending emergency health issue, a health alert is issued that triggers an out-vehicle sub-system that uses the long-range communications device to broadcast the emergency alert message.

4. The system of claim 3, wherein the local machine learning device of the in-vehicle sub-system is a component of a mobile device, and
wherein the mobile device includes a short-range wireless communications device for receiving the measurements by the at least one sensor.

5. The system of claim 1, wherein global machine learning device and the local machine learning device are configured to perform the federated learning process with data captured by Internet of Things (IoT) devices to predict the health abnormalities including fatigue, shock, losing consciousness, impending heart attack, impending heart failure, shortness of breath, or brain damage.

6. The system of claim 1, wherein the sensors include a plurality of ECG sensors mounted in a steering wheel of the subject vehicle,
wherein the plurality of ECG sensors include one ECG sensor for placement of one finger of the user and a second ECG sensor for placement of a second finger of the user, in order to obtain two ECG signals.

7. The system of claim 6, wherein the one ECG sensor and the second ECG sensor each have a width to accommodate one finger.

8. The system of claim 6, wherein the plurality of ECG sensors are mounted equally spaced around a parameter of the steering wheel, such that a continuous ECG signal is obtained as the steering wheel is rotated.

9. The system of claim 1, wherein the sensors include a wearable sensor device having a short-range wireless communications device for transmitting ECG signals to the local machine learning device.

10. The system of claim 1, wherein the subject vehicle is configured to self-drive,
wherein when the provider is the stationary emergency health care facility, the subject vehicle sets destination to the provider health care facility and automatically drives to the provider health care facility,
and wherein when the provider is the emergency response vehicle, the subject vehicle communicates coordinates as a meeting destination for meeting the provider response vehicle, and automatically drives to location coordinates of the provider response vehicle.

11. A non-transitory computer readable storage medium storing computer program instructions, which when executed by processing circuitry, performs a method comprising:
measuring, via sensors, ECG, heart rate, skin color, motion, respiratory rate, and oxygen level of a user that is inside a subject vehicle;
predicting, via a local machine learning device, abnormalities in health status of the user that are indications of an impending emergency health condition based on the measurements by the sensors and storing the abnormalities in the user's health status and associated sensor data in a distributed blockchain;

transmitting, via a long-range communications device, an emergency alert message to one or more of an emergency response vehicle and a stationary emergency health care facility that are within a communication range of the communications device, and receiving response messages from an emergency response vehicle and a stationary emergency health care facility that are available to provide emergency treatment for an emergency health condition indicated in the emergency alert message;

training the local machine learning device using a federated learning process in coordination with a global machine learning device, the federated learning process comprising:

conducting a local training process to update local parameters of the local machine learning device;

sending, using the communications device, the updated local parameters to the global machine learning device, which aggregates updates of local parameters from different local machine learning devices and uses the aggregated updated parameters to train the global machine learning device; and receiving aggregated parameters of the global machine learning device;

selecting, by a health condition controller, an emergency response vehicle or a stationary emergency health care facility, as a provider, from among the emergency response vehicles or the stationary emergency health care facilities that sent the response messages;

wherein when the provider is a stationary emergency health care facility, the subject vehicle sets a destination to the provider health care facility and transmits, via the communications device, health status information of the user to the provider health care facility, and wherein when the provider is an emergency response vehicle, the subject vehicle communicates coordinates as a meeting destination for meeting the provider response vehicle, and transmits, via the communication device, the health status information of the user to the provider response vehicle.

12. The computer readable storage medium of claim 11, further comprising:

when the local machine learning device predicts an abnormality in the user's health status, a health alert is issued that triggers an out-vehicle sub-system that includes broadcasting the emergency alert message.

13. The computer readable storage medium of claim 12, wherein the local machine learning device of an in-vehicle sub-system is a component of a mobile device, the method further comprising:

wirelessly receiving the measurements by the sensors via a short-range wireless communications device of the mobile device.

14. The computer readable storage medium of claim 11, further comprising:

performing the federated learning process with data captured by Internet-of-Things (IoT) devices to predict health abnormalities including fatigue, shock, losing consciousness, heart attacks, heart failure, shortness of breath, or brain damage.

15. The computer readable storage medium of claim 11, further comprising: measuring the ECG by a plurality of ECG sensors mounted equally spaced around a parameter of a steering wheel of the subject vehicle, such that a continuous ECG signal is obtained as the steering wheel is rotated.

16. The computer readable storage medium of claim 11, further comprising:

transmitting, via a communications device, an emergency alert message when the predicted abnormality in the user's health status is above a predetermined risk level.

\* \* \* \* \*